US011576913B2

(12) United States Patent
Harris et al.

(10) Patent No.: US 11,576,913 B2
(45) Date of Patent: Feb. 14, 2023

(54) SLEEP DISORDER TREATMENT AND PREVENTION

(71) Applicant: Purdue Pharma L.P., Stamford, CT (US)

(72) Inventors: Stephen C. Harris, Weston, CT (US); Ram P. Kapil, Princeton Junction, NJ (US); Donald J. Kyle, Yardley, PA (US); Garth Whiteside, Yardley, PA (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 16/964,174

(22) PCT Filed: Jan. 22, 2019

(86) PCT No.: PCT/IB2019/050522
§ 371 (c)(1),
(2) Date: Jul. 22, 2020

(87) PCT Pub. No.: WO2019/145850
PCT Pub. Date: Aug. 1, 2019

(65) Prior Publication Data
US 2020/0345726 A1    Nov. 5, 2020

Related U.S. Application Data

(60) Provisional application No. 62/621,290, filed on Jan. 24, 2018.

(51) Int. Cl.
| | | |
|---|---|---|
| *A61K 31/498* | (2006.01) | |
| *A61P 25/20* | (2006.01) | |
| *A61P 25/32* | (2006.01) | |
| *A61K 9/00* | (2006.01) | |
| *A61K 31/138* | (2006.01) | |
| *A61K 31/145* | (2006.01) | |
| *A61K 31/16* | (2006.01) | |
| *A61K 31/197* | (2006.01) | |
| *A61K 31/485* | (2006.01) | |

(Continued)

(52) U.S. Cl.
CPC ............ *A61K 31/498* (2013.01); *A61K 9/006* (2013.01); *A61K 9/0053* (2013.01); *A61K 9/0056* (2013.01); *A61K 31/138* (2013.01); *A61K 31/145* (2013.01); *A61K 31/16* (2013.01); *A61K 31/197* (2013.01); *A61K 31/485* (2013.01); *A61K 31/554* (2013.01); *A61K 31/7048* (2013.01); *A61P 25/20* (2018.01); *A61P 25/32* (2018.01)

(58) Field of Classification Search
CPC .. A61K 31/498; A61K 31/138; A61K 31/145; A61K 31/16; A61K 31/197; A61K 31/485; A61K 31/554; A61K 31/7048; A61K 45/06; A61K 9/0053; A61K 9/0056; A61K 9/006; A61K 9/2054; A61P 25/20; A61P 25/32
See application file for complete search history.

(56) References Cited

U.S. PATENT DOCUMENTS

| 7,566,728 B2 | 7/2009 | Teshima et al. |
| 9,040,533 B2 * | 5/2015 | Marra .................. A61P 11/14 |
| | | 514/249 |

(Continued)

FOREIGN PATENT DOCUMENTS

| WO | 06/025267 A1 | 3/2006 |
| WO | 09/027820 A2 | 3/2009 |

(Continued)

OTHER PUBLICATIONS

Landolt (CNS Drugs, 15, 5, 413-425, 2001). (Year: 2001).*

(Continued)

*Primary Examiner* — Umamaheswari Ramachandran
(74) *Attorney, Agent, or Firm* — Sterne, Kessler, Goldstein & Fox PLLC

(57) ABSTRACT

The disclosure relates to methods for treating or preventing an Insomnia Disorder by administering to a human in need thereof a compound of formula (I), or a compound of formula (IA), (IB), or (IC), or a solvate thereof, in a daily dose of from about 0.5 mg to about 6.0 mg. In certain embodiments, such compounds effectively treat or prevent an Insomnia Disorder in the animal, while producing reduced side effects compared to previously available compounds.

16 Claims, 26 Drawing Sheets

(51) Int. Cl.
*A61K 31/554* (2006.01)
*A61K 31/7048* (2006.01)

(56) References Cited

U.S. PATENT DOCUMENTS

2005/0119308 A1  6/2005  Teshima et al.
2014/0187544 A1  7/2014  Marra et al.
2019/0282836 A1  9/2019  Harris et al.

FOREIGN PATENT DOCUMENTS

| WO | 10/010458 A1 | 1/2010 |
| WO | 14/102590 A1 | 7/2014 |
| WO | 14/102592 A2 | 7/2014 |
| WO | 18/020418 A1 | 2/2018 |

OTHER PUBLICATIONS

International Search Report corresponding to International Application No. PCT/IB2019/050522 dated Apr. 26, 2019.
International Search Report corresponding to International Application No. PCT/IB2017/054506 dated Oct. 18, 2017.
Mollereau et al., "Tissue distribution of the opioid receptor-like (ORL1) receptor," Peptides 21, pp. 907-917 (2000).
Teshima et al., "Nonphotic entrainment of the circadian body temperature rhythm by the selective ORL1 receptor agonist W-212393 in rats," British Journal of Pharmacology, 2005, vol. 146, p. 33-40.
Written Opinion of the International Searching Authority corresponding to International Application No. PCT/IB2019/050522 dated Apr. 26, 2019.

\* cited by examiner

SLEEP DISORDER TREATMENT AND PREVENTION

This application is a national stage of International application serial no. PCT/IB2019/050522, filed Jan. 22, 2019, which claims the benefit under 35 U.S.C. § 119(e) of U.S. provisional application No. 62/621,290, filed Jan. 24, 2018, the contents of all of which are incorporated herein by reference.

1. FIELD

The disclosure relates to methods for treating or preventing a sleep disorder by administering a compound of formula (I), (IA), (IB), or (IC), or a solvate thereof, to an animal, e.g., a human, in need of such treatment. In certain embodiments, such compounds effectively treat or prevent a sleep disorder in the animal, while producing fewer or reduced side effects compared to previously available compounds.

2. BACKGROUND

Sleep disorders are widely prevalent world-wide and in the United States. Under one classification scheme, six broad categories of sleep disorders have been identified: (i) insomnia, (ii) hypersomnia, (iii) parasomnia, (iv) circadian rhythm sleep-wake disorders, (v) sleep-related breathing disorders, and (vi) sleep movement disorders. Under another classification scheme, ten broad primary categories of sleep disorders have been identified: (1) insomnia disorder, (2) hypersomnolence disorder, (3) narcolepsy, (4) breathing-related sleep disorders, (5) circadian rhythm sleep-wake disorders, (6) non-rapid eye movement ("NREM") sleep arousal disorders, (7) nightmare disorder, (8) rapid eye movement sleep behavior disorder, (9) restless leg syndrome, and (10) substance/medication-induced sleep disorder. Under either scheme, multiple subcategories are recognized within each of the broad categories.

Insomnia has been defined as the disorder, with no obvious cause, of difficulty in falling asleep and/or staying asleep. Insomnia is the most common sleep disorder affecting millions of people as either a primary or comorbid disorder. Insomnia has been defined as both a disorder (see, e.g., Espie, "Insomnia: Conceptual Issues in the Development, Persistence and Treatment of Sleep Disorder in Adults," *Ann. Reviews Psychology* 53:215-243 (2002)) and a symptom (see, e.g., Hirshkowitz, "Neuropsychiatric Aspects of Sleep and Sleep Disorders," Chapter 10 (pp. 315-340) in *Essentials of Neuropsychiatry and Clinical Neurosciences*, Yudofsy et al., eds., 4$^{th}$ Ed., American Psychiatric Publishing, Arlington, Va. (2004)), and this distinction may affect its conceptualization from both research and clinical perspectives. Whether insomnia is viewed as a disorder or a symptom, however, it nevertheless has a profound effect on the individual and on society. Insomnia results in significant distress and/or functional impairments in those who suffer therefrom, underscoring the need for appropriate treatment.

Estimates of the prevalence of insomnia depend on the criteria used in its definition and, more importantly, the population studied. A general consensus developed from a number of population-based studies drawing from different countries is that approximately 30% of adults report one or more of the symptoms of insomnia: difficulty initiating sleep, difficulty maintaining sleep, waking up too early and, in some cases, nonrestorative or poor quality of sleep. If the diagnostic criteria include perceived daytime impairment or distress as a result of the insomnia, in 2005 the NIH determined the prevalence of insomnia in the U.S. to be approximately 10%. If insomnia persists for at least one month and is not due to another sleep disorder, mental disorder, substance use disorder, or medical condition, the prevalence is approximately 6%.

Alcohol dependence is a very common substance use disorder worldwide. Alcohol use disorder, defined according to Diagnostic and Statistical Manual of Mental Disorders criteria (DSM-5, 5$^{th}$ Ed., Amer. Psychiatric Publishing, Arlington, Va. (2013)), including all severity classifications, has a lifetime occurrence of about 29% in the United States (Grant et al., "Epidemiology of DSM-5 Alcohol Use Disorder," *JAMA Psychiatry* 72(8):757-766 (2015)). Additionally, alcohol dependence, classified as a separate condition under the DSM 4$^{th}$ Edition (DSM-IV, 4$^{th}$ Ed., Amer. Psychiatric Publishing, Arlington, Va. (1994)) has a lifetime occurrence of about 12.5% in the United States (Hasin et al., "Prevalence, correlates, disability, and comorbidity of DSM-IV alcohol abuse and dependence in the United States," *Arch. Gen. Psychiatry* 64:830-842 (2007)).

It is known that sleep disorders are more common among alcoholics than among non-alcoholics (Brower, "Alcohol's Effects on Sleep in Alcoholics," *Alcohol Res. Health* 25(2): 110-125 (2001)). For example, Brower discloses, in the general population in the prior 6 months, insomnia affected 18% of alcoholics as compared with 10% of non-alcoholics and that rates of insomnia are even higher among patients admitted for alcoholism treatment, ranging from 36% to 72%, depending on sample characteristics, the type of sleep-measuring instrument, the amount of time elapsed since the last drink, and the presence of other disorders. Another reference discloses that 91% of alcoholic participants in a sleep study suffered from a sleep disturbance as measured by the well-accepted Pittsburgh Sleep Quality Index ("PSQI") (Conroy et al., "Perception of Sleep in Recovering Alcohol Dependent Patients with Insomnia: Relationship to Future Drinking," *Alcohol Clin. Exp. Res.* 30(12):1992-1999 (2006)).

Polysomnography ("PSG") is a multiparametric test used for studying sleep and for diagnosing sleep disorders. A polysomnography evaluation involves the comprehensive measurement and recording of biophysiological changes occurring during sleep. This typically involves, during the time in bed, continuous recording (in the form of a polysomnogram) of the brain waves (electroencephalogram or "EEG"), heart rate and rhythm (electrocardiogram or "ECG"), eye movements (electrooculogram or "EOG"), muscle activity and limb movements (electromyogram or "EMG"), blood oxygen level, breathing pattern and air flow, body position, and snoring and other noises made during sleep. Exclusive of the eyes, EMG typically evaluates chin muscle tone, leg movements, chest wall movement, and upper abdominal wall movement.

Existing drugs are known to moderate sleep via a variety of mechanisms. For example, benzodiazepines (e.g., lorazepam, temazepam, triazolam), barbiturates (e.g., phenobarbital, pentobarbital, secobarbital), and so-called "z-drugs" (e.g., zaleplon, zolpidem, zopiclone) all increase sleep by potentiating the action of GABA via action on the GABAa receptor. The benzodiazepines potentiate GABA by increasing the frequency of chloride channel opening. The barbiturates potentiate GABA by increasing the duration of chloride channel opening. The z-drugs are agonists at the GABAaγ1 subunit. Other existing drugs increase sleep by different mechanisms, for example, ramelteon (ROZEREM)

is an agonist for the two high-affinity G protein-coupled receptors, termed $MT_1$ and $MT_2$, in the suprachiasmatic nucleus ("SCN") while other drugs (e.g., suvorexant) are orexin receptor antagonists. Many of these existing drugs are classified as controlled substances under the Controlled Substances Act and thus carry the risk of abuse and addiction. For example, lorazepam, temazepam, triazolam, phenobarbital, zaleplon, zolpidem, zopiclone, and suvorexant are all classified as Schedule IV Controlled Substances pursuant to 21 CFR § 1308.14 while pentobarbital and secobarbital are each classified as Schedule II Controlled Substances, that is, substances that have a high potential for abuse which may lead to severe psychological or physical dependence.

Cautionary warnings also pertain to certain of these existing drugs. For example, the March 2017 prescribing information for zolpidem tartrate (AMBIEN) states that persons with a history of addiction to, or abuse of, alcohol are at increased risk for misuse, abuse and addiction to zolpidem; avoid AMBIEN use in patients with severe hepatic impairment; and persons experiencing insomnia are instructed to advise their physician if they have a history of alcohol abuse or addiction and/or have liver or kidney disease. Additionally, the August 2014 prescribing information for suvorexant (BELSOMRA) states that individuals with a history of abuse or addiction to alcohol or other drugs may be at increased risk for abuse and addiction to BELSOMRA; the most common adverse reaction of patients treated with BELSOMRA is somnolence; and that sleep paralysis and hypnagogic/hypnopompic hallucinations, including vivid and disturbing perceptions by the patient, can occur with the use of BELSOMRA.

Still other existing drugs or drug-like substances are known to decrease sleep, for example, modafinil, tricyclic antidepressants (e.g., desipramine, protriptyline, trimipramine), selective serotonin reuptake inhibitors (e.g., citalopram, fluoxetine, paroxetine), norepinephrine reuptake inhibitors (e.g., atomoxetine, maprotiline, reboxetine), and stimulants (e.g., amphetamine, caffeine).

Identification of the ORL-1 receptor as distinct from the three long-known major classes of opioid receptors in the central nervous system—mu, kappa, and delta—resulted from experimentation on these opioid receptor classes. The ORL-1 receptor was identified and classified as an opioid receptor based only on amino acid sequence homology, as the ORL-1 receptor did not exhibit overlapping pharmacology with the classic mu opioid receptor. It was initially demonstrated that non-selective ligands having a high affinity for mu, kappa, and delta receptors had low affinity for the ORL-1 receptor. This characteristic, along with the fact that an endogenous ligand had not yet been discovered, led to the term "orphan receptor." See, e.g., Henderson et al., "The orphan opioid receptor and its endogenous ligand—nociceptin/orphanin FQ," *Trends Pharmacol. Sci.* 18(8):293-300 (1997). Subsequent research led to the isolation and structure of the endogenous ligand of the ORL-1 receptor (i.e., nociceptin; also known as orphanin FQ or OFQ), a seventeen amino acid peptide structurally similar to members of the opioid peptide family. For a general discussion of ORL-1 receptors, see Calo' et al., "Pharmacology of nociceptin and its receptor: a novel therapeutic target," *Br. J. Pharmacol.* 129:1261-1283 (2000).

U.S. Pat. Nos. 8,476,271, 8,846,929, 9,145,408, 9,278,967, and 9,527,840 and U.S. Patent Application Publication No. US 2016/0009717 A1 each disclose compounds having an affinity for the ORL-1 receptor.

U.S. Pat. No. 9,040,533, and U.S. Patent Application Publication Nos. US 2015/0238485 A1 and US 2016/0272640 A1 each disclose compounds having an affinity for the ORL-1 receptor.

U.S. Pat. Nos. 7,566,728 and 8,003,669 purport to disclose ORL-1 receptor agonist compounds useful for treating circadian rhythm sleep disorder.

Teshima et al. ("Nonphotic entrainment of the circadian body temperature rhythm by the selective ORL1 receptor agonist W-212393 in rats," *Brit. J. Pharmacol.* 146:33-40 (2005)) describes that the ORL-1 receptor agonist W-212393 may influence circadian entrainment in rats.

Zaveri ("Nociceptin Opioid Receptor (NOP) as a Therapeutic Target: Progress in Translation from Preclinical Research to Clinical Utility," *J. Med. Chem.* 59(15):7011-7028 (2016)) reviews recent progress towards validating the NOP system as a therapeutic target.

International Application No. PCT/IB2017/054506 discloses compounds having an affinity for the ORL-1 receptor useful for treating and/or preventing sleep disorders.

The present disclosure provides certain ORL-1 receptor modulators useful for treating or preventing sleep disorders, e.g., an Insomnia Disorder.

Citation of any reference in Section 2 of this application is not to be construed as an admission that such reference is prior art to the present application.

3. SUMMARY

In one aspect, the disclosure provides methods for treating a sleep disorder in an animal comprising administering a therapeutically effective amount of one or more compounds of formula (I), (IA), (IB), or (IC):

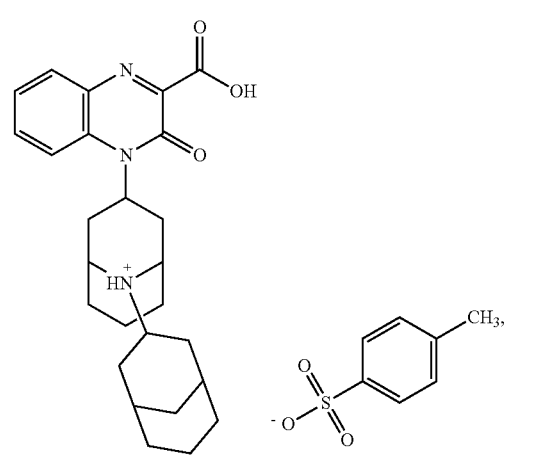

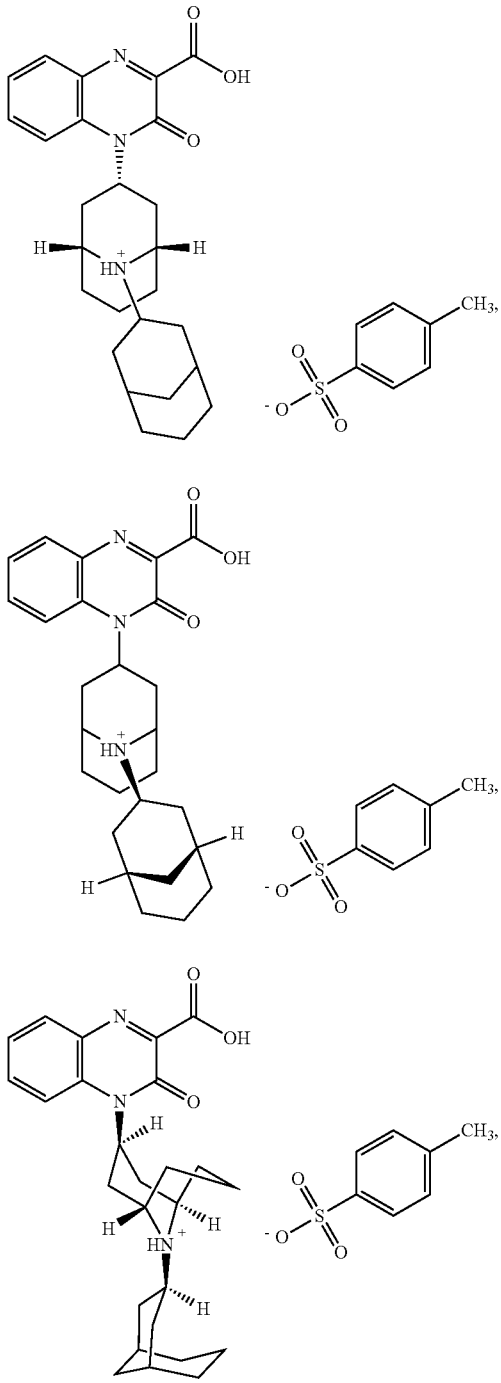

or a solvate thereof, to an animal in need of such treatment. In certain embodiments, such compounds of formula (I), (IA), (IB), or (IC), or a solvate thereof, effectively treat a sleep disorder in the animal, while producing fewer or reduced side effects compared to previously available compounds. In certain embodiments, such compounds of formula (I), (IA), (IB), or (IC), or a solvate thereof, exhibit affinity for the human ORL-1 receptor. Compounds of formula (IA), (IB), and (IC) may each be referred to as Compound (1A), Compound (1B), and Compound (1C), respectively.

In another embodiment of the disclosure, compositions are disclosed which comprise an effective amount of a compound of formula (I), (IA), (IB), or (IC), or a solvate thereof, and a pharmaceutically acceptable carrier or excipient. The compositions are useful for treating or preventing a sleep disorder in an animal.

In another embodiment of the disclosure, an effective amount of a compound of formula (I), (IA), (IB), or (IC), or a solvate thereof, or composition comprising the same, can be used to treat or prevent a sleep disorder including, but not limited to insomnia (e.g., "adult" insomnia, child insomnia, and middle-of-the-night insomnia); an alcohol-induced sleep disorder (e.g., insomnia-type alcohol-induced sleep disorder, daytime sleepiness type alcohol-induced sleep disorder, parasomnia type alcohol-induced sleep disorder, and mixed type alcohol-induced sleep disorder); insomnia in alcohol use disorder; a sleep disturbance associated with alcohol cessation (e.g., insomnia associated with alcohol cessation); hypersomnia (such as insufficient sleep syndrome); circadian rhythm sleep-wake disorder (e.g., delayed sleep-wake phase, advanced sleep-wake phase, irregular sleep-wake rhythm, non-24-hour sleep-wake rhythm, shift work syndrome, and jet lag); or any combination thereof. When used to treat or prevent a sleep disorder, such as those included above, an effective amount of a compound of formula (I), (IA), (IB), or (IC), or a solvate thereof, or composition comprising the same, can be administered to a patient who is receiving one or more concomitant therapies for treating or preventing addictive alcohol use disorder.

In another embodiment of the disclosure, an effective amount of a compound of formula (I), (IA), (IB), or (IC), or a solvate thereof, or composition comprising the same, can be used to treat or prevent a sleep disorder including, but not limited to an Insomnia Disorder (e.g., "adult" insomnia, child insomnia, and middle-of-the-night insomnia).

In another embodiment of the disclosure, an effective amount of a compound of formula (I), (IA), (IB), or (IC), or a solvate thereof, or composition comprising the same, can be used to treat or prevent a sleep disorder including, but not limited to, an Insomnia Disorder associated with alcohol, e.g., insomnia-type alcohol-induced sleep disorder and mixed type alcohol-induced sleep disorder; insomnia in alcohol use disorder; insomnia associated with alcohol cessation; or any combination thereof.

The disclosure can be understood more fully by reference to the following detailed description and illustrative examples, which are intended to exemplify non-limiting embodiments of the disclosure.

4. BRIEF DESCRIPTION OF THE FIGURES

Figure 22:
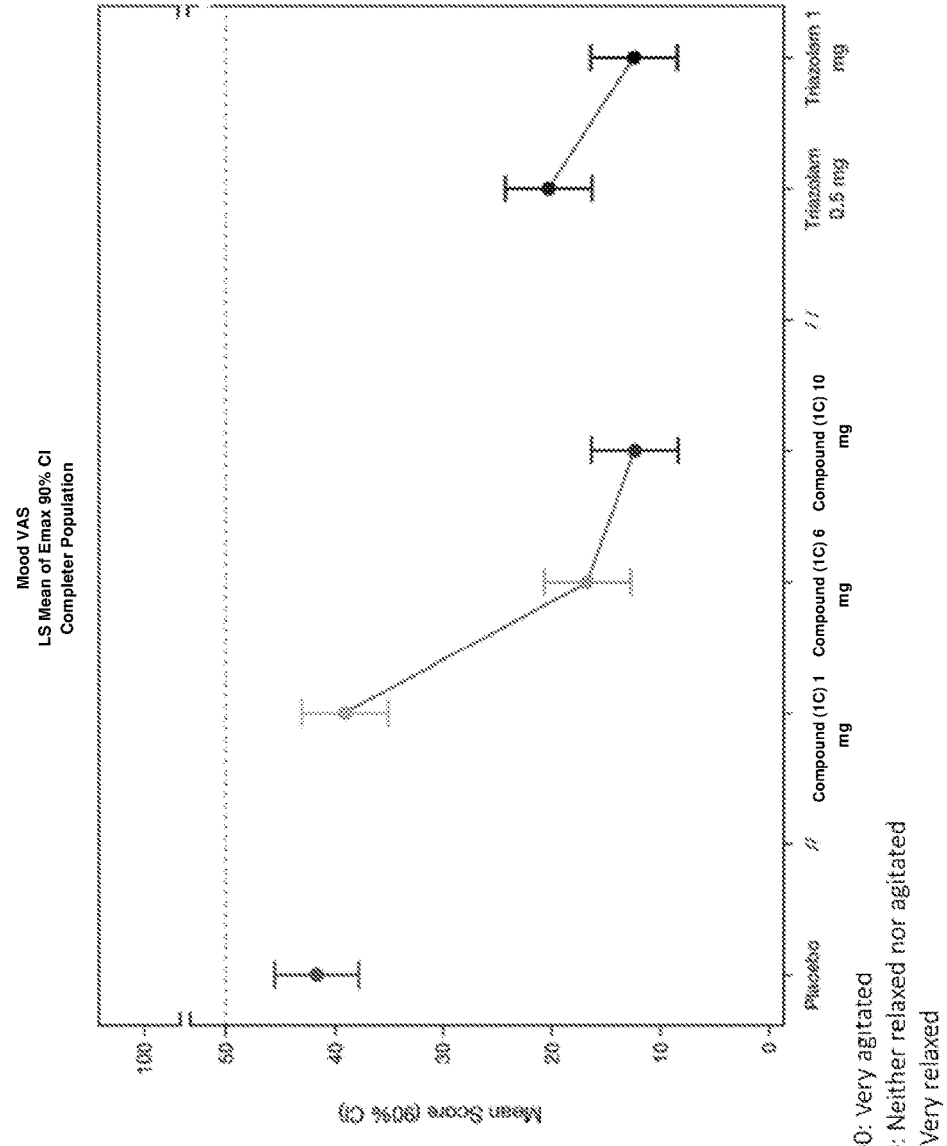

FIG. 22 shows a plot of subjective sedative effects, agitation/relaxation, to Compound (1C) at doses of 1 mg, 6 mg, and 10 mg, triazolam at doses of 0.5 mg and 1.0 mg, and placebo in example 11.

Figure 23:
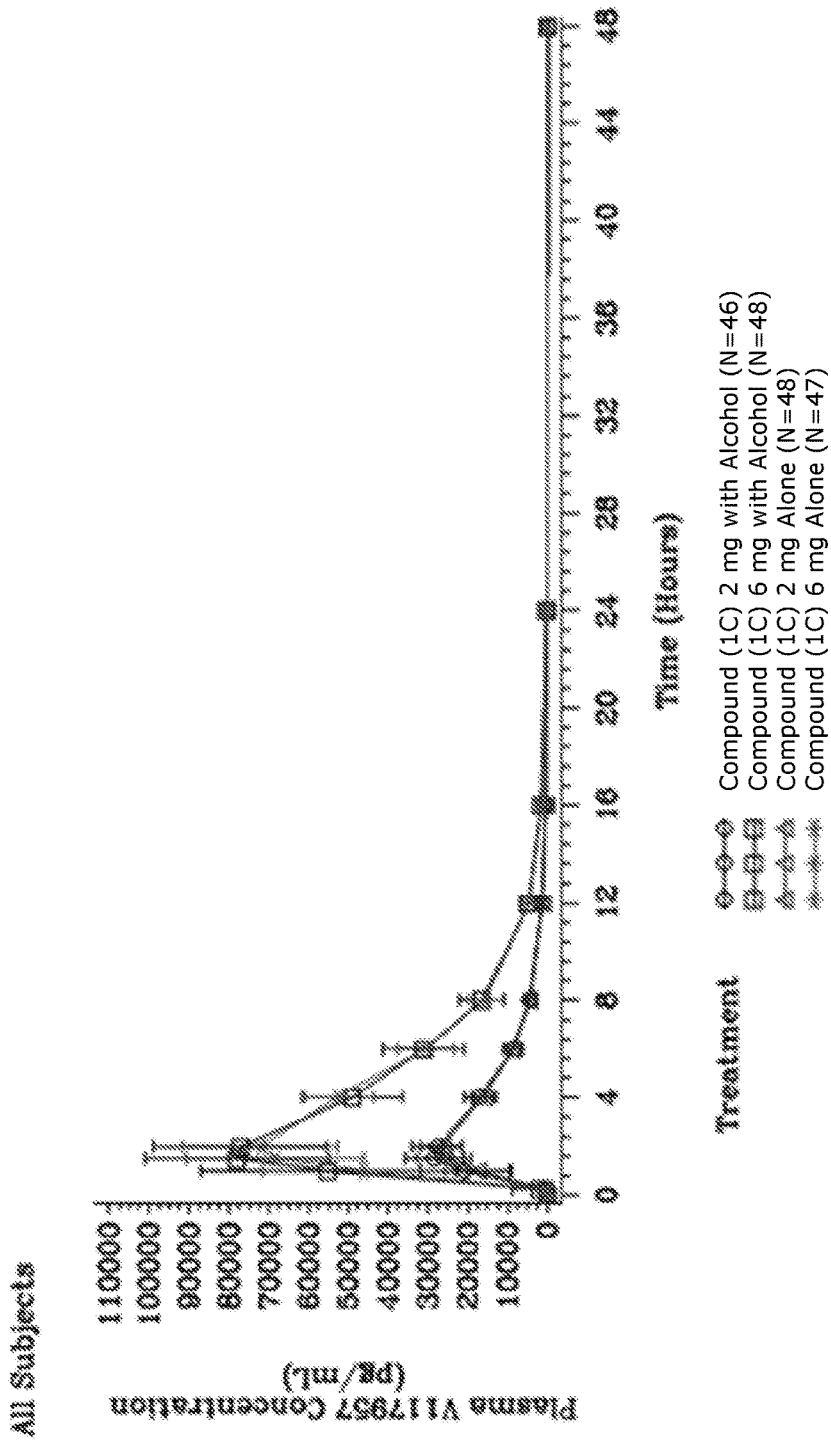

FIG. 23 shows a plot of the pharmacokinetic ("PK") profile of Compound (1C) administered at doses of 2 mg and 6 mg alone and combined with 0.7 g/kg ethanol in Example 12.

Figure 24:
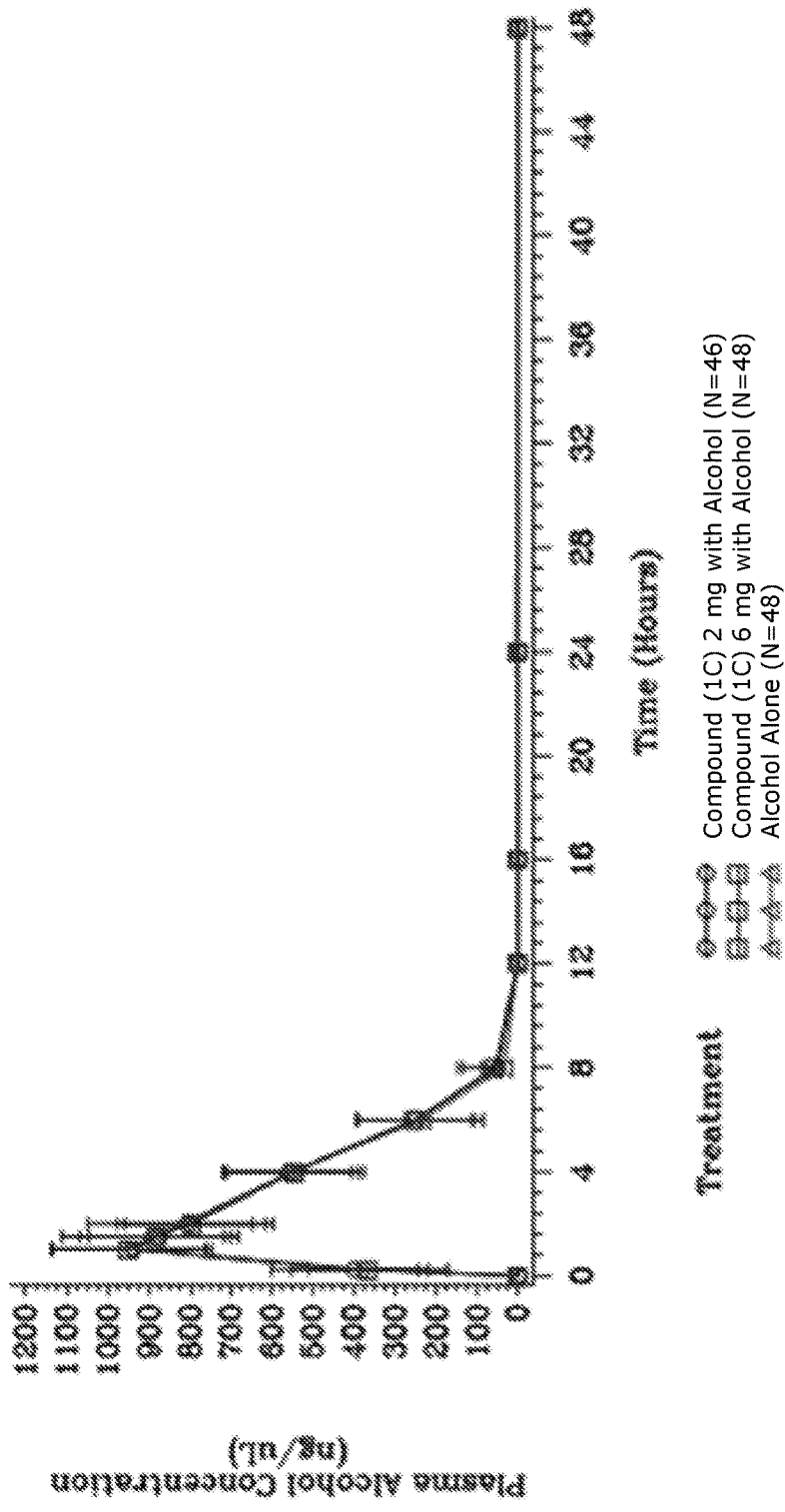

FIG. 24 shows a plot of the pharmacokinetic ("PK") profile of Compound (1C) administered at doses of 2 mg and 6 mg combined with 0.7 g/kg ethanol in Example 12.

Figure 25:
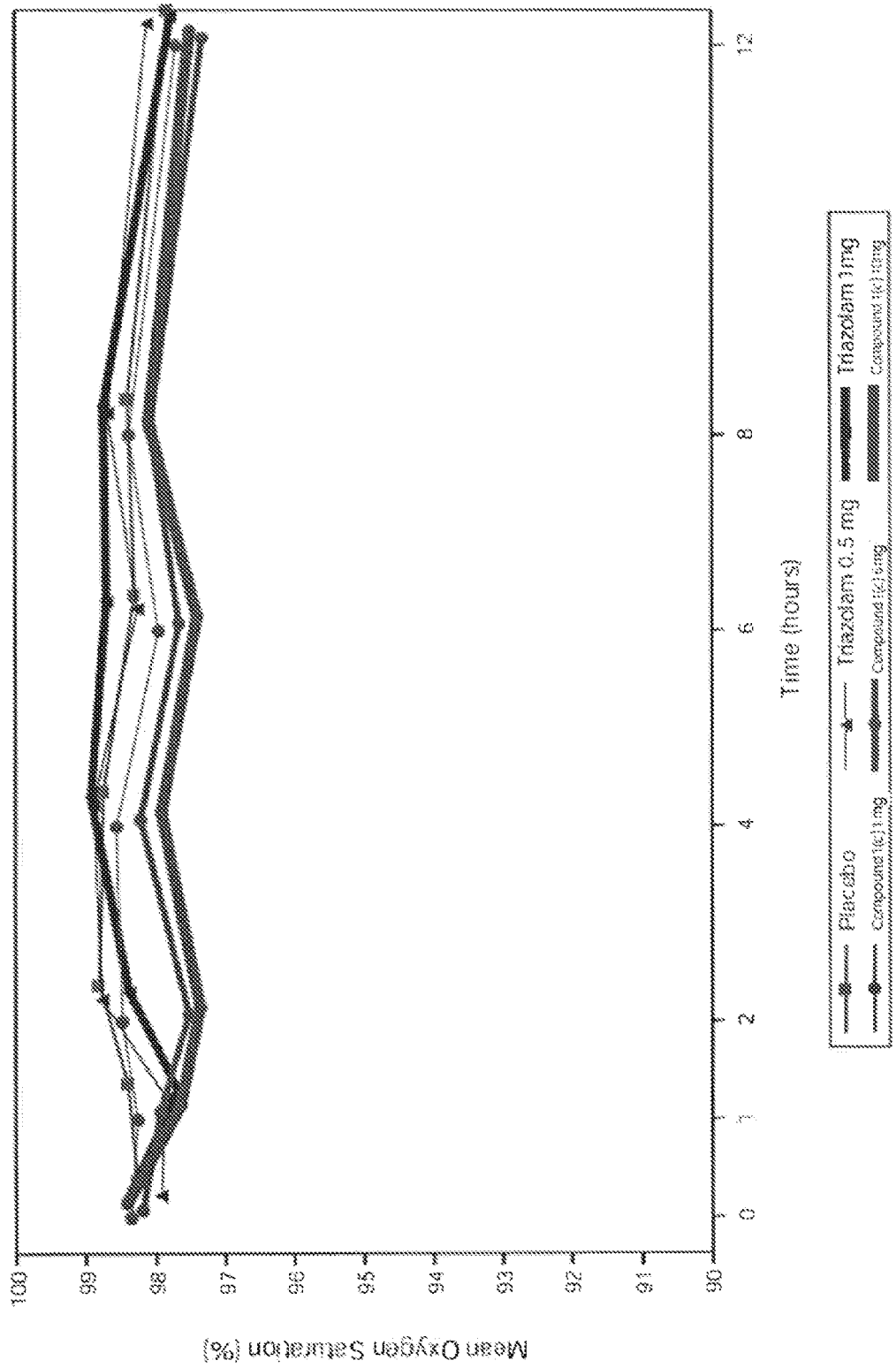

FIG. 25 shows a line chart summary of oxygen saturation in study completers who received Compound (1C) at doses of 1 mg, 6 mg, and 10 mg, triazolam at doses of 0.5 mg and 1.0 mg, and placebo in Example 11.

Figure 26:
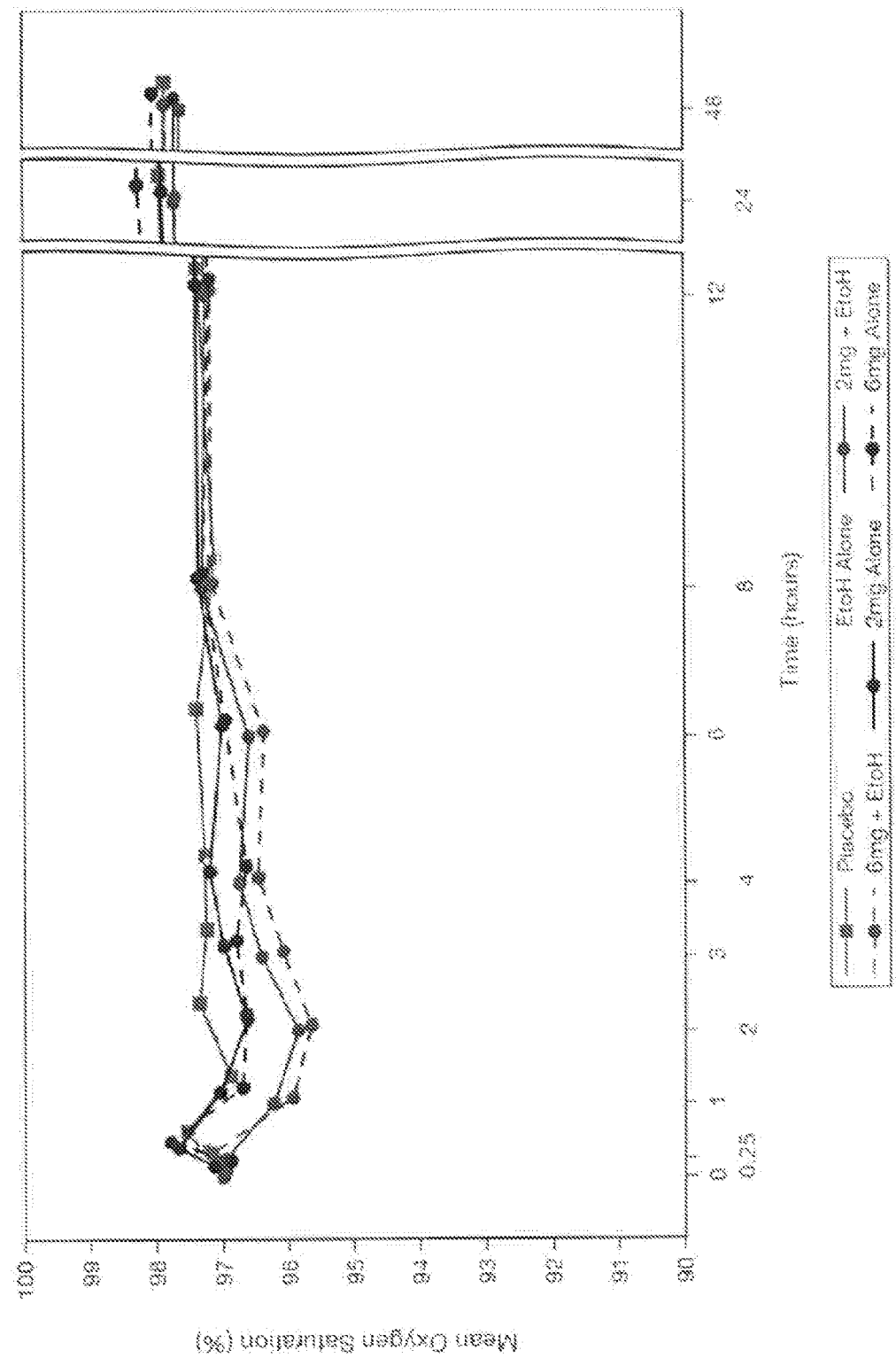

FIG. 26 shows a line chart summary of oxygen saturation in study completers who received Compound (1C) administered at doses of 2 mg and 6 mg alone and combined with 0.7 g/kg ethanol, 0.7 g/kg ethanol alone, and placebo in Example 12.

5. DETAILED DESCRIPTION

The invention includes the following exemplary, non-limiting, embodiments:

(1) A method for treating or preventing an Insomnia Disorder, comprising administering to a human in need thereof a therapeutically effective amount of a compound of Formula (I)

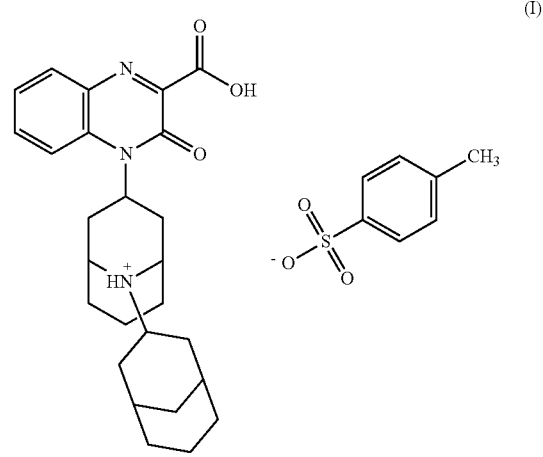 [SMILES: O=C(O)c1nc2ccccc2n(C2CC3CCCC(C2)N3C2CC3CCCC(C3)C2)c1=O ; Cc1ccc(S(=O)(=O)O)cc1]

or a solvate thereof in a daily dose of from about 0.5 mg to about 6.0 mg.

(2) The method of the above (1), wherein the compound is a compound of Formula (IA)

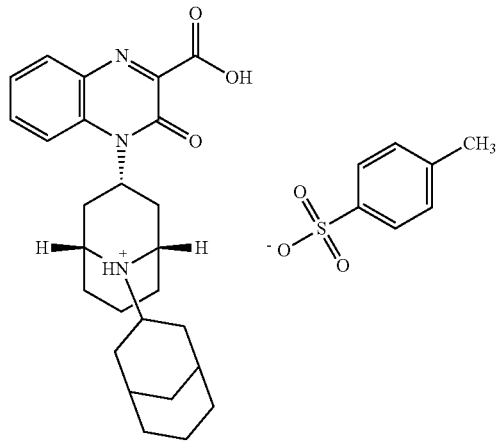

or a solvate thereof.

(3) The method of the above (1), wherein the compound is a compound of Formula (IB)

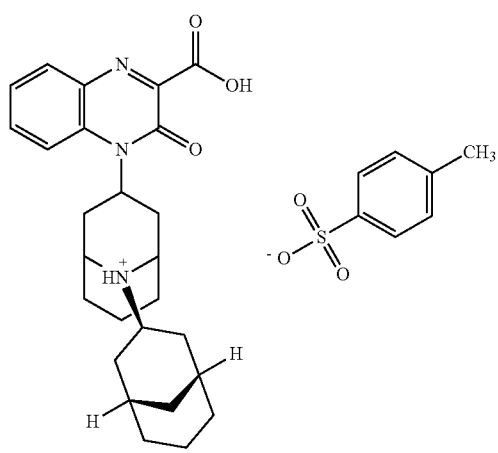

or a solvate thereof.

(4) The method of any one of the above (1)-(3), wherein the compound is the compound of Formula (IC)

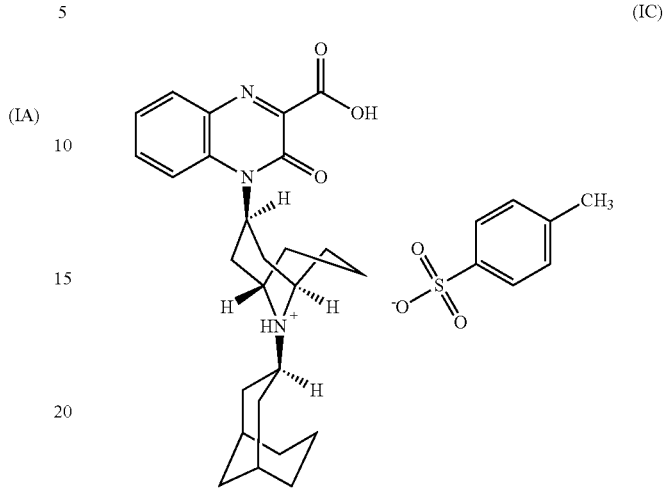

or a solvate thereof.

(5) The method of any one of the above (1)-(4), wherein the Insomnia Disorder is adult insomnia, child insomnia, middle-of-the-night insomnia, insomnia-type alcohol-induced sleep disorder, insomnia in alcohol use disorder, insomnia associated with alcohol cessation, or any combination thereof.

(6) The method of the above (5), wherein the Insomnia Disorder is adult insomnia.

(7) The method of the above (5), wherein the Insomnia Disorder is child insomnia.

(8) The method of the above (5), wherein the Insomnia Disorder is middle-of-the-night insomnia.

(9) The method of the above (5), wherein the Insomnia Disorder is insomnia-type alcohol-induced sleep disorder.

(10) The method of the above (5), wherein the Insomnia Disorder is insomnia in alcohol use disorder.

(11) The method of the above (5), wherein the Insomnia Disorder is insomnia associated with alcohol cessation.

(12) The method of any one of the above (1)-(11), wherein the Insomnia Disorder is treated.

(13) The method of any one of the above (1)-(11), wherein the Insomnia Disorder is prevented.

(14) The method of any one of the above (1)-(12), wherein average sleep efficiency of a human administered a daily dose of the compound or a solvate thereof on two consecutive days is at least about 1.04 times the average sleep efficiency of a human administered a placebo.

(15) The method of any one of the above (1)-(12), wherein average total sleep time of a human administered a daily dose of the compound or a solvate thereof on two consecutive days is at least about 15 minutes greater than the average total sleep time of a human administered a placebo.

(16) The method of any one of the above (1)-(12), wherein average wake after sleep onset (WASO) of a human administered a daily dose of the compound or a solvate thereof on two consecutive days is at least about 20 minutes less than the average WASO of a human administered a placebo.

(17) The method of any one of the above (1)-(12), wherein average amount of time spent in sleep Stage N2 of a human administered a daily dose of the compound or a solvate thereof on two consecutive days is at least about 30 minutes greater than the average amount of time spent in sleep Stage N2 of a human administered a placebo.

(18) The method of any one of the above (1)-(17), wherein the daily dose of the compound or a solvate thereof is from about 0.5 mg to about 3.0 mg.

(19) The method of the above (18), wherein the daily dose of the compound or a solvate thereof is about 3.0 mg.

(20) The method of any one of the above (1)-(18), wherein the daily dose of the compound or a solvate thereof is from about 0.5 mg to about 2.0 mg.

(21) The method of the above (20), wherein the daily dose of the compound or a solvate thereof is about 2.0 mg.

(22) The method of the above (20), wherein the daily dose of the compound or a solvate thereof is about 1.5 mg.

(23) The method of any one of the above (1)-(18), wherein the daily dose of the compound or a solvate thereof is from about 0.5 mg to about 1.0 mg.

(24) The method of the above (23), wherein the daily dose of the compound or a solvate thereof is about 1.0 mg.

(25) The method of the above (23), wherein the daily dose of the compound or a solvate thereof is about 0.75 mg.

(26) The method of the above (23), wherein the daily dose of the compound or a solvate thereof is about 0.5 mg.

(27) The method of any one of the above (1)-(26), wherein administration of the compound or a solvate thereof is by at least one route selected from oral, parenteral, intravenous, intramuscular, intraocular, transdermal, and transmucosal.

(28) The method of any one of the above (1)-(26), wherein the compound or a solvate thereof is orally administered.

(29) The method of the above (28), wherein the compound or a solvate thereof is buccally, gingivally, or sublingually administered or is administered in the form of a swallowed-intact oral dosage form.

(30) The method of the above (28), wherein administration of the compound or a solvate thereof is by a swallowed-intact oral dosage form.

(31) The method of any one of the above (1)-(30), wherein the daily dose is administered from about 60 minutes before the intended bedtime to about the intended bedtime.

(32) The method of any one of the above (1)-(31), wherein the daily dose is a single daily dose.

(33) Use of the compound as defined in any one of the above (1)-(4) or a solvate thereof in the preparation of a medicament for the treatment or prevention of an Insomnia Disorder, wherein a single medicament contains a dose of from about 0.16 mg to about 8.0 mg of the compound or the solvate thereof.

(34) The use of the above (33), wherein the Insomnia Disorder is adult insomnia, child insomnia, middle-of-the-night insomnia, insomnia-type alcohol-induced sleep disorder, insomnia in alcohol use disorder, insomnia associated with alcohol cessation, or any combination thereof.

(35) The use of the above (33), wherein the Insomnia Disorder is adult insomnia.

(36) The use of the above (33), wherein the Insomnia Disorder is child insomnia.

(37) The use of the above (33), wherein the Insomnia Disorder is middle-of-the-night insomnia.

(38) The use of the above (33), wherein the Insomnia Disorder is insomnia-type alcohol-induced sleep disorder.

(39) The use of the above (33), wherein the Insomnia Disorder is insomnia in alcohol use disorder.

(40) The use of the above (33), wherein the Insomnia Disorder is insomnia associated with alcohol cessation.

(41) The use of any one of the above (33)-(40), wherein the Insomnia Disorder is treated.

(42) The use of any one of the above (33)-(40), wherein the Insomnia Disorder is prevented.

(43) The use of any one of the above (33)-(42), wherein the medicament is formulated for administration by at least one route selected from oral, parenteral, intravenous, intramuscular, intraocular, transdermal, and transmucosal.

(44) The use of any one of the above (33)-(42), wherein the medicament is formulated for oral administration.

(45) The use of the above (44), wherein the medicament is formulated for buccal, gingival, or sublingual administration or formulated as a swallowed-intact oral dosage form.

(46) The use of the above (44), wherein the medicament is formulated as an orally disintegrating tablet.

(47) The use of the above (44), wherein the medicament is formulated as a swallowed-intact oral dosage form.

(48) The use of any one of the above (33)-(47), wherein a single medicament contains a dose of from about 0.5 mg to about 6.0 mg of the compound or the solvate thereof.

(49) A pharmaceutical composition for treating or preventing an Insomnia Disorder, comprising a dose of from about 0.16 mg to about 8.0 mg of the compound as defined in any one of the above (1)-(4) or a solvate thereof.

(50) The pharmaceutical composition of the above (49), wherein the Insomnia Disorder is adult insomnia, child insomnia, middle-of-the-night insomnia, insomnia-type alcohol-induced sleep disorder, insomnia in alcohol use disorder, insomnia associated with alcohol cessation, or any combination thereof.

(51) The pharmaceutical composition of the above (50), wherein the Insomnia Disorder is adult insomnia.

(52) The pharmaceutical composition of the above (50), wherein the Insomnia Disorder is child insomnia.

(53) The pharmaceutical composition of the above (50), wherein the Insomnia Disorder is middle-of-the-night insomnia.

(54) The pharmaceutical composition of the above (50), wherein the Insomnia Disorder is insomnia-type alcohol-induced sleep disorder.

(55) The pharmaceutical composition of the above (50), wherein the Insomnia Disorder is insomnia in alcohol use disorder.

(56) The pharmaceutical composition of the above (50), wherein the Insomnia Disorder is insomnia associated with alcohol cessation.

(57) The pharmaceutical composition of any one of the above (49)-(56), wherein the Insomnia Disorder is treated.

(58) The pharmaceutical composition of any one of the above (49)-(56), wherein the Insomnia Disorder is prevented.

(59) The pharmaceutical composition of any one of the above (49)-(58), wherein the composition comprises a dose of from about 0.5 mg to about 6.0 mg of the compound or a solvate thereof.

(60) The pharmaceutical composition of any one of the above (49)-(59), wherein the composition comprises a dose of from about 0.5 mg to about 3.0 mg of the compound or a solvate thereof.

(61) The pharmaceutical composition of the above (60), wherein the composition comprises a dose of about 3.0 mg of the compound or a solvate thereof.

(62) The pharmaceutical composition of any one of the above (49)-(60), wherein the composition comprises a dose of from about 0.5 mg to about 2.0 mg of the compound or a solvate thereof.

(63) The pharmaceutical composition of the above (62), wherein the composition comprises a dose of about 2.0 mg of the compound or a solvate thereof.

(64) The pharmaceutical composition of the above (62), wherein the composition comprises a dose of about 1.5 mg of the compound or a solvate thereof.

(65) The pharmaceutical composition of any one of the above (49)-(60), wherein the composition comprises a dose of from about 0.5 mg to about 1.0 mg of the compound or a solvate thereof.

(66) The pharmaceutical composition of the above (65), wherein the composition comprises a dose of about 1.0 mg of the compound or a solvate thereof.

(67) The pharmaceutical composition of the above (65), wherein the composition comprises a dose of about 0.75 mg of the compound or a solvate thereof.

(68) The pharmaceutical composition of the above (65), wherein the composition comprises a dose of about 0.5 mg of the compound or a solvate thereof.

(69) The pharmaceutical composition of any one of the above (49)-(68), wherein the composition further comprises a pharmaceutically acceptable carrier or excipient.

(70) The pharmaceutical composition of any one of the above (49)-(69), wherein the composition is in unit dosage form suitable for oral administration.

(71) The pharmaceutical composition of the above (70), wherein the unit dosage form is a capsule, a gelcap, a caplet, or a tablet.

(72) The pharmaceutical composition of the above (70), wherein the unit dosage form is an orally disintegrating tablet.

(73) The pharmaceutical composition of the above (70), wherein the unit dosage form is a swallowed-intact tablet.

(74) A compound of Formula (I)

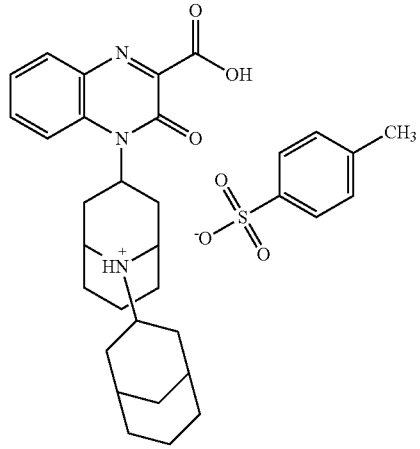

(I)

for use in a method of treating or preventing an Insomnia Disorder, wherein the daily dose is from about 0.5 mg to about 6.0 mg.

(75) A compound of Formula (I)

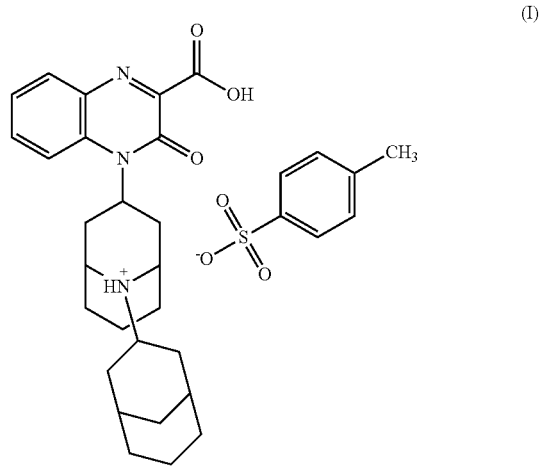

(I)

for use in a method for treating or preventing Insomnia Associated with Alcohol Cessation.

In one embodiment, a compound of formula (I), (IA), (IB), or (IC), or a solvate thereof, demonstrates minimal penetration across the central nervous system ("CNS") blood-brain barrier in an animal. Such minimally-penetrating compounds are referred to as "peripherally restricted". In connection with this tissue selectivity, it is useful to define $K_p$ as the ratio of the quantity of a compound that penetrates across an animal's blood-brain barrier into the CNS (e.g., as determined from the quantity of the compound in a whole brain homogenate) to the quantity of the compound circulating in the animal's plasma.

A compound of formula (I), (IA), (IB), or (IC), or a solvate thereof, can be tested for the ability to penetrate into the CNS using in vitro and in vivo methods known in the art such as, e.g., the in vivo method disclosed in Example 11 of International Application No. PCT/IB2017/054506. Certain compounds of formula (I), (IA), (IB), or (IC), or a solvate thereof, exhibit a reduced propensity to blood-brain barrier penetration as measured by the Madin Darby canine kidney ("MDCK") cell-line transport assay disclosed in, e.g., Wang et al. ("Evaluation of the MDR-MDCK cell line as a permeability screen for the blood-brain barrier," *Int. J. Pharm.* 288(2):349-359 (2005)).

A compound of formula (I), (IA), (IB), or (IC), or a solvate thereof, or composition comprising the same, can be administered to a subject who has alcohol use disorder, and/or who is prone to alcohol abuse. A compound of formula (I), (IA), (IB), or (IC), or a solvate thereof, or composition comprising the same, can be administered to a subject in the presence of alcohol without affecting the pharmacokinetic profile of the compound or ethanol.

A compound of formula (I), (IA), (IB), or (IC), or a solvate thereof, or composition comprising the same, can be administered to a subject who has one or more addictive disorders, including addiction to sedatives or hypnotics.

A compound of formula (I), (IA), (IB), or (IC) exhibits addictive properties that are not statistically greater than placebo at a therapeutic dose level and/or are less than Drug Enforcement Administration ("DEA") Schedule IV substances used to treat insomnia (e.g., triazolam) at a therapeutic dose level or at a supratherapeutic dose level (e.g., a dose that is at least 5 times the therapeutic dose).

A compound of formula (I), (IA), (IB), or (IC), when administered at a therapeutic dose, exhibits one or more adverse events, selected from, ataxia, dizziness, hiccups, amnesia, headache, diplopia, blurred vision, nausea, and euphoric mood at about the same rate as placebo and/or a lower rate than other medicaments used to treat insomnia (e.g., triazolam) administered at therapeutic doses. A compound of formula (I), (IA), (IB), or (IC), when administered at a supratherapeutic dose (e.g., a dose that is at least 5 times the therapeutic dose), exhibits one or more adverse events, selected from, ataxia, dizziness, hiccups, amnesia, headache, diplopia, blurred vision, nausea, and euphoric mood at about the same rate as placebo and/or at a lower rate than other medicaments used to treat insomnia (e.g., triazolam) administered at therapeutic doses.

A compound of formula (I), (IA), (IB), or (IC) is minimally metabolized by the liver. This is advantageous, because liver damage is common in populations with alcohol use disorder. Accordingly, a compound of formula (I), (IA), (IB), or (IC), or a solvate thereof, or composition comprising the same, addresses the need for a medicament to treat insomnia associated with alcohol cessation without adversely impacting liver function.

A compound of formula (I), (IA), (IB), or (IC), or a solvate thereof, or composition comprising the same can be administered to subjects who have hepatic impairment resulting from any cause, including liver disease related to alcohol consumption. A compound of formula (I), (IA), (IB), or (IC), or a solvate thereof, or composition comprising the same, can be administered to a human diagnosed as having hepatic impairment at the same daily dose as administered to a human who has not been diagnosed as having hepatic impairment, e.g., a human who does not have hepatic impairment.

A compound of formula (I), (IA), (IB), or (IC), or a solvate thereof, or composition comprising the same, can be administered to a patient who is receiving one or more concomitant therapy(ies) for treating or preventing addictive alcohol use disorder. In an embodiment, a concomitant therapy for treating or preventing alcohol use disorder is selected from disulfiram, naltrexone, acamprosate, gabapentin, topiramate, nalmefene, naloxone, fluoxetine, quetiapine, and combinations thereof.

5.1 Stages of Sleep

Mammalian sleep can be divided into two distinct types: non-rapid eye movement ("NREM") sleep and rapid eye movement ("REM") sleep. NREM sleep is further divided into a series of distinct stages generally referred to as Stages N1 through N3. Stage N1 or light sleep is generally viewed as the transition between being awake and being asleep. Stage N1 is characterized by a slowing in breathing and heart rate during the transition from being awake to being asleep. Stage N2 or true sleep typically follows Stage N1, is considered as baseline sleep and, ideally, occupies roughly at least half of the time asleep. Stage N2 is characterized by muscle relaxation, reduced or limited eye movement, and reduced or limited body movement. Stage N3 is referred to as "delta" or "slow wave" sleep and is generally recognized to be the deepest and most restorative stage of sleep. Stage N3 is characterized by additional slowing of breathing and heart rate. Arousal from Stage N3 can be difficult.

REM sleep, sometimes referred to as dream sleep, consists of an active stage of sleep with characteristic rapid eye movements as the sleeper has vivid dreams. REM sleep is recognized as a separate sleep type because of its more distinct reduction of muscle tone and no body movement; however, breathing and heart rate may increase and become irregular during REM sleep.

Each of these sleep types and stages has a telltale EEG pattern and, over a single night of sleep a sleeper will generally cycle through these types and stages a number of times. Each 30 second unit of time over the course of sleep can be referred to as an "epoch" and, based on the EEG pattern obtained during sleep, a sleep technologist is able to assign a sleep type and/or stage (or an awake designation) to each such epoch.

5.2 Sleep Disorders

As noted above, under one classification scheme six broad categories of sleep disorders have been identified: (i) insomnia, (ii) hypersomnia, (iii) parasomnia, (iv) circadian rhythm sleep-wake disorders, (v) sleep-related breathing disorders, and (vi) sleep movement disorders. Multiple subcategories are recognized within each of these broad categories. Each category and subcategory is defined as a "Disorder". As used herein, "Insomnia Disorder" involves the inability to fall asleep or to stay asleep. Insomnia Disorder includes insomnia ("adult insomnia"), i.e., the inability of an adult to fall asleep at the desired intended bedtime; child insomnia, i.e., the inability of a child (i.e., a human age 12 and below) to fall asleep at the intended bedtime, e.g., because of a refusal to go to bed or reluctance to allow a parent to leave the bedside; and middle-of-the-night insomnia (or "MOTN insomnia"), i.e., waking up in the middle of the night followed by difficulty in resuming sleep, also sometimes known as sleep maintenance insomnia, middle insomnia, middle-of-the-night awakening (or "MOTN awakening"), and/or nocturnal awakening. As used herein, "adult insomnia", also sometimes known as sleep-onset insomnia, insomnia disorder, "primary insomnia", or early insomnia, is used to distinguish from the nonspecific term insomnia. Adult insomnia is not brought about by a disease or the use/abuse of a substance. Adult insomnia can be assessed through the prolongation of LPS. MOTN insomnia can be assessed through the prolongation of WASO and/or increased number of awakenings ("NAW").

As also noted above, under another classification scheme ten broad primary categories of sleep disorders have been identified: (1) insomnia disorder, (2) hypersomnolence disorder, (3) narcolepsy, (4) breathing-related sleep disorders, (5) circadian rhythm sleep-wake disorders, (6) non-REM sleep arousal disorders, (7) nightmare disorder, (8) REM sleep behavior disorder, (9) restless leg syndrome, and (10) substance/medication-induced sleep disorder. Multiple subcategories are recognized within each of these broad categories. Each category and subcategory is also defined as a "Disorder". For example, the Disorder substance/medication-induced sleep disorder involves a prominent sleep disturbance that is sufficiently severe to warrant independent clinical attention and that is judged to be primarily associated with the pharmacological effects of a substance, e.g., alcohol (i.e., ethyl alcohol). The Disorder substance/medication-induced sleep disorder includes insomnia-type substance/medication-induced sleep disorder, daytime sleepiness type substance/medication-induced sleep disorder, parasomnia type substance/medication-induced sleep disorder, and mixed type substance/medication-induced sleep disorder. The mixed type relates to more than one type of these sleep disturbance-related symptoms being present but none predominating. Thus, a Disorder that can be treated and/or prevented includes alcohol-induced sleep disorder and any/all of its subcategories: insomnia-type alcohol-induced sleep disorder, daytime sleepiness type alcohol-induced sleep disorder, parasomnia type alcohol-induced sleep disorder, and mixed type alcohol-induced sleep disorder. In alcohol-induced sleep disorder, there is evidence of intoxication or withdrawal from the alcohol and the sleep disorder is associated with intoxication, discontinuation, or withdrawal therefrom. Other allied Disorders that can be treated and/or prevented include insomnia in alcohol use disorder, sleep disturbances associated with alcohol cessation, and/or insomnia associated with alcohol cessation.

Thus, as used herein "Insomnia Disorder" also includes insomnia-type alcohol-induced sleep disorder, mixed type alcohol-induced sleep disorder which includes insomnia-type alcohol-induced sleep disorder as a component, insomnia in alcohol use disorder, and insomnia associated with alcohol cessation.

There remains an unmet need for a safe and effective medication to treat and/or prevent an Insomnia Disorder, e.g., adult insomnia, child insomnia, MOTN insomnia, insomnia-type alcohol-induced sleep disorder, insomnia in alcohol use disorder, and/or insomnia associated with alcohol cessation.

5.2 Insomnia Associated with Alcohol Cessation

Alcohol use disorder is characterized by heavy alcohol consumption that causes dysfunction in motivational, mood-stress regulation and sleep systems that interact in complex ways to heighten the risk of relapse during abstinence. Emerging data suggest that excessive and chronic alcohol use disrupts the sleep homeostat. Additionally, in abstinence, subjects with alcohol use disorder are known to experience insomnia that may persist for weeks to years, referred to as insomnia associated with alcohol cessation.

In connection with alcohol-related sleep disorders, DSM-5 also sets out alcohol-induced sleep disorder as a principal diagnosis and subdivides the sleep disorder into four types: insomnia, daytime sleepiness, parasomnia, and mixed type. It discloses that alcohol-induced sleep disorder typically occurs as "insomnia type", that is, sleep disorder characterized by "difficulty falling asleep or maintaining sleep, frequent nocturnal awakenings, or nonrestorative sleep." Specifically, Conroy 2006 discloses alcohol consumption has a "biphasic" effect on sleep within a night. That is, in the earlier portion of the night an alcohol dose can provide an immediate sedative effect with shorter LPS and an increased duration of Stage N3 sleep. However, in the later portion of the night sleep quality deteriorates and there is a greater NAW. Yet another reference concludes that virtually every type of sleep problem occurs in alcohol-dependent patients, typically, a long LPS, low SE, short TST, reduced duration of Stage N3 sleep, fragmented sleep patterns, and severely disrupted sleep architecture (Landolt et al., "Sleep Abnormalities During Abstinence in Alcohol-Dependent Patients: Aetiology and Management," *CNS Drugs* 15(5):413-425 (2001)).

Insomnia associated with alcohol cessation can be distinguished from insomnia in the general population. Insomnia associated with alcohol cessation differs from insomnia disorder in terms of the underlying neuropathophysiology. Data from electroencephalogram (EEG) spectral analysis, the Multiple Sleep Latency Test, event-related brain potentials, and neuroimaging studies suggest that insomnia disorder may be a 24-hour disorder of hyperarousal, which involves activation of the sympathetic nervous system and the hypothalamic-pituitary-adrenal axis, corticotropin-releasing hormone/norepinephrine activation, and dopaminergic pathways in the brain. (See, e.g., Roehrs, T., Gumenyuk, V., Drake, C., Roth, T., 2014. "Physiological correlates of insomnia." *Curr Top Behav Neurosci.* 21, 277-290; Roehrs, T. A., Roth, T., 2015. "Sleep Disturbance in Substance Use Disorders." *Psychiatr Clin North Am.* 38(4), 793-803.

Insomnia associated with alcohol cessation can be characterized as insomnia or the worsening of insomnia that occurs after a person with alcohol use disorder abstains from alcohol consumption.

For example, a subject may not experience insomnia prior to alcohol abuse, then the subject engages in alcohol abuse that leads to alcohol use disorder, and then after abstaining from alcohol the subject experiences insomnia associated with alcohol cessation.

In another example, a subject may not experience insomnia prior to alcohol abuse, then the subject engages in alcohol abuse that leads to alcohol use disorder and the subject begins to experience insomnia-type alcohol-induced sleep disorder, and then after abstaining from alcohol the subject experiences insomnia associated with alcohol cessation.

In another example, a subject may experience insomnia prior to alcohol abuse, then the subject engages in alcohol abuse that leads to alcohol use disorder, and after abstaining from alcohol the subject experiences insomnia associated with alcohol cessation that is more severe than the insomnia the subject experienced prior to experiencing alcohol use disorder.

In another example, a subject may experience insomnia prior to alcohol abuse, then the subject engages in alcohol abuse that leads to alcohol use disorder such that the subject begins to experience insomnia-type alcohol-induced sleep disorder that includes worsening of insomnia, and after abstaining from alcohol the subject experiences insomnia associated with alcohol cessation that is more severe than the insomnia the subject experienced prior to experiencing alcohol use disorder.

Insomnia associated with alcohol cessation commonly occurs in the acute withdrawal phase (1 to 2 weeks), early recovery (2 to 8 weeks after detoxification), and in sustained recovery (3 or more months after the detoxification phase). In the acute withdrawal phase, sleep disturbances are variable and can improve over the detoxification period. During the early recovery phase, sleep-related disturbances may be accompanied by mild withdrawal symptoms, such as mood changes and alcohol craving, and can persist up to 5 weeks. During sustained recovery, sleep-related disturbances can persist up to 3 years or more. (See, e.g., Chakravorty, S., Chaudhary, N. S., Brower, K. J., 2016. "Alcohol Dependence and Its Relationship With Insomnia and Other Sleep Disorders." *Alcohol Clin Exp Res.* 40(11), 2271-2282.)

Even alcoholics who have been abstinent, either for short periods of time (several weeks) or extended periods of time (several years), can experience persistent sleep abnormalities such as increased LPS, frequent MOTN awakening, and poor sleep quality. In summarizing the results of multiple studies, Brower 2001 concludes that alcoholics who had been abstinent for 2-8 weeks exhibited worse sleep than did non-alcoholics, that is, TST, SE, and the amount of time spent in Stage N3 sleep generally decreased significantly whereas Stage N1 sleep time usually increased and LPS increased significantly. Moreover, sleep abnormalities can persist for 1-3 years after alcohol consumption ends. For example, Brower 2001 concludes that sleep fragmentation, expressed as increases in sleep-stage changes, brief arousals, and REM sleep disruptions, can persist for 1-3 years after establishing sobriety. Diminished REM sleep time is understood to be associated with negative cognitive consequences, e.g., poor procedural learning.

Moreover, it is recognized that the consumption of alcohol can damage the human liver, a vital organ that filters harmful substances from the blood and manufactures various substances, such as hormones, proteins, and enzymes, that the body requires. Alcohol-related liver disease ("ALD") is caused by excessive consumption of alcohol. Its mildest form, steatosis or fatty liver, is characterized by an excessive accumulation of fat inside liver cells, making liver functioning more difficult. A more severe form of ALD that can develop from steatosis is alcoholic hepatitis, either chronic or acute. It manifests as the inflammation or swelling of the liver accompanied by the destruction of liver cells and makes liver functioning even more difficult. The most severe form of ALD that can develop from excess alcohol consumption is alcoholic cirrhosis. It is characterized by the replacement of normal liver tissue with nonliving scar tissue. Alcoholic cirrhosis can be a life-threatening disease because of the associated severe impairment of liver functioning.

Many researchers have concluded that untreated sleep disturbances can contribute to the risk of alcohol relapse after a period of abstinence and that disturbed sleep is an important predictor of relapse (See, e.g., Arnedt, J. T., Conroy, D. A., Brower, K. J., 2007. "Treatment options for sleep disturbances during alcohol recovery." *J Addict Dis.* 26(4), 41-54; Miller, M. B., Donahue, M. L., Carey, K. B., Scott-Sheldon, L. A. J., 2017. "Insomnia treatment in the context of alcohol use disorder: A systematic review and meta-analysis." *Drug and alcohol dependence*. 181, 200-207; Roehrs, T., Roth, T., 2008 "Sleep and quality of life in medical illnesses," in: Verster, J. C., Pandi-Perumal, S. R., Streiner, D. L. (Eds.), *Sleep, alcohol, and quality of life*. Humana Press, Totowa, N.J., pp. 333-339.) Subjective and objective indicators of sleep disturbances that have been evaluated in alcohol-dependent patients after the acute abstinence period, such as difficulty in falling asleep, decreased total sleep time, and decreased sleep efficiency, predict the likelihood of relapse during longer periods of abstinence. (Arnedt et al., 2007; Koob, G. F., 2008. "A role for brain stress systems in addiction." *Neuron*. 59(1), 11-34.; Roehrs, T., Roth, T., 2017. "Principles and practice of sleep medicine," in: Kryger, M. H., Roth, T., Dement, W. C. (Eds.), *Medication and substance abuse*. Elsevier, Philadelphia, Pa., pp. 1380-1389; Roehrs and Roth, 2015).

In an early polysomnography study, Drummond et al. (1998) showed that persistently abnormal recordings of eye-movement density in REM sleep and REM latency in primary alcohol-dependent inpatients at 14 months were associated with alcohol relapse. Other relapse predictors in this study were an increase in sleep-onset latency, a reduction in the percentage of SWS, and a reduction in sleep efficiency. These researchers determined that persistent insomnia and sleep fragmentation after 5 months of abstinence predicted relapse over 14 months of sustained abstinence. (Drummond, S. P., Gillin, J. C., Smith, T. L., DeModena, A., 1998. "The sleep of abstinent pure primary alcoholic patients: natural course and relationship to relapse." *Alcohol Clin Exp Res*. 22(8), 1796-1802; Kolla, B. P., Bostwick, J. M., 2011. Insomnia: The neglected component of alcohol recovery." *J Addict Res Ther*. 2(0e2)).

Thus, there remains an unmet need for a safe and effective medication to treat sleep disorders or disturbances, e.g., adult insomnia, that are associated with alcohol use disorder, alcohol dependence, alcohol-induced sleep disorder, and/or alcohol cessation. In one desirable embodiment, such medication would function effectively even when the liver suffers from alcohol-induced damage in the form of steatosis, alcoholic hepatitis, and/or alcoholic cirrhosis. In another desirable embodiment, such medication would be administered at therapeutically effective dosages without significant risk of addiction to the medication.

5.3 ORL-1 Expression

Examples of tissue comprising cells capable of expressing the ORL-1 receptor include but are not limited to brain, spinal cord, vas deferens, and gastrointestinal tract tissue. Methods for assaying cells that express the ORL-1 receptor are known in the art; for example, see Shimohigashi et al., "Sensitivity of Opioid Receptor-like Receptor ORL1 for Chemical Modification on Nociceptin, a Naturally Occurring Nociceptive Peptide," *J. Biol. Chem.* 271(39):23642-23645 (1996); Narita et al., "Identification of the G-protein Coupled ORL1 Receptor in the Mouse Spinal Cord by [$^{35}$S]-GTPγS Binding and Immunohistochemistry," *Brit. J. Pharmacol.* 128:1300-1306 (1999); Milligan, "Principles: Extending the Utility of [$^{35}$S]GTPγS Binding Assays," *TIPS* 24(2):87-90 (2003); and Lazareno, "Measurement of Agonist-stimulated [$^{35}$S]GTPγS Binding to Cell Membranes," *Methods in Molecular Biology* 106:231-245 (1999).

It is known that mammalian species display differences in ORL-1 receptor expression. For example, in the nucleus accumbens and caudate putamen, rodents have relatively low levels of ORL-1 receptor expression (Florin et al., "Autoradiographic localization of [$^3$H]nociceptin binding sites in the rat brain," *Brain Res.* 880:11-16 (2000); Neal et al., "Opioid receptor-like (ORL1) receptor distribution in the rat central nervous system: Comparison of ORL1 receptor nRNA expression with $^{125}$I-[14Tyr]-orphanin FQ binding," *J. Compar. Neurol.* 412(4):563-605 (1999)). In contrast, monkeys and humans have moderate to high levels of expression in these regions (Bridge et al., "Autoradiographic localization of $^{125}$I[$^{14}$Tyr] nociceptin/orphanin FQ binding sites in Macaque primate CNS," *Neurosci.* 118:513-523 (2003); Berthele et al., "[3H]-Nociceptin ligand-binding and nociception opioid receptor nRNA expression in the human brain," *Neurosci.* 121:629-640 (2003)). In another example, rodents have relatively low levels of ORL-1 receptor expression in the cerebellar cortex, while monkeys and humans have moderate to high levels of expression in these regions. Moreover, rodents have relatively low levels of expression of ORL-1 in lamina I and II of the prefrontal cortex ("PFC"), while humans have moderate to high levels of expression in lamina I and II of the PFC. Thus, references such as those above disclose notable supra-spinal species differences in ORL-1 expression and protein localization, which may be of physiological consequence.

It is well known that one of the nuclei of the brain's hypothalamus, the SCN, is the master controller of the sleep cycle in humans (Richardson, "The Human Circadian System in Normal and Disordered Sleep," *J. Clin. Psychiatry* 66(Suppl. 9):3-9 (2005)). The SCN is made up of a network of nerve cells that fire together with the circadian rhythm. When injected unilaterally into the SCN of Syrian hamsters, nociceptin, the endogenous ligand of the ORL-1 receptor, modulated the activity of SCN neurons and the response of the circadian clock to light (Allen et al., *J. Neurosci.* 19(6):2152-2160 (1999)). An ORL-1 agonist (W-212393) induced a phase advance in the circadian body temperature rhythm of rats by suppression of rhythmic firing of SCN neurons (Teshima et al., *Br. J. Pharmacol.* 146(1):33-40

(2005)). These references demonstrate that modulating the ORL-1 receptor in the brain can influence circadian-related processes such as, e.g., sleep.

It is also recognized that portions of the hypothalamus are only partially protected by the blood-brain-barrier (De la Torre, *J. Neurol. Sci.* 12(1):77-93 (1971)). While not wishing to be bound by theory, it is possible that a compound of formula (I), (IA), (IB), or (IC), or a solvate thereof, is able to gain access to the SCN or other related nuclei in humans, stimulate ORL-1 receptors therein, and produce fatigue and/or somnolence via modulation of the rhythmic firing pattern of the SCN neurons or other related nuclei.

According to the present disclosure, some compounds of formula (I), (IA), (IB), or (IC), or a solvate thereof, are partial agonists at the human ORL-1 receptor. In another embodiment, a compound of formula (I), (IA), (IB), or (IC), or a solvate thereof, is a partial agonist at the human ORL-1 receptor and an antagonist at a human mu, kappa, and/or delta opioid receptor. In another embodiment, a compound of formula (I), (IA), (IB), or (IC), or a solvate thereof, is a partial agonist at the human ORL-1 receptor and an antagonist at the human opioid receptor.

5.4 Definitions

As used in connection with the compounds of formula (I), (IA), (IB), (IC) and their solvates and their methods of use, the terms used herein have the following meanings.

The term "Time in Bed" ("TIB") refers to the duration of time, e.g., in minutes, of an entire intended sleep episode from its beginning to its end. TIB is often of a fixed duration, e.g., 480 minutes.

The beginning of the TIB is, for the purposes herein, the "intended bedtime".

The term "Total Sleep Time" ("TST") refers to the sum of all time epochs, e.g., in minutes, spent in either NREM (including all of Stages N1 through N3) or REM sleep.

The term "Sleep Efficiency" ("SE") is measured by polysomnography in insomnia subjects and refers to the fraction of the TIB that is spent asleep in REM and NREM sleep and is calculated as the following ratio: TST/TIB. Alternately, SE can be expressed as a percentage by multiplying this ratio by 100. SE is a measure of sleep maintenance throughout the night, thus, assessment of SE also includes, inter alia, assessment of prolonged LPS and/or assessment of prolonged WASO.

The term "Latency to Persistent Sleep" ("LPS") refers to the time, e.g., in minutes, from the beginning of the TIB until the start of a period of least 10 uninterrupted minutes of sleep epochs—in any sleep stage. LPS is a measure of the "speed" of going to sleep.

The term "Wake During Sleep" ("WDS") refers to the total time, e.g., in minutes, of epochs spent awake occurring after the onset of persistent sleep (defined as at least 10 consecutive minutes of sleep epochs of any sleep stage) and before the onset of the final epoch of sleep (of any sleep stage) during the TIB.

The term "Wake After Sleep" ("WAS") refers to the duration, e.g., in minutes, of time spent awake after the conclusion of final sleep epoch (of any sleep stage) until the end of the TIB.

The term "Wake After Sleep Onset" ("WASO") refers to the sum of WDS and WAS. WASO is another measure of sleep maintenance throughout the night.

The term "Number of Awakenings" ("NAW") refers to the number of times after onset of persistent sleep in which an awakening for a period of greater than 30 seconds occurs.

The term "REM latency" refers to the time, e.g., in minutes, from the beginning of the TIB until the beginning of the first epoch of REM sleep.

The term "animal" includes, but is not limited to, a human or a non-human mammal, such as a companion animal or livestock, e.g., a cow, monkey, baboon, chimpanzee, horse, sheep, pig, chicken, turkey, quail, cat, dog, mouse, rat, rabbit or guinea pig. In one embodiment, an animal is a human.

The term "pharmaceutically acceptable salt", as used herein, is any pharmaceutically acceptable salt that can be prepared from a compound including a salt formed from an acid and a basic functional group, such as a nitrogen group, of the compound. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a compound having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines, such as N-methyl-N-ethylamine, diethylamine, triethylamine, tributyl amine, (tert-butylamino)methanol, and tris-(hydroxymethyl)amine; dicyclohexylamine; pyridine; picoline; mono-, bis-, or tris-(2-hydroxy-($C_1$-$C_3$)alkyl amines), such as mono-, bis-, or tris-(2-hydroxyethyl)amine, and N,N-di-[($C_1$-$C_3$)alkyl]-N-(hydroxy-($C_1$-$C_3$)alkyl)-amines, such as N,N-dimethyl-N-(2-hydroxyethyl)amine; N-methyl-D-glucamine; an amino acid, such as arginine and lysine; an amino acid derivative, such as choline (i.e., 2-hydroxy-N,N,N-trimethylethan-1-aminium), a derivative of the amino acid serine; and the like. In one embodiment, the pharmaceutically acceptable salt is a hydrochloride salt, a sulfate salt, a sodium salt, a potassium salt, a benzene sulfonic acid salt, a para-toluenesulfonic acid salt, or a fumaric acid salt. In another embodiment, the pharmaceutically acceptable salt is a hydrochloride salt or a sulfate salt. In another embodiment, the pharmaceutically acceptable salt is a hydrochloride salt. In another embodiment, the pharmaceutically acceptable salt is a sulfate salt. In another embodiment, the pharmaceutically acceptable salt is a sodium salt. In another embodiment, the pharmaceutically acceptable salt is a potassium salt. In another embodiment, the pharmaceutically acceptable salt is a fumaric acid salt. In another embodiment, the pharmaceutically acceptable salt is a para-toluenesulfonic acid salt. In another embodiment, the pharmaceutically acceptable salt is a choline salt.

The term "concomitant therapy" is defined to include all medications (over-the-counter (OTC)) and/or prescription medications, procedures, and significant nonpharmacological therapies that are used to treat a subject during the time periods relevant to administration of the compound of formula (I), (IA), (IB), or (IC). In an embodiment, the concomitant therapy may include an agent for treating or preventing an alcohol use disorder.

In another embodiment, the compound of formula (I), (IA), (IB), or (IC) contains one equivalent of the free base of the compound of formula (I), (IA), (IB), or (IC), i.e., the compound of formula (I), (IA), (IB), or (IC), respectively, without para-toluenesulfonic acid being present, and about 1.0 equivalent of para-toluenesulfonic acid, e.g., from about 0.8 to about 1.2 equivalents of para-toluenesulfonic acid in one embodiment or from about 0.9 to about 1.1 equivalents, from about 0.93 to about 1.07 equivalents, from about 0.95 to about 1.05 equivalents, from about 0.98 to about 1.02 equivalents, or from about 0.99 to about 1.01 equivalents of para-toluenesulfonic acid in other embodiments. In another embodiment, the compound of formula (I), (IA), (IB), or (IC) contains 1.0 equivalent of the free base of the compound of formula (I), (IA), (IB), or (IC) and 1.0 equivalent of para-toluenesulfonic acid, i.e., is a mono-tosylate salt.

The methods of the disclosure provided herein also encompass the use of any solvate of the compounds of formula (I), (IA), (IB), and (IC). "Solvates" are generally known in the art, and are considered herein to be a combination, physical association, and/or solvation of a compound of formula (I), (IA), (IB), or (IC) with a solvent molecule. This physical association can involve varying degrees of ionic and covalent bonding, including hydrogen bonding. When the solvate is of the stoichiometric type, there is a fixed ratio of the solvent molecule to the compound of formula (I), (IA), (IB), or (IC), e.g., a di-solvate, mono-solvate, or hemi-solvate when the [solvent molecule]:[compound of formula (I), (IA), (IB), or (IC)] molar ratio is 2:1, 1:1, or 1:2, respectively. In other embodiments, the solvate is of the non-stoichiometric type. For example, the compound of formula (I), (IA), (IB), or (IC) crystal can contain solvent molecules in the structural voids, e.g., channels, of the crystal lattice. In certain instances, the solvate can be isolated, for example, when one or more solvent molecules are incorporated into the crystal lattice of a crystalline solid. Thus, "solvate", as used herein, encompasses both solution-phase and isolatable solvates.

A compound of formula (I), (IA), (IB), or (IC) of the disclosure can be present as a solvated form with a pharmaceutically acceptable solvent, such as water, methanol, ethanol, and the like, and it is intended that the disclosure include both solvated and unsolvated forms of a compound of formula (I), (IA), (IB), and (IC). As "hydrate" relates to a particular subgroup of solvates, i.e., where the solvent molecule is water, hydrates are included within the solvates of the disclosure. In one embodiment, the compound of formula (I), (IA), (IB), or (IC) is present as a mono-hydrate, e.g., where the water:[compound of formula (I), (IA), (IB), or (IC)] molar ratio is about 1:1, e.g., from 0.91:1 to 1.09:1 in one embodiment or from 0.94:1 to 1.06:1, from 0.97:1 to 1.03:1, or from 0.985:1 to 1.015:1 in other embodiments, each said embodiment taking no account of surface water that might be present, if any.

Solvates can be made according to known techniques in view of the present disclosure. For example, Caira et al., "Preparation and Crystal Characterization of a Polymorph, a Mono-hydrate, and an Ethyl Acetate Solvate of the Antifungal Fluconazole," *J. Pharmaceut. Sci.*, 93(3):601-611 (2004), describes the preparation of solvates of fluconazole with ethyl acetate and with water. Similar preparations of solvates, hemi-solvate, hydrates, and the like are described by Van Tonder et al., "Preparation and Physicochemical Characterization of 5 Niclosamide Solvates and 1 Hemisolvate," *AAPS Pharm. Sci. Tech.*, 5(1):Article 12 (2004), and Bingham et al., "Over one hundred solvates of sulfathiazole," *Chem. Comm.*, pp. 603-604 (2001). In one embodiment, a non-limiting, process involves dissolving the compound of formula (I), (IA), (IB), or (IC) in a desired amount of the solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

A compound of formula (I), (IA), or (IB) or a solvate thereof can contain one or more asymmetric centers and can thus give rise to enantiomers, diastereomers, and other stereoisomeric forms. Unless specifically otherwise indicated, the disclosure encompasses compounds with all such possible forms as well as their racemic and resolved forms, and all mixtures thereof. Unless specifically otherwise indicated, all "tautomers", e.g., lactam-lactim, urea-isourea, ketone-enol, amide-imidic acid, enamine-imine, amine-imine, and enamine-enimine tautomers, are intended to be encompassed by the disclosure as well.

As used herein, the terms "stereoisomer", "stereoisomeric form", and related terms as used herein are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule. Optical isomers of a compound of formula (I), (IA), or (IB) can be obtained by known techniques such as chiral chromatography or formation of diastereomeric salts from an optically active acid or base.

Optical purity can be stated in terms of enantiomeric excess ("% ee") and/or diastereomeric excess (% de), each which is determined by the appropriate formula below:

$$\% \ ee = \left[\frac{\text{major enantiomer(mol)} - \text{minor enantiomer(mol)}}{\text{major enantiomer(mol)} + \text{minor enantiomer(mol)}}\right] \times 100\%$$

$$\% \ de = \left[\frac{\text{major diastereomer(mol)} - \text{minor diastereomer(mol)}}{\text{major diastereomer(mol)} + \text{minor diastereomer(mol)}}\right] \times 100\%.$$

The term "effective amount", when used in connection with methods for treating or preventing a sleep disorder by administering a compound of formula (I), (IA), (IB), or (IC), or a solvate thereof, refers to an amount of the compound administered to an animal that provides a therapeutic effect.

The term "effective amount", when used in connection with a second therapeutic agent means an amount for providing the therapeutic effect of the second therapeutic agent.

The terms "modulate", "modulating", and related terms as used herein with respect to the ORL-1 receptor mean the mediation of a pharmacodynamic response (e.g., adult insomnia) in an animal from (i) inhibiting or activating the receptor, or (ii) directly or indirectly affecting the normal regulation of the receptor activity. Compounds that modulate the receptor activity include agonists, partial agonists, antagonists, mixed agonists/antagonists, mixed partial agonists/antagonists, and compounds which directly or indirectly affect regulation of the receptor activity.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compound that binds to a receptor but produces no regulatory effect, but rather blocks binding of another agent to the receptor is defined as an "antagonist". (See Ross et al., "Pharmacodynamics: Mechanisms of Drug Action and the Relationship Between Drug Concentration and Effect," in *Goodman and Gilman's The Pharmacological Basis of Therapeutics* pp. 31-43 (Goodman et al., eds., 10$^{th}$ Ed., McGraw-Hill, New York 2001)).

The terms "treatment of", "treating", and related terms as used herein include the amelioration, reduction, slowing, or cessation of a Disorder or a symptom thereof by administration of an effective amount of a compound of formula (I), (IA), (IB), or (IC), or a solvate thereof. In some embodiments, treating includes inhibiting, for example, decreasing the overall frequency of episodes of a Disorder or a symptom thereof or reducing the severity of a Disorder or a symptom thereof.

The terms "prevention of", "preventing", and related terms as used herein include the avoidance of the onset of a Disorder or a symptom thereof by administration of an effective amount of a compound of formula (I), (IA), (IB), or (IC), or a solvate thereof.

A "disorder" includes, but is not limited to, the Disorders defined herein. In one embodiment, a disorder relates to a Disorder or symptom of insufficient sleep, or resulting from insufficient sleep, or difficulty falling asleep or staying asleep, e.g., an Insomnia Disorder.

The amount by weight of the administered "dose", "dosage", and related terms as used herein refers to the free acid and free base form of a compound of formula (I), (IA), (IB), or (IC), i.e., the no-salt form. By way of example, a 10.00 mg dose of the compound of formula (IC), i.e., the monotosylate salt (1:1 by moles of para-toluenesulfonic acid: free base of compound of formula (IC)), means that 13.93 mg of said compound is actually administered, which 13.93 mg provides 10.00 mg of the no-salt form of the compound of formula (IC) (0.0229 mmoles) and 3.93 mg of para-toluenesulfonic acid (0.0229 mmoles). Likewise, if a solvate of a compound of formula (I), (IA), (IB), or (IC) is administered, the amount by weight of the administered "dose", "dosage", and related terms as used herein refers to the free acid, free base, and non-solvated form of a compound of formula (I), (IA), (IB), or (IC). By way of example, a 10.00 mg dose of the dihydrate of compound of formula (IC) means that 14.75 mg of said compound is actually administered, which 14.75 mg provides 10.00 mg of the no-salt form of the compound of formula (IC) (0.0229 mmoles), 3.93 mg of para-toluenesulfonic acid (0.0229 mmoles), and 0.82 mg of water (0.0458 mmoles).

The term "UI" means urinary incontinence. The term "IBD" means inflammatory-bowel disease. The term "IBS" means irritable-bowel syndrome. The term "ALS" means amyotrophic lateral sclerosis.

The term "SD" as used herein means standard deviation. The term "LSM" as used herein means least-squares mean. The term "STDE" as used herein means standard error.

The term "N/A" as used herein means not applicable.

In the event of doubt as to the agreement of a depicted chemical structure and a chemical name, the chemical name governs.

It is appreciated that various features of the disclosure which are, for clarity, described in the context of separate embodiments, can also be provided in combination in a single embodiment unless otherwise specifically herein excluded. Conversely, various features of the disclosure which are, for brevity, described in the context of a single embodiment, can also be provided separately and/or in any suitable subcombination unless otherwise specifically herein excluded.

5.5 Therapeutic/Prophylactic Uses of the Compound of Formula (I), (IA), (IB), and (IC)

In accordance with the disclosure, the compounds of formula (I), (IA), (IB), and (IC), or a solvate thereof, are administered to an animal in need of treatment or prevention of an Insomnia Disorder. In certain embodiments, the animal is a human.

In one embodiment, an effective amount of a compound of formula (I), (IA), (IB), or (IC), or a solvate thereof, can be used to treat or prevent a sleep disorder treatable or preventable by modulating the activity of the ORL-1 receptor.

An effective amount of a compound of formula (I), (IA), (IB), or (IC), or a solvate thereof, can be used to treat or prevent a sleep disorder including, but not limited to insomnia, such as "adult" insomnia, child insomnia, and middle-of-the-night insomnia; hypersomnia, such as insufficient sleep syndrome; circadian rhythm sleep-wake disorder, such as delayed sleep-wake phase, advanced sleep-wake phase, irregular sleep-wake rhythm, non-24-hour sleep-wake rhythm, shift work syndrome, and jet lag; or any combination thereof. Other sleep disorders that can be treated or prevented by a compound of formula (I), (IA), (IB), or (IC), or a solvate thereof, include types of dyssomnia not already referenced in this paragraph, food allergy insomnia, alcohol-dependent sleep disorder, and/or alcohol-induced sleep disorder.

In an embodiment, a compound of formula (I), (IA), (IB), and (IC), or a solvate thereof, is administered to an animal in need of treatment or prevention of insomnia associated with alcohol cessation. In certain embodiments, the animal is a human.

The disclosure also relates to methods for activating ORL-1 receptor function in a cell, comprising contacting a cell capable of expressing the ORL-1 receptor with an amount of a compound of formula (I), (IA), (IB), or (IC), or a solvate thereof, effective to activate ORL-1 receptor function in the cell. This method can be adapted for use in vitro as part of an assay to select compounds useful for treating or preventing a sleep disorder. Alternatively, the method can be adapted for use in vivo (i.e., in an animal such as a human), by contacting a cell in the animal with an effective amount of a compound of formula (I), (IA), (IB), or (IC), or a solvate thereof. In one embodiment, the method is useful for treating or preventing a sleep disorder in an animal in need of such treatment or prevention.

5.6 Therapeutic/Prophylactic Administration and Compositions of the Disclosure

Due to their activity, the compounds of formula (I), (IA), (IB), and (IC), or a solvate thereof, are advantageously useful in human and veterinary medicine. As described above, the compounds of formula (I), (IA), (IB), and (IC), or a solvate thereof, are useful for treating or preventing an Insomnia Disorder in an animal in need thereof. In another embodiment, the compounds of formula (I), (IA), (IB), and (IC), or a solvate thereof, are useful for treating an Insomnia Disorder in an animal in need thereof. In another embodiment, the compounds of formula (I), (IA), (IB), and (IC), or a solvate thereof, are useful for preventing an Insomnia Disorder in an animal in need thereof. In another embodiment, the compounds of formula (I), (IA), (IB), and (IC), or a solvate thereof, of the disclosure can be administered to any animal requiring modulation of the opioid and/or ORL-1 receptors. In another embodiment, a compound of formula (I), (IA), (IB), and (IC), or a solvate thereof, is useful for treating insomnia associated with alcohol cessation in an animal in need thereof.

When administered to an animal, a compound of formula (I), (IA), (IB), or (IC), or a solvate thereof, can be administered as a component of a composition that comprises a pharmaceutically acceptable carrier or excipient.

Methods of administration include, but are not limited to, intradermal, intramuscular, intraperitoneal, parenteral, intravenous, subcutaneous, intranasal, epidural, oral, transmucosal, buccal, gingival, sublingual, intraocular, intracerebral, intravaginal, transdermal (e.g., via a patch), rectal, by inhalation, or topical, particularly to the ears, nose, eyes, or skin. In another embodiment, methods of administration include, but are not limited to, intravenous, oral, or by inhalation. In another embodiment, the method of administration is oral, parenteral, intravenous, intramuscular, intraocular, transdermal, or transmucosal. In another embodiment, the method of administration is oral. In another embodiment, the method of administration is buccal, gingival, sublingual, or by a swallowed-intact oral dosage form. In another embodiment, the method of administration is by a swallowed-intact oral dosage form. In another embodiment, the method of administration is intravenous. In another embodiment, the method of administration is by inhalation. The method of administration is left to the discretion of the practitioner. In some instances, administration will result in the release of a compound of formula (I), (IA), (IB), or (IC), or a solvate thereof, into the bloodstream. In other instances, administration will result in only local release of a compound of formula (I), (IA), (IB), or (IC), or a solvate thereof.

In certain embodiments, it can be desirable to introduce a compound of formula (I), (IA), (IB), or (IC), or a solvate thereof, into the central nervous system or gastrointestinal tract by any suitable route, including intraventricular, intrathecal, or epidural injection, or enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound of formula (I), (IA), (IB), or (IC), or a solvate thereof, can be formulated as a suppository, with traditional binders and excipients such as triglycerides.

When a compound of formula (I), (IA), (IB), or (IC), or a solvate thereof, of the disclosure is incorporated for parenteral administration by injection (e.g., continuous infusion or bolus injection), the formulation for parenteral administration can be in the form of a suspension, solution, emulsion in an oily or aqueous vehicle. Such formulations can further comprise pharmaceutically necessary additives such as one or more stabilizing agents, suspending agents, dispersing agents, buffers, and the like. A compound of formula (I), (IA), (IB), or (IC), or a solvate thereof, of the disclosure can also be in the form of a powder for reconstitution as an injectable formulation.

In another embodiment, a compound of formula (I), (IA), (IB), or (IC), or a solvate thereof, can be delivered in a vesicle, in particular a liposome (see Langer, "New Methods of Drug Delivery," Science 249:1527-1533 (1990); and Treat et al., "Liposome Encapsulated Doxorubicin Preliminary Results of Phase I and Phase II Trials," pp. 317-327 and 353-365 in Liposomes in the Therapy of Infectious Disease and Cancer (1989)).

In yet another embodiment, a compound of formula (I), (IA), (IB), or (IC), or a solvate thereof, can be delivered in a controlled-release system or sustained-release system. Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a compound of formula (I), (IA), (IB), or (IC), or a solvate thereof, to treat or prevent the Insomnia Disorder or a symptom thereof in an extended amount of time. Advantages of controlled- or sustained-release compositions include extended activity of the drug, reduced dosing frequency, and increased compliance. In addition, controlled- or sustained-release compositions can favorably affect the time of onset of action or other characteristics, such as blood levels of the compound of formula (I), (IA), (IB), or (IC), or a solvate thereof, and can thus reduce the occurrence of adverse side effects.

Controlled- or sustained-release compositions can initially, e.g., substantially immediately, release an amount of a compound of formula (I), (IA), (IB), or (IC), or a solvate thereof, that promptly produces the desired therapeutic or prophylactic effect, and gradually and continually release other amounts of the compound of formula (I), (IA), (IB), or (IC), or a solvate thereof, to maintain this level of therapeutic or prophylactic effect over an extended period of time. To maintain a constant level of the compound of formula (I), (IA), (IB), or (IC), or a solvate thereof, in the body, the compound of formula (I), (IA), (IB), or (IC), or a solvate thereof, can be released from the dosage form at a rate that will replace the amount of the compound of formula (I), (IA), (IB), or (IC), or a solvate thereof, being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds. In yet another embodiment, a controlled- or sustained-release system can be placed in proximity of a target of a compound of formula (I), (IA), (IB), or (IC), or a solvate thereof, e.g., the spinal column or brain, thus requiring only a fraction of the systemic dose.

Administration of a compound of formula (I), (IA), (IB), or (IC), or a solvate thereof, can be by controlled-release or sustained-release means or by delivery devices that are known to those in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566, each of which is incorporated herein by reference. Numerous other controlled-release or sustained-release delivery devices that are known to those in the art (see, e.g., Goodson, "Dental Applications," in Medical Applications of Controlled Release, Vol. 2, Applications and Evaluation, Langer and Wise, eds., CRC Press, Chapter 6, pp. 115-138 (1984), hereafter "Goodson"). Other controlled- or sustained-release systems discussed in the review by Langer, *Science* 249:1527-1533 (1990) can be used. In one embodiment, a pump can be used (Langer, *Science* 249:1527-1533 (1990); Sefton, "Implantable Pumps," in *CRC Crit. Rev. Biomed. Eng.* 14(3):201-240 (1987); Buchwald et al., "Long-term, Continuous Intravenous Heparin Administration by an Implantable Infusion Pump in Ambulatory Patients with Recurrent Venous Thrombosis," Surgery 88:507-516 (1980); and Saudek et al., "A Preliminary Trial of the Programmable Implantable Medication System for Insulin Delivery," *New Engl. J. Med.* 321:574-579 (1989)). In another embodiment, polymeric materials can be used (see Goodson; Smolen et al., "Drug Product Design and Performance," *Controlled Drug Bioavailability Vol.* 1, John Wiley and Sons, New York (1984); Langer et al., "Chemical and Physical Structure of Polymers as Carriers for Controlled Release of Bioactive Agents: A Review," *J. Macromol. Sci. Rev. Macromol. Chem.* C23(1):61-126 (1983); Levy et al., "Inhibition of Calcification of Bioprosthetic Heart Valves by Local Controlled-Release Diphosphonate," *Science* 228:190-192 (1985); During et al., "Controlled Release of Dopamine from a Polymeric Brain Implant: In Vivo Characterization," *Ann. Neurol.* 25:351-356 (1989); and Howard et al., "Intracerebral drug delivery in rats with lesion-induced memory deficits," *J. Neurosurg.* 71:105-112 (1989)).

Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled- or sustained-release.

The compositions can optionally, but preferably, further comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a compound of formula (I), (IA), (IB), or (IC), or a solvate thereof, is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol mono-stearate, talc, sodium chloride, dried skim milk, glycerol, propylene glycol, water, ethanol, and the like. The compositions, if desired, can also contain minor amounts of wetting or emulsifying agents, or pH buffering agents. Specific examples of pharmaceutically acceptable carriers and excipients that can be used to formulate oral dosage forms are described in the Handbook of Pharmaceutical Excipients, (Amer. Pharmaceutical Ass'n, Washington, D C, 1986), incorporated herein by reference. Other examples of suitable pharmaceutical excipients are described by Radebough et al., "Preformulation," pp. 1447-1676 in *Remington's Pharmaceutical Sciences Vol.* 2 (Gennaro, ed., 19$^{th}$ Ed., Mack Publishing, Easton, Pa., 1995), incorporated herein by reference.

The compositions can take the form of solutions, suspensions, emulsions, tablets such as an orally disintegrating tablet (ODT), a sublingual tablet, or a swallowed-intact tablet, pills, pellets, capsules, capsules containing liquids, powders, sustained-release formulations, suppositories, emulsions, aerosols, sprays, suspensions, microparticles, multiparticulates, rapidly dissolving films or other forms for oral or mucosal administration, or any other form suitable for use. In one embodiment, the composition is in the form of an ODT (see, e.g., U.S. Pat. Nos. 7,749,533 and 9,241, 910). In another embodiment, the composition is in the form of a sublingual tablet (see, e.g., U.S. Pat. Nos. 6,572,891 and 9,308,175). In another embodiment, the composition is in the form of a capsule (see, e.g., U.S. Pat. No. 5,698,155). In another embodiment, the composition is in a form suitable for buccal administration, e.g., as a tablet, lozenge, gel, patch, or film, formulated in a conventional manner (see, e.g., Pather et al., "Current status and the future of buccal drug delivery systems," *Expert Opin. Drug Deliv.* 5(5):531-542 (2008)). In another embodiment, the composition is in a form suitable for gingival administration, e.g., as a polymeric film comprising polyvinyl alcohol, chitosan, polycarbophil, hydroxypropylcellulose, or Eudragit S-100, as disclosed by Padula et al., "In Vitro Evaluation of Mucoadhesive Films for Gingival Administration of Lidocaine," *AAPS PharmSciTech* 14(4):1279-1283 (2013). In another embodiment, the composition is in a form of a swallowed-intact oral dosage form. In another embodiment, the composition is in a form suitable for intraocular administration.

In one embodiment, the compounds of formula (I), (IA), (IB), or (IC), or a solvate thereof, are formulated in accordance with routine procedures as a composition adapted for oral administration to human beings. A compound of formula (I), (IA), (IB), or (IC), or a solvate thereof, to be orally delivered can be in the form of tablets, capsules, gelcaps, caplets, lozenges, aqueous or oily solutions, suspensions, granules, microparticles, multiparticulates, powders, emulsions, syrups, or elixirs, for example. The oral dosage form can be a swallowed-intact oral dosage form, such as a tablet, capsule, or gelcap. When a compound of formula (I), (IA), (IB), or (IC), or a solvate thereof, is incorporated into oral tablets, such tablets can be compressed, tablet triturates, enteric-coated, sugar-coated, film-coated, multiply compressed, or multiply layered. Techniques and compositions for making solid oral dosage forms are described in *Pharmaceutical Dosage Forms: Tablets* (Lieberman et al., eds., 2$^{nd}$ Ed., Marcel Dekker, Inc., 1989 and 1990). Techniques and compositions for making tablets (compressed and molded), capsules (hard and soft gelatin) and pills are also described by King, "Tablets, Capsules, and Pills," pp. 1553-1593 in *Remington's Pharmaceutical Sciences* (Osol, ed., 16$^{th}$ Ed., Mack Publishing, Easton, Pa., 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems* (Lieberman et al., eds., 2$^{nd}$ Ed., Marcel Dekker, Inc., 1996 and 1998).

An orally administered compound of formula (I), (IA), (IB), or (IC), or a solvate thereof, can contain one or more agents, for example, sweetening agents such as fructose, aspartame, or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol mono-stearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

When a compound of formula (I), (IA), (IB), or (IC), or a solvate thereof, is to be injected parenterally, it can be, e.g., in the form of an isotonic sterile solution. Alternatively, when a compound of formula (I), (IA), (IB), or (IC), or a solvate thereof, is to be inhaled, it can be formulated into a dry aerosol or can be formulated into an aqueous or partially aqueous solution.

In another embodiment, the compounds of formula (I), (IA), (IB), or (IC), or a solvate thereof, can be formulated for intravenous administration. In certain embodiments, compositions for intravenous administration comprise sterile isotonic aqueous buffer. Where necessary, the compositions can also include a solubilizing agent. A compound of formula (I), (IA), (IB), or (IC), or a solvate thereof, for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a compound of formula (I), (IA), (IB), or (IC), or a solvate thereof, is to be administered by infusion, it can be dispensed, for example, with an infusion bottle containing sterile pharmaceutical grade water or saline. Where a compound of formula (I), (IA), (IB), or (IC), or a solvate thereof, is administered by injection, an ampule of sterile water for injection or saline can be provided so that the ingredients can be mixed prior to administration.

The amount of the compound of formula (I), (IA), (IB), or (IC), or a solvate thereof, that is effective for the treatment or prevention of an Insomnia Disorder can be determined by standard clinical techniques. In addition, in vitro and/or in vivo assays can optionally be employed to help identify optimal dose ranges. The precise dose to be employed will also depend on, e.g., the route of administration and the seriousness of the Insomnia Disorder, and can be decided according to the judgment of a practitioner and/or each animal's circumstances. In other examples thereof, variations will necessarily occur depending upon the weight and physical condition (e.g., hepatic and renal function) of the animal being treated, the disorder to be treated, the severity of the symptoms, the frequency of the dosing interval, the presence of any deleterious side-effects, and the particular compound utilized, among other things.

In one embodiment, a suitable effective dose of the compound of formula (I), (IA), (IB), or (IC), or a solvate thereof, administered to a human as a daily dose is from about 0.16 mg to about 8.0 mg. In other embodiments, a suitable effective dose of the compound of formula (I), (IA), (IB), or (IC), or a solvate thereof, administered to a human as a daily dose is from about 0.2 mg to about 8.0 mg, from about 0.2 mg to about 7.0 mg, from about 0.2 mg to about 6.0 mg, from about 0.2 mg to about 5.5 mg, from about 0.2 mg to about 5.0 mg, from about 0.2 mg to about 4.5 mg, from about 0.2 mg to about 4.0 mg, from about 0.2 mg to about 3.5 mg, from about 0.2 mg to about 3.0 mg, from about 0.2 mg to about 2.5 mg, from about 0.2 mg to about 2.0 mg, from about 0.2 mg to about 1.8 mg, from about 0.2 mg to about 1.6 mg, from about 0.2 mg to about 1.5 mg, from about 0.2 mg to about 1.4 mg, from about 0.2 mg to about 1.3 mg, from about 0.2 mg to about 1.2 mg, from about 0.2 mg to about 1.1 mg, from about 0.2 mg to about 1.0 mg, 0.25 mg to about 8.0 mg, from about 0.25 mg to about 7.0 mg, from about 0.25 mg to about 6.0 mg, from about 0.25 mg to about 5.5 mg, from about 0.25 mg to about 5.0 mg, from about 0.25 mg to about 4.5 mg, from about 0.25 mg to about 4.0 mg, from about 0.25 mg to about 3.5 mg, from about 0.25 mg to about 3.0 mg, from about 0.25 mg to about 2.5 mg, from about 0.25 mg to about 2.0 mg, from about 0.25 mg to about 1.8 mg, from about 0.25 mg to about 1.6 mg, from about 0.25 mg to about 1.5 mg, from about 0.25 mg to about 1.4 mg, from about 0.25 mg to about 1.3 mg, from about 0.25 mg to about 1.2 mg, from about 0.25 mg to about 1.1 mg, from about 0.25 mg to about 1.0 mg, from about 0.3 mg to about 8.0 mg, from about 0.3 mg to about 7.0 mg, from about 0.3 mg to about 6.0 mg, from about 0.3 mg to about 5.5 mg, from about 0.3 mg to about 5.0 mg, from about 0.3 mg to about 4.5 mg, from about 0.3 mg to about 4.0 mg, from about 0.3 mg to about 3.5 mg, from about 0.3 mg to about 3.0 mg, from about 0.3 mg to about 2.5 mg, from about 0.3 mg to about 2.0 mg, from about 0.3 mg to about 1.8 mg, from about 0.3 mg to about 1.6 mg, from about 0.3 mg to about 1.5 mg, from about 0.3 mg to about 1.4 mg, from about 0.3 mg to about 1.3 mg, from about 0.3 mg to about 1.2 mg, from about 0.3 mg to about 1.1 mg, from about 0.3 mg to about 1.0 mg, from about 0.33 mg to about 8.0 mg, from about 0.33 mg to about 7.0 mg, from about 0.33 mg to about 6.0 mg, from about 0.33 mg to about 5.5 mg, from about 0.33 mg to about 5.0 mg, from about 0.33 mg to about 4.5 mg, from about 0.33 mg to about 4.0 mg, from about 0.33 mg to about 3.5 mg, from about 0.33 mg to about 3.0 mg, from about 0.33 mg to about 2.5 mg, from about 0.33 mg to about 2.0 mg, from about 0.33 mg to about 1.8 mg, from about 0.33 mg to about 1.6 mg, from about 0.33 mg to about 1.5 mg, from about 0.33 mg to about 1.4 mg, from about 0.33 mg to about 1.3 mg, from about 0.33 mg to about 1.2 mg, from about 0.33 mg to about 1.1 mg, from about 0.33 mg to about 1.0 mg, from about 0.35 mg to about 8.0 mg, from about 0.35 mg to about 7.0 mg, from about 0.35 mg to about 6.0 mg, from about 0.35 mg to about 5.5 mg, from about 0.35 mg to about 5.0 mg, from about 0.35 mg to about 4.5 mg, from about 0.35 mg to about 4.0 mg, from about 0.35 mg to about 3.5 mg, from about 0.35 mg to about 3.0 mg, from about 0.35 mg to about 2.5 mg, from about 0.35 mg to about 2.0 mg, from about 0.35 mg to about 1.8 mg, from about 0.35 mg to about 1.6 mg, from about 0.35 mg to about 1.5 mg, from about 0.35 mg to about 1.4 mg, from about 0.35 mg to about 1.3 mg, from about 0.35 mg to about 1.2 mg, from about 0.35 mg to about 1.1 mg, from about 0.35 mg to about 1.0 mg, from about 0.4 mg to about 8.0 mg, from about 0.4 mg to about 7.0 mg, from about 0.4 mg to about 6.0 mg, from about 0.4 mg to about 5.5 mg, from about 0.4 mg to about 5.0 mg, from about 0.4 mg to about 4.5 mg, from about 0.4 mg to about 4.0 mg, from about 0.4 mg to about 3.5 mg, from about 0.4 mg to about 3.0 mg, from about 0.4 mg to about 2.5 mg, from about 0.4 mg to about 2.0 mg, from about 0.4 mg to about 1.8 mg, from about 0.4 mg to about 1.6 mg, from about 0.4 mg to about 1.5 mg, from about 0.4 mg to about 1.4 mg, from about 0.4 mg to about 1.3 mg, from about 0.4 mg to about 1.2 mg, from about 0.4 mg to about 1.1 mg, from about 0.4 mg to about 1.0 mg, from about 0.45 mg to about 6.0 mg, from about 0.45 mg to about 5.5 mg, from about 0.45 mg to about 5.0 mg, from about 0.45 mg to about 4.5 mg, from about 0.45 mg to about 4.0 mg, from about 0.45 mg to about 3.5 mg, from about 0.45 mg to about 3.0 mg, from about 0.45 mg to about 2.5 mg, from about 0.45 mg to about 2.0 mg, from about 0.45 mg to about 1.8 mg, from about 0.45 mg to about 1.6 mg, from about 0.45 mg to about 1.5 mg, from about 0.45 mg to about 1.4 mg, from about 0.45 mg to about 1.3 mg, from about 0.45 mg to about 1.2 mg, from about 0.45 mg to about 1.1 mg, from about 0.45 mg to about 1.0 mg, from about 0.46 mg to about 6.0 mg, from about 0.46 mg to about 5.5 mg, from about 0.46 mg to about 5.0 mg, from about 0.46 mg to about 4.5 mg, from about 0.46 mg to about 4.0 mg, from about 0.46 mg to about 3.5 mg, from about 0.46 mg to about 3.0 mg, from about 0.46 mg to about 2.5 mg, from about 0.46 mg to about 2.0 mg, from about 0.46 mg to about 1.8 mg, from about 0.46 mg to about 1.6 mg, from about 0.46 mg to about 1.5 mg, from about 0.46 mg to about 1.4 mg, from about 0.46 mg to about 1.3 mg, from about 0.46 mg to about 1.2 mg, from about 0.46 mg to about 1.1 mg, from about 0.46 mg to about 1.0 mg, from about 0.47 mg to about 6.0 mg, from about 0.47 mg to about 5.5 mg, from about 0.47 mg to about 5.0 mg, from about 0.47 mg to about 4.5 mg, from about 0.47 mg to about 4.0 mg, from about 0.47 mg to about 3.5 mg, from about 0.47 mg to about 3.0 mg, from about 0.47 mg to about 2.5 mg, from about 0.47 mg to about 2.0 mg, from about 0.47 mg to about 1.8 mg, from about 0.47 mg to about 1.6 mg, from about 0.47 mg to about 1.5 mg, from about 0.47 mg to about 1.4 mg, from about 0.47 mg to about 1.3 mg, from about 0.47 mg to about 1.2 mg, from about 0.47 mg to about 1.1 mg, from about 0.47 mg to about 1.0 mg, from about 0.48 mg to about 6.0 mg, from about 0.48 mg to about 5.5 mg, from about 0.48 mg to about 5.0 mg, from about 0.48 mg to about 4.5 mg, from about 0.48 mg to about 4.0 mg, from about 0.48 mg to about 3.5 mg, from about 0.48 mg to about 3.0 mg, from about 0.48 mg to about 2.5 mg, from about 0.48 mg to about 2.0 mg, from about 0.48 mg to about 1.8 mg, from about 0.48 mg to about 1.6 mg, from about 0.48 mg to about 1.5 mg, from about 0.48 mg to about 1.4 mg, from about 0.48 mg to about 1.3 mg, from about 0.48 mg to about 1.2 mg, from about 0.48 mg to about 1.1 mg, from about 0.48 mg to about 1.0 mg, from about 0.49 mg to about 6.0 mg, from about 0.49 mg to about 5.5 mg, from about 0.49 mg to about 5.0 mg, from about 0.49 mg to about 4.5 mg, from about 0.49 mg to about 4.0 mg, from about 0.49 mg to about 3.5 mg, from about 0.49 mg to about 3.0 mg, from about 0.49 mg to about 2.5 mg, from about 0.49 mg to about 2.0 mg, from about 0.49 mg to about 1.8 mg, from about 0.49 mg to about 1.6 mg, from about 0.49 mg to about 1.5 mg, from about 0.49 mg to about 1.4 mg, from about 0.49 mg to about 1.3 mg, from about 0.49 mg to about 1.2 mg, from about 0.49 mg to about 1.1 mg, from about 0.49 mg to about 1.0 mg, from about 0.5 mg to about 6.0 mg, from about 0.5 mg to about 5.5 mg, from about 0.5 mg to about 5.0 mg, from about 0.5 mg to about 4.5 mg, from about 0.5 mg to about 4.0 mg, from about 0.5 mg to about 3.5 mg, from about 0.5 mg to about 3.0 mg, from about 0.5 mg to about 2.5 mg, from about 0.5 mg to about 2.0 mg, from about 0.5 mg to about 1.8 mg, from about 0.5 mg to about 1.6 mg, from about 0.5 mg to about 1.5 mg, from about 0.5 mg to about 1.4 mg, from about 0.5 mg to about 1.3 mg, from about 0.5 mg to about 1.2 mg, from about 0.5 mg to about 1.1 mg, or from about 0.5 mg to about 1.0 mg. In any of these embodiments, the daily dose is optionally a single daily dose. In any of these embodiments, the daily dose is optionally a divided daily dose, e.g., 67%, 60% 50%, 40%, or 33% of any of the above doses is administered before the intended bedtime and the remaining 33%, 40%, 50%, 60%, or 67%, respectively, is administered later during the daily period, such as upon middle-of-the night awakening followed by failure to readily return to sleep.

In one embodiment, a suitable effective daily dose of the compound of formula (I), (IA), (IB), or (IC), or a solvate thereof, administered to a human is about 0.16 mg. In other embodiments, a suitable effective daily dose of the compound of formula (I), (IA), (IB), or (IC), or a solvate thereof, administered to a human is about 0.20 mg, about 0.30 mg, about 0.33 mg, about 0.35 mg, about 0.40 mg, about 0.45 mg, about 0.46 mg, about 0.47 mg, about 0.48 mg, about 0.49 mg, about 0.50 mg, about 0.525 mg, about 0.55 mg, about 0.575 mg, about 0.60 mg, about 0.625 mg, about 0.65 mg, about 0.675 mg, about 0.70 mg, about 0.725 mg, about 0.75 mg, about 0.775 mg, about 0.80 mg, about 0.825 mg, about 0.85 mg, about 0.875 mg, about 0.90 mg, about 0.925 mg, about 0.95 mg, about 0.975 mg, about 1.00 mg, about 1.10 mg, about 1.20 mg, about 1.30 mg, about 1.40 mg, about 1.50 mg, about 1.60 mg, about 1.70 mg, about 1.80 mg, about 1.90 mg, about 2.00 mg, about 2.10 mg, about 2.20 mg, about 2.30 mg, about 2.40 mg, about 2.50 mg, about 2.60 mg, about 2.70 mg, about 2.80 mg, about 2.90 mg, about 3.00 mg, about 3.25 mg, about 3.50 mg, about 3.75 mg, about 4.0 mg, about 4.5 mg, about 5.0 mg, about 5.5 mg, about 6.0 mg, about 6.5 mg, about 7.0 mg, about 7.5 mg, or about 8.0 mg. In any of these embodiments, the daily dose is optionally a single daily dose. In any of these embodiments, the daily dose is optionally a divided daily dose, e.g., 67%, 60% 50%, 40%, or 33% of any of the above doses is administered before the intended bedtime and the remaining 33%, 40%, 50%, 60%, or 67%, respectively, is administered later during the daily period, such as upon middle-of-the night awakening followed by failure to readily return to sleep.

It is to be understood that the term "daily" means a 24 hour cycle beginning at the time of administration of a compound of formula (I), (IA), (IB), or (IC), or a solvate thereof. For example, for an ordinary overnight sleep cycle, if a compound of formula (I), (IA), (IB), or (IC), or a solvate thereof, is administered at 9:30 PM, then that "day" ends at 9:29 PM on the following calendar day. In another example, for a shift-worker's sleep cycle if a compound of formula (I), (IA), (IB), or (IC), or a solvate thereof, is administered at 8:15 AM, then that "day" ends at 8:14 AM on the following calendar day.

As known to those in the art, for a human a daily dose (in mg) can be converted to a mg/kg/day dosage amount by dividing the mg dose by 60 kg, an art-recognized average mass of a human. For example, a daily human dose of 1.25 mg is so-converted to a dosage amount of about 0.021 mg/kg/day.

The effective dosing amounts described herein refer to total amounts administered; that is, if more than one compound of formula (I), (IA), (IB), or (IC), or a solvate thereof, is administered, the effective dosing amount corresponds to the total amount administered.

Administration can be as a single dose or as a divided dose. In one embodiment, an effective dose or dosage amount is administered only as needed (pro re nata) such as, for example, in the event that sleep cannot readily be achieved, or upon middle-of-the night awakening followed by failure to readily return to sleep. In another embodiment, an effective dose or dosage amount is administered about every 24 hours, for example, before the intended bedtime, until the Insomnia Disorder is abated.

In another embodiment, an effective dose or dosage amount is administered before the intended bedtime to abate the Insomnia Disorder. In other embodiments, an effective dose or dosage amount is administered before the intended bedtime on 2, 3, 4, 5, 6, 7, 8, 9, 10, up to 12, 12, at least 12, up to 14, 14, at least 14, up to 21, 21, at least 21, up to 28, 28, at least 28, up to 34, 34 at least 34, up to 40, 40, at least 40, up to 50, 50, at least 50, up to 60, 60, at least 60, up to 75, 75, at least 75, up to 90, 90, at least 90, up to 120, 120, at least 120, up to 150, 150, at least 150, up to 180, 180, at least 180, up to 270, 270, at least 270, up to 360, 360, or on at least 360 consecutive days to abate the Insomnia Disorder. In other embodiments, an effective dose or dosage amount is administered before the intended bedtime daily for at least 1, 2, 3, 4, 5, 6, 7, 8, 9, 10, up to 12, 12, at least 12, up to 16, 16, at least 16, up to 26, 26, at least 26, up to 52, 52, at least 52 weeks. In other embodiments, an effective dose or dosage amount is administered before the intended bedtime daily for at least 1, 2, 3, 4, 5, 6, 7, 8, 9, 10, up to 12, 12, at least 12 months. In any of these embodiments, the daily dose is optionally a single daily dose.

In one embodiment, an effective dose or dosage amount is administered in preparation for sleep, which can be, e.g., about 90 minutes before the intended bedtime. In other embodiments, an effective dose or dosage amount is administered in preparation for sleep, which can be about 75 minutes before, about 60 minutes before, about 45 minutes before, about 30 minutes before, about 20 minutes before, about 20 minutes or less before, about 15 minutes before, about 15 minutes or less before, about 10 minutes before, about 10 minutes or less before, about 5 minutes before, about 5 minutes or less before, about 2 minutes before, about 2 minutes or less before, or about 1 minute before the intended bedtime, or at the intended bedtime.

In one embodiment, an effective dose or dosage amount is administered in preparation for sleep, which can be, e.g., from about 90 minutes before to about 30 minutes before the intended bedtime. In other embodiments, an effective dose or dosage amount is administered in preparation for sleep, which can be from about 90 minutes before to about 30 minutes before, from about 75 minutes before to about 30 minutes before, from about 60 minutes before to about 30 minutes before, from about 45 minutes before to about 30 minutes before, from about 90 minutes before to about 20 minutes before, from about 75 minutes before to about 20 minutes before, from about 60 minutes before to about 20 minutes before, from about 45 minutes before to about 20 minutes before, from about 30 minutes before to about 20 minutes before, from about 90 minutes before to about 15 minutes before, from about 75 minutes before to about 15 minutes before, from about 60 minutes before to about 15 minutes before, from about 45 minutes before to about 15 minutes before, from about 30 minutes before to about 15 minutes before, from about 20 minutes before to about 15 minutes before, from about 90 minutes before to about 10 minutes before, from about 75 minutes before to about 10 minutes before, from about 60 minutes before to about 10 minutes before, from about 45 minutes before to about 10 minutes before, from about 30 minutes before to about 10 minutes before, from about 20 minutes before to about 10 minutes before, from about 15 minutes before to about 10 minutes before, from about 90 minutes before to about 5 minutes before, from about 75 minutes before to about 5 minutes before, from about 60 minutes before to about 5 minutes before, from about 45 minutes before to about 5 minutes before, from about 30 minutes before to about 5 minutes before, from about 20 minutes before to about 5 minutes before, from about 15 minutes before to about 5 minutes before, from about 10 minutes before to about 5 minutes before the intended bedtime, or from about 90, 75, 60, 45, 30, 20, 15, or 10 minutes before the intended bedtime to about the intended bedtime.

In one embodiment, an effective dose or dosage amount is administered daily to treat or prevent insomnia associated with alcohol cessation. In another embodiment, an effective dose or dosage amount is administered before the intended bedtime to treat or prevent insomnia associated with alcohol cessation. In another embodiment, an effective dose or dosage amount is administered starting after alcohol consumption is ceased (e.g., after a subject with alcohol use disorder begins abstaining from alcohol consumption). In another embodiment, an effective dose or dosage amount that is administered starting after alcohol consumption is ceased can continue to be administered after alcohol is consumed (e.g., a subject who has abstained from alcohol consumes alcohol). In another embodiment, an effective dose or dosage amount is administered before alcohol consumption is ceased (e.g., while subject with alcohol use disorder continues to consume). In other embodiments, an effective dose or dosage amount is administered starting at least 1, 2, 3, 4, 5, 6, 7, 8, 9, 10, up to 12, 12, at least 12, up to 14, 14, at least 14, up to 21, 21, at least 21, up to 28, 28, at least 28, up to 34, 34 at least 34, up to 40, 40, at least 40, up to 50, 50, at least 50, up to 60, 60, at least 60, up to 75, 75, at least 75, up to 90, 90, at least 90, up to 120, 120, at least 120, up to 150, 150, at least 150, up to 180, 180, at least 180, up to 270, 270, at least 270, up to 360, 360, or at least 360 days after alcohol consumption ceases. In other embodiments, an effective dose or dosage amount is administered starting at least 1, 2, 3, 4, 5, 6, 7, 8, 9, 10, up to 12, 12, at least 12, up to 16, 16, at least 16, up to 26, 26, at least 26, up to 52, 52, at least 52 weeks after alcohol consumption ceases. In other embodiments, an effective dose or dosage amount is administered starting at least 1, 2, 3, 4, 5, 6, 7, 8, 9, 10, up to 12, 12, at least 12 months after alcohol consumption ceases. In any of these embodiments, the daily dose is optionally a single daily dose.

A compound of formula (I), (IA), (IB), or (IC) can be administered to a subject who has ingested alcohol or a subject may ingest alcohol following administration of the compound. In an embodiment, the amount of ethanol ingested is about 0.05 g/kg to about 5.0 g/kg; about 0.05 g/kg to about 2.0 g/kg; about 0.05 g/kg to about 1.0 g/kg; about 0.05 g/kg to about 0.5 g/kg; about 0.05 g/kg to about 0.2 g/kg; about 0.2 g/kg to about 5.0 g/kg; about 0.2 g/kg to about 2.0 g/kg; about 0.2 g/kg to about 1.0 g/kg; about 0.2 g/kg to about 0.8 g/kg; about 0.2 g/kg to about 0.5 g/kg; about 0.5 g/kg to about 5.0 g/kg; about 0.5 g/kg to about 2.0 g/kg; about 0.5 g/kg to about 1.0 g/kg; or about 0.5 g/kg to about 0.8 g/kg.

In one embodiment, a composition comprising a compound of formula (I), (IA), (IB), or (IC), or a solvate thereof, in accordance with the disclosure is used as a medicament. In another embodiment, compositions comprising a compound of formula (I), (IA), (IB), or (IC), or a solvate thereof, are disclosed which can be used for preparing a medicament containing said compositions.

In another embodiment, a composition comprising a compound of formula (I), (IA), (IB), or (IC), or a solvate thereof, is useful as a medicament in the treatment or prevention of a sleep disorder.

In another embodiment, a composition comprising a compound of formula (I), (IA), (IB), or (IC), or a solvate thereof, is useful as a medicament in the treatment or prevention of a sleep disorder where the sleep disorder is an Insomnia Disorder, a hypersomnia disorder, a circadian rhythm sleep-wake disorder, an alcohol-induced sleep disorder, or any combination thereof.

In another embodiment, a composition comprising a compound of formula (I), (IA), (IB), or (IC), or a solvate thereof, is useful as a medicament in the treatment of a sleep disorder. In another embodiment, a composition comprising a compound of formula (I), (IA), (IB), or (IC), or a solvate thereof, is useful as a medicament in the treatment of a sleep disorder where the sleep disorder is an Insomnia Disorder, a hypersomnia disorder, a circadian rhythm sleep-wake disorder, an alcohol-induced sleep disorder, or any combination thereof.

In another embodiment, a composition comprising a compound of formula (I), (IA), (IB), or (IC), or a solvate thereof, is useful as a medicament in the prevention of a sleep disorder. In another embodiment, a composition comprising a compound of formula (I), (IA), (IB), or (IC), or a solvate thereof, is useful as a medicament in the prevention of a sleep disorder where the sleep disorder is an Insomnia Disorder, a hypersomnia disorder, a circadian rhythm sleep-wake disorder, an alcohol-induced sleep disorder, or any combination thereof.

In another embodiment, a composition comprising a compound of formula (I), (IA), (IB), or (IC), or a solvate thereof, is useful as a medicament in the treatment or prevention of an Insomnia Disorder. In another embodiment, a composition comprising a compound of formula (I), (IA), (IB), or (IC), or a solvate thereof, is useful as a medicament in the treatment of an Insomnia Disorder. In another embodiment, a composition comprising a compound of formula (I), (IA), (IB), or (IC), or a solvate thereof, is useful as a medicament in the prevention of an Insomnia Disorder.

In another embodiment, a composition comprising a compound of formula (I), (IA), (IB), or (IC), or a solvate thereof, is useful as a medicament in the treatment or prevention of an alcohol-induced sleep disorder. In another embodiment, a composition comprising a compound of formula (I), (IA), (IB), or (IC), or a solvate thereof, is useful as a medicament in the treatment of an alcohol-induced sleep disorder. In another embodiment, a composition comprising a compound of formula (I), (IA), (IB), or (IC), or a solvate thereof, is useful as a medicament in the prevention of an alcohol-induced sleep disorder.

For any of these uses, the composition comprising a compound of formula (I), (IA), (IB), or (IC), or a solvate thereof, can further comprise a second therapeutic agent in the medicament.

The methods for treating or preventing an Insomnia Disorder in an animal in need thereof can further comprise co-administering to the animal being administered a compound of formula (I), (IA), (IB), or (IC), or a solvate thereof (i.e., a first therapeutic agent), a second therapeutic agent. In one embodiment, the second therapeutic agent is administered in an effective amount.

An effective amount of the second therapeutic agent will be known to those skilled the art depending on the agent. However, it is well within the skilled artisan's purview to determine the second therapeutic agent's optimal effective-amount range in view of the present disclosure. A compound of formula (I), (IA), (IB), or (IC), or a solvate thereof, and the second therapeutic agent combined can act either additively or synergistically to treat the Insomnia Disorder, or they may act independently of each other such that the compound of formula (I), (IA), (IB), or (IC), or a solvate thereof, treats or prevents an Insomnia Disorder and the second therapeutic agent treats or prevents another disorder, which can be the same as or different from the Insomnia Disorder. In one embodiment of the disclosure, where a second therapeutic agent is co-administered to an animal for treatment of a disorder (e.g., a sleep disorder), the minimal effective amount of the compound of formula (I), (IA), (IB), or (IC), or a solvate thereof, can be less than its minimal effective amount would be where the second therapeutic agent is not administered. In this embodiment, the compound of formula (I), (IA), (IB), or (IC), or a solvate thereof, and the second therapeutic agent can act synergistically to treat or prevent the Insomnia Disorder.

In one embodiment, a compound of formula (I), (IA), (IB), or (IC), or a solvate thereof, is administered concurrently with a second therapeutic agent as a single composition comprising an effective amount of a compound of formula (I), (IA), (IB), or (IC), or a solvate thereof, and an effective amount of the second therapeutic agent. Alternatively, a composition comprising an effective amount of a compound of formula (I), (IA), (IB), or (IC), or a solvate thereof, and a second composition comprising an effective amount of the second therapeutic agent are concurrently administered. In another embodiment, an effective amount of a compound of formula (I), (IA), (IB), or (IC), or a solvate thereof, is administered prior or subsequent to administration of an effective amount of the second therapeutic agent. In this embodiment, the compound of formula (I), (IA), (IB), or (IC), or a solvate thereof, is administered while the second therapeutic agent exerts its therapeutic effect, or the second therapeutic agent is administered while the compound of formula (I), (IA), (IB), or (IC), or a solvate thereof, exerts its therapeutic effect for treating or preventing the Insomnia Disorder.

The second therapeutic agent can be, but is not limited to, an opioid agonist, a non-opioid analgesic, a non-steroidal anti-inflammatory agent, an antimigraine agent, a second sedative or hypnotic, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for inhibiting vomiting, an agent for treating or preventing dyskinesia, an agent for treating or preventing depression, an agent for treating or preventing alcohol use disorder, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts or solvates thereof, or any mixture thereof.

In certain embodiments, the opioid agonist is codeine, hydromorphone, hydrocodone, oxycodone, dihydrocodeine, dihydromorphine, morphine, tramadol, oxymorphone, pharmaceutically acceptable salts or solvates thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable salt thereof, or any mixture thereof. Other suitable non-opioid analgesics include the following, non-limiting, chemical classes of analgesic, antipyretic, non-steroidal anti-inflammatory drugs; salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable salt thereof; or any mixture thereof. For a more detailed description of the NSAIDs, see Insel, "Analgesic-Antipyretic and Anti-inflammatory Agents and Drugs Employed in the Treatment of Gout," pp. 617-657 in *Goodman and Gilman's The Pharmacological Basis of Therapeutics* (Goodman et al., eds., $9^{th}$ Ed., McGraw-Hill, New York 1996), and Hanson, "Analgesic, Antipyretic and Anti-Inflammatory Drugs," pp. 1196-1221 in *Remington: The Science and Practice of Pharmacy Vol. II* (Gennaro, ed., $19^{th}$ Ed., Mack Publishing, Easton, Pa., 1995), which are hereby incorporated by reference in their entireties.

Examples of useful second sedatives or hypnotics include, but are not limited to, benzodiazepines, including lorazepam, temazepam, and triazolam; barbiturates, including phenobarbital, pentobarbital, and secobarbital; so-called "z-drugs," including zaleplon, zolpidem, and zopiclone; ramelteon; suvorexant; a pharmaceutically acceptable salt thereof, or any mixture thereof.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable salt thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable salt thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, *solanum*, strontium bromide, suclofenide, sulthiame, tetrantoin, tiagabine, topiramate, trimethadione, valproic acid, valpromide, vigabatrin, zonisamide, a pharmaceutically acceptable salt thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable salt thereof, or any mixture thereof.

Examples of useful therapeutic agents for treating or preventing UI include, but are not limited to, propantheline, imipramine, hyoscyamine, oxybutynin, dicyclomine, a pharmaceutically acceptable salt thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable salt thereof; or any mixture thereof.

Examples of useful therapeutic agents for treating or preventing diarrhea include, but are not limited to, diphenoxylate, loperamide, a pharmaceutically acceptable salt thereof, or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable salt thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable salt thereof, or any mixture thereof.

Examples of non-steroidal anti-inflammatory agents, 5-lipoxygenase inhibitors, anti-emetics, β-adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

Examples of agents for treating or preventing alcohol use disorder are known in the art and can be selected by those skilled in the art. Examples of useful therapeutic agents for treating or preventing alcohol use disorder, include, but are not limited to disulfiram, naltrexone, acamprosate, gabapentin, topiramate, nalmefenem, naloxone, fluoxetine, and quetiapine.

A composition of the disclosure is prepared by a method comprising admixing a compound of formula (I), (IA), (IB), or (IC), or a solvate thereof, with a pharmaceutically acceptable carrier or excipient. Admixing can be accomplished using methods known for admixing a compound (or derivative) and a pharmaceutically acceptable carrier or excipient. In one embodiment, the compound of formula (I), (IA), (IB), or (IC), or a solvate thereof, is present in the composition in an effective amount.

5.7 Kits

The disclosure further provides kits that can simplify the handling and administration of a compound of formula (I), (IA), (IB), or (IC), or a solvate thereof, to an animal.

A typical kit of the disclosure comprises a unit dosage form of a compound of formula (I), (IA), (IB), or (IC), or a solvate thereof. In one embodiment, the unit dosage form is suitable for oral administration such as, but not limited to, a capsule, a gelcap, a caplet, or a tablet, such as an ODT or a swallowed-intact tablet. In another embodiment, the unit dosage form comprises a first container, which can be sterile, containing an effective amount of a compound of formula (I), (IA), (IB), or (IC), or a solvate thereof, and a pharmaceutically acceptable carrier or excipient. The kit can further comprise a label or printed instructions instructing the use of the compound of formula (I), (IA), (IB), or (IC), or a solvate thereof, to treat or prevent the Insomnia Disorder. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a compound of formula (I), (IA), (IB), or (IC), or a solvate thereof, an effective amount of a second therapeutic agent and a pharmaceutically acceptable carrier or excipient. Examples of second therapeutic agents include, but are not limited to, those listed above.

Kits of the disclosure can further comprise a device useful for administering the unit dosage form. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

6. EXAMPLES

Certain examples below relate to methods for treating or preventing a sleep disorder by administering a compound of formula (I), (IA), (IB), and/or (IC) to a human in need of such treatment.

6.1 Example 1: Human Trial Protocol

A randomized, double-blind, multi-center, 5-period, crossover, repeat dose study assessing the effects of Compound (1C) on sleep efficiency ("SE"), Total Sleep Time ("TST"), Wake After Sleep Onset ("WASO"), Latency to Persistent Sleep ("LPS"), and time spent in sleep Stage N2 in subjects suffering from the Insomnia Disorder adult insomnia was performed. The study randomized up to about 30 subjects to achieve at least about 24 completers (i.e., subjects who completed all 5 Dosing Periods). The subjects included otherwise healthy males and females aged 18 to 64 years, inclusive, with a history of adult insomnia (insomnia disorder as defined by DSM-5 criteria) and who otherwise had no significant medical or psychiatric history.

This study used two consecutive dosing nights of orally administered Compound (1C) or placebo in each of 5 separate dosing periods (Dosing Periods 1-5) that were at least five days apart during an about 27-day-long treatment period. Compound (1C) was administered orally in an immediate release tablet comprising the pharmaceutically acceptable excipients croscarmellose sodium (FMC Health and Nutrition, Philadelphia, Pa.), hydroxypropylcellulose (Ashland Inc., Covington, Ky.), microcrystalline cellulose (Sigma-Aldrich, St. Louis, Mo.), and mannitol (SPI Pharma, Wilmington, Del.). Each subject was administered a single dose of 0.5 mg, 1.0 mg, 3.0 mg, or 6.0 mg of Compound (1C), with each subject dosed about 30 minutes before their median habitual bedtime. Placebo tablets matching the Compound (1C) tablets were orally administered in the same way. The placebo tablets comprised the four above-described pharmaceutically acceptable excipients but with no Compound (1C).

The study consisted of three periods: (1) pre-randomization (up to 28 days), (2) treatment (27 days), and (3) follow-up.

(1) The pre-randomization period protocol consisted of a screening visit ("Visit 1") followed, for successful subjects, by a baseline visit ("Visit 2"), each described in more detail as follows.

During a screening visit (Days −28 to −8), inter alia, vital signs, medical, sleep and psychiatric histories, clinical laboratory test results, drug screen results, Colombia-suicide severity rating scale ("C-SSRS") assessment, and an ECG were obtained. If a washout of prohibited medications was required, this washout was completed during the screening. Each subject who successfully completed the screening visit received a sleep-habits diary in which was recorded, e.g., the subject's intended bedtime, that was completed for a minimum of seven consecutive days before the baseline visit so that the median habitual bedtime for that subject could be assessed.

During a baseline visit (Days −7 to −6), successful subjects arrived at a clinical unit in the afternoon or evening of Day −7. At that time, they began a stay of two consecutive nights during which each subject underwent continuous PSG recording for eight hours on the first night (Night 1) to assess eligibility criteria and to screen out subjects with sleep apnea or periodic limb movements with arousal. Still-successful subjects underwent another eight hours of continuous PSG recording on the second night (Night 2), which determined if a subject met the sleep-eligibility criteria based on the average of data obtained on Nights 1 and 2 of the baseline visit. During the baseline visit, subjects also practiced and took a post-sleep test used in this study, i.e., the digit symbol substitution test ("DSST"), and familiarized themselves with the Karolinska Sleepiness Scale ("KSS") evaluation form. To assess a subject's perception of the "quality" and "quantity" of sleep, a post-sleep questionnaire was used to ask questions such as "how many minutes did it take you to fall asleep last night after you got into bed and the lights were turned off?", "how many times did you awaken during the night?", and "on a scale from 1 to 10, with 1 being poor and 10 being excellent, how would you rate the quality of your sleep last night?". Subjects who met all eligibility criteria after the baseline visit returned approximately seven days later to enter the treatment period (Dosing Periods 1-5).

A summary of the PSG recording procedure that was used is as follows. Standard placements for EEG electrodes were derived according to the international 10-20 system (see, e.g., Jasper, "The ten-twenty electrode system of the international federation," *Electroencephalography Clin. Neurophys.* 10:371-375 (1958)) with the exception of the change of the A1-A2 labels to M1-M2, pursuant to the AASM Manual for Scoring of Sleep (Berry et al., "The AASM Manual for the Scoring of Sleep and Associated Events: Rules, Terminology and Technical Specifications," Version 2.0.3, American Academy of Sleep Medicine, Darien, Ill., (2014)). This system requires that electrodes be positioned in measured relationships to landmark anatomical points. Standard placements for EOG, submental EMG electrodes, anterior tibialis EMG electrodes, and airflow sensors were consistent with the AASM Manual for Scoring of Sleep.

Electrodes used for EEG recording were standard gold- or silver-cup electrodes intended for use in EEG recording. These electrodes were approximately 4 to 10 mm. in diameter and were connected to a thin wire having an appropriate connector. Electrodes used for EOG and EMG recordings were self-adhesive electrodes of approximately 12 mm. diameter with snap-on connectors that enabled the electrode to be connected to a thin wire having an appropriate connector. Electrodes used for ECG recordings were self-adhesive electrodes of approximately 12 mm. diameter with snap-on connectors that enabled the electrode to be connected to a thin wire having an appropriate connector (e.g., 3M RED DOT electrodes or MEDITRACE electrodes).

Scalp and skin surfaces at points of contact with an electrode were thoroughly cleansed prior to electrode placement by applying a mild abrasive cleanser on both scalp and skin surfaces according to manufacturers' recommendations using a cotton swab. Isopropyl alcohol was used to wipe the abraded surface. A small dab of conductive EEG paste was then applied to the scalp or skin surface and to the cup electrodes. When facial or body hair was present at a desired site, if an insignificant deviation from the required electrode placement was possible an electrode was relocated to an adjacent area, otherwise, the facial or body hair was removed.

The electrical impedance of all EEG, EOG, submental EMG, limb EMG, and ECG electrodes was less than 5 kOhms; electrical impedance was checked prior to the start of recording using a commercially-available impedance meter. Digital PSG systems were calibrated prior to each PSG recording performed 45 minutes prior to "lights-off." Calibration involved the use of internally generated input signals of known voltage, which served as benchmarks against which physiological data were measured and quantified. The digital PSG calibration settings were as follows:

| Channel | Low Frequency Filter (Hz) | High Frequency Filter (Hz) |
|---|---|---|
| EOG | 0.3 | 35 |
| EMG | 10 | 70 to 120 |
| EEG | 0.3 | 35 |
| ECG | 0.3 | 70 |
| Airflow | 0.1 | 15 |

Acquisition of EEG signals occurred at a minimum sampling rate that was approximately three times the high-frequency filter setting. Specifically, the minimum sampling rate for EEGs collected using the high-frequency filter setting specified was at least 100 samples per second, or 100 Hz. No sampling rate greater than 256 Hz was used. The minimum storage rate for all PSG data was 200 Hz.

Biological calibration or "biocalibration" is a procedure in which the subject, in bed and supine, lies awake quietly and performs specific actions or movements in a specified sequence so that the quality of PSG signals may be assessed. Biocalibration was performed 15 minutes before lights-off. However, immediately following the completion of biocalibration procedures, the subject was awake and instructed to sit up to leave a reasonable time for "settling" before lights-off. Subjects were instructed not to move their heads or bodies unnecessarily while biocalibration procedures were performed so that head or body movement did not result in an artifact that obscured a biocalibration signal. Biocalibration procedures were performed on PSG nights according to the following schedule:

| Instruction to Subject | Biocalibration Duration | Nights |
|---|---|---|
| "Rest with your eyes closed" | 30 sec. of artifact-free tracing | All |
| "Rest with your eyes open" | 30 sec. of artifact-free tracing | All |
| "Open your eyes," "close your eyes" | 1 min. (30 sec. each) | All |
| "Open your eyes" | 5 sec. | All |
| "Look up," "look down" | Several times during a 30 sec. period | All |
| "Open your eyes" | 5 sec. | All |
| "Glance to the left," "glance to the right" | Several times during a 30 second period | All |
| "Grit your teeth," "stick out your tongue," "stick out your jaw" | 5 to 10 sec. | All |
| "Breathe in and out through your mouth" | 15 sec. | Screening Nights |
| "Breathe in and out through your nose" | 15 sec. | Screening Nights |
| "Hold your breath" | 5 sec. | Screening Nights |
| "Flex your left toe/leg" | 5 to 10 sec. | Screening Nights |
| "Flex your right toe/leg" | 5 to 10 sec. | Screening Nights |

A PSG "screening montage" of 18 channels of recording displayed in a specific sequence was used for Night 1. A "treatment montage" of 12 channels of recording displayed in a specific sequence was used for Night 2 and treatment nights. The following electrode derivations or positions were eliminated from the screening montage to yield the treatment montage: left anterior tibialis, right anterior tibialis, nasal/oral airflow (thermistor), nasal airflow (nasal pressure transducer), respiratory inductance plethysomography, and respiratory inductance plethysomography.

(2) The 27-day treatment period included five dosing periods (Dosing Periods 1-5) that were at least 5 days apart. Once continued eligibility was confirmed, subjects were randomized as to treatment upon check-in on Day 1. Each of Dosing Period 1 (Days 1 to 6), Dosing Period 2 (Days 7 to 12), Dosing Period 3 (Days 13 to 18), Dosing Period 4 (Days 19 to 24), and Dosing Period 5 (Days 25 to 27) (based upon the minimum washout of 5 days between periods) consisted of a stay of two consecutive nights, during which subjects received the same dose of study drug (Compound (1C) or placebo on both evenings of that dosing period. The study drug was administered 30 minutes before each subject's median habitual bedtime (to the nearest quarter hour as determined from the sleep diary) in each dosing period according to the study randomization schedule. The time subjects spent in bed in an undisturbed environment was fixed at 8 hours (i.e., 960 PSG epochs of 30 seconds duration per epoch).

Following the evening-time dosing with study drug, subjects underwent eight hours of continuous PSG recording. Next-day residual effects were assessed by the DSST and the KSS evaluation, collected in that order, starting at approximately 30 minutes after "lights-on." All tests were administered in the clinical unit, beginning 30 minutes after lights-on and periodically thereafter for approximately 16 hours post-lights-off, following completion of PSG recording. Each subject also completed a post-sleep questionnaire once after lights-on so that subjective impressions could be assessed about the "quality" and "quantity" of their sleep. Before the second night dosing in each dosing period, subjects were evaluated for any residual sleepiness. For subjects who exhibited continued sedation, the second night dosing was withheld. Subjects remained in the clinic until residual symptoms were minimized.

During the screening visit and prior to discharge from Dosing Period 5 (Day 27), subjects had a urinalysis with microscopy, chemistry and hematology collected.

Blood was collected pre-dose on Nights 1 and 2 of each dosing period, 15 minutes after administration on Night 1 of each dosing period, and at 9, 10, 11, 12, 14 and 16 hours after administration on Night 2 of each dosing period to determine the plasma concentration of drug.

(3) A follow-up period (Days 28-36) included a telephone call completed 6 to 9 days after the last dose of the study drug to monitor adverse effects and use of concomitant medication/therapy since the previous visit.

6.2 Example 2: Statistical Methods

In general, categorical variables were summarized by the count ("N") and percentage of subjects. Continuous variables were summarized by the number of non-missing observations ("n"), mean, standard deviation ("SD"), standard error ("STDE"), median, and minimum and maximum values.

The full-analysis population ("FAP") was the group of subjects who were randomized and received one dose of the study drug. Exposure to study drug was presented for each treatment group. The analysis population for efficacy was the FAP.

An important indication of efficacy was the effects of Compound (1C) on SE as measured by PSG. For the purposes of summary and analysis, the mean SE obtained from PSG was used per subject per treatment. It was derived by taking the mean of SE for Days 1 and 2 per treatment period or baseline. The two PSG nights in each treatment period were averaged before comparison. When data from only one of these days were available, the available data were taken as the measurement for that period. The baseline, post-baseline, and change of baseline of SE were summarized by treatment group by using descriptive statistics. The statistical analysis to compare Compound (1C) versus placebo was performed by using a mixed model approach that included period, sequence, and treatment as fixed effects, subject within the sequence as random effect, and the baseline measurement of SE as a covariate. The 2-sided significance level of 0.05 was used for comparison.

Subjects underwent eight hours of PSG recording, and PSGs were collected and scored by a central reader. Sleep stages were scored following AASM standard criteria based on 30-second epochs. Polysomnography parameters, including LPS, REM latency, NAW, TST, WASO, and total minutes of Stages of N, N2, N3, and REM were thusly compiled during treatment periods. Subjective sleep quality and depth of sleep as measured by the post-sleep questionnaire were also thusly compiled during treatment periods.

The baseline, post-baseline, and change from baseline of WASO were summarized by treatment group by using descriptive statistics. The analysis was performed by using a mixed model approach that included period, sequence, and treatment as fixed effects, subject within sequence as random effect, and the baseline measurement of WASO as covariate.

Other variables (TST; LPS; total minutes of Stages of N1, N2, N3, and REM; REM latency; NAW as measured by PSG; and sleep quality and depth of sleep as measured by the post-sleep questionnaire) were summarized and analyzed as detailed above for the WASO parameter. The next-day residual effects parameters, measured by DSST and KSS, were summarized using descriptive statistics.

Missing data handling—For the PSG sleep parameters, their baseline was defined as the assessments on the nights beginning on Days −7 and −6: Nights 1 and 2, respectively. For the next-day residual effects parameters, such as DSST and KSS, their baseline was defined as the assessments on the days following Nights 1 and 2 (i.e., Days −6 and −5, respectively). Missing data were displayed as missing in listings and treated as missing in summaries. No data imputation was performed.

Safety—Subjects' adverse effects ("AEs") were categorized into preferred terms and associated system organ class ("SOC") using the Medical Dictionary for Regulatory Activities ("MedDRA", version 16.1). Treatment-emergent AEs ("TEAEs") were defined as AEs that start after or increase in severity after the first dose of study drug and include next day residual effects, if any. An AE occurring after the first dose of study drug was considered to be a TEAE and was assigned to the most recent treatment administered. Treatment-emergent AEs were summarized by presenting the incidence of AEs for each treatment group by the MedDRA preferred term, nested within SOC for the safety population.

6.3 Example 3: Sleep Efficiency Results

Figure 1:
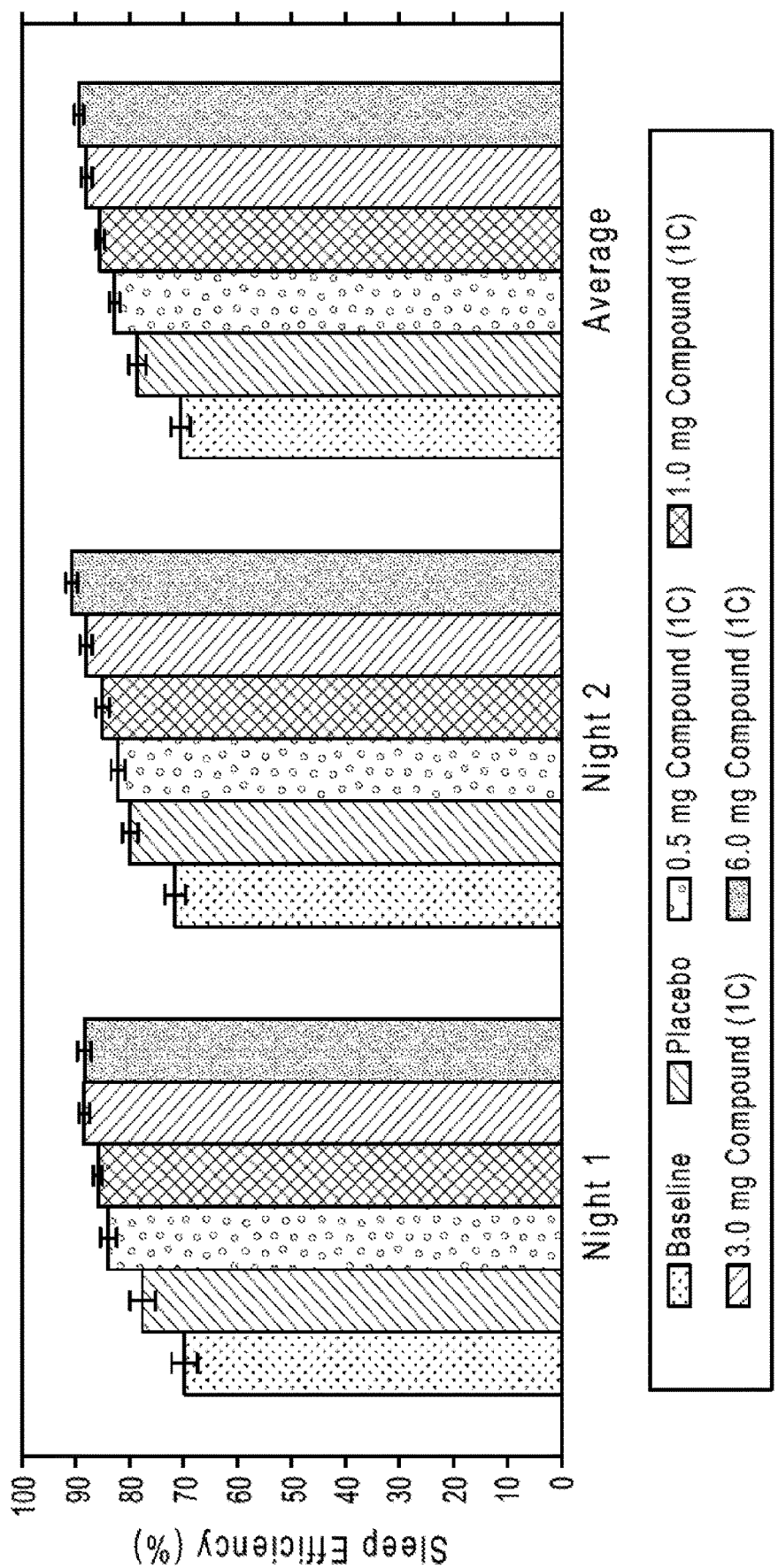
FIG. 1 shows bar charts summarizing the human Sleep Efficiency ("SE") results in Example 3 for the full analysis population for Night 1, Night 2, and the average of Night 1 and Night 2 with the standard error bars as indicated.

SE was expressed as a percentage by multiplying the ratio of TST/TIB by 100. In this study the TIB was 8 hours. The bar chart in FIG. 1 provides a graphical representation of SE for the baseline visit, the period following administration of each of the 4 doses of Compound (1C), and the period following administration of the placebo. The "Night 1" bar represents the mean SE results from the first night of Dosing Periods 1-5 or from the first night of the baseline visit, the "Night 2" bar represents the mean SE results from the second night of Dosing Periods 1-5 or from the second night of the baseline visit, and the "Average" bar represents the mean of SE assessments on all nights of Dosing Periods 1-5 or the baseline visit.

Table 1 below summarizes the SE determination results in connection with the "Average" bars and provides a statistical analysis thereof. The quantity "N" represents the number of subjects administered each dose.

TABLE 1

Sleep Efficiency ("SE") and Statistical Analysis (Full Analysis Population)

| Compound (1C) Dose (mg) | N | Least Squares Means (%) (STDE) | 95% Conf. Intervals of LSMs | Comparison Dose | Difference of Least Squares Means (%) | 95% Conf. Intervals of LSMs Difference | p-Value |
|---|---|---|---|---|---|---|---|
| 0.5 | 30 | 12.1 (1.02) | 10.0, 14.1 | 0.5 mg vs. Placebo | 4.1 | 1.7, 6.6 | 0.001 |
| 1.0 | 30 | 14.7 (1.02) | 12.6, 16.7 | 1.0 mg vs. Placebo | 6.7 | 4.3, 9.2 | <0.001 |
| 3.0 | 29 | 17.6 (1.03) | 15.6, 19.7 | 3.0 mg vs. Placebo | 9.7 | 7.2, 12.1 | <0.001 |
| 6.0 | 30 | 19.0 (1.02) | 16.9, 21.0 | 6.0 mg vs. Placebo | 11.0 | 8.6, 13.5 | <0.001 |
| Placebo | 30 | 7.9 (1.02) | 5.9, 10.0 | N/A | N/A | N/A | N/A |

As is evident from the data in FIG. 1 and Table 1, Sleep Efficiency, an important indication of efficacy that is also clinically meaningful, was significantly increased in all treatment groups, exhibiting a desirable steady increase in the difference of LSMs of 4.1, 6.7, 9.7, and 11.0% for doses of Compound (1C) of 0.5, 1.0, 3.0, and 6.0 mg, respectively. Another important characteristic that is evident from the results in this example is the approximate proportionality of the increase in SE with increasing dose of Compound (1C).

6.4 Example 4: Total Sleep Time Results

Figure 2:
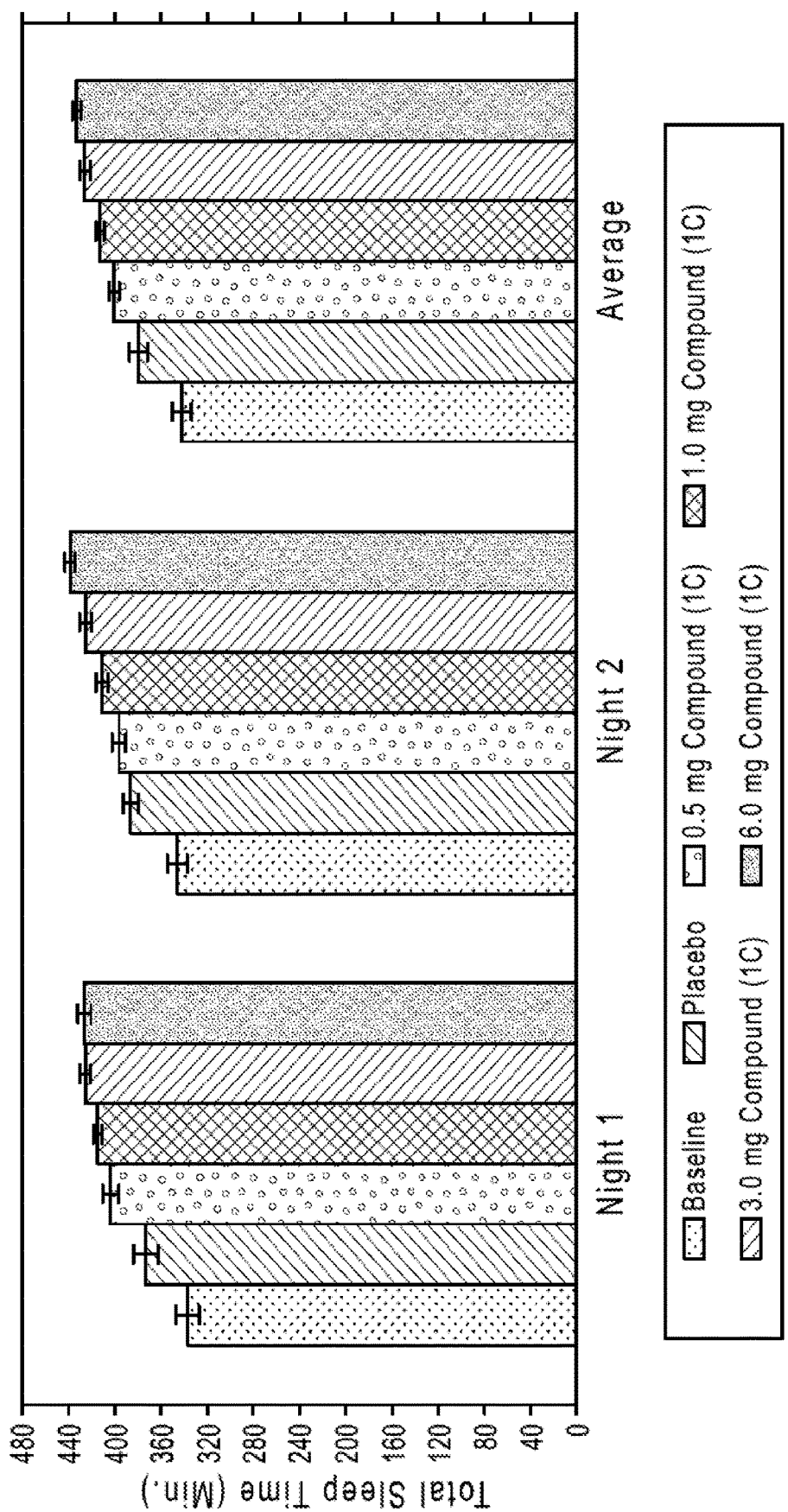
FIG. 2 shows bar charts summarizing the human Total Sleep Time ("TST") results in Example 4 for the full analysis population for Night 1, Night 2, and the average of Night 1 and Night 2 with the standard error bars as indicated.

The bar chart in FIG. 2 provides a graphical representation of TST for the baseline visit, the period following administration of each of the 4 doses of Compound (1C), and the period following administration of the placebo. The "Night 1" bar represents the mean TST results from the first night of Dosing Periods 1-5 or from the first night of the baseline visit, the "Night 2" bar represents the mean TST results from the second night of Dosing Periods 1-5 or from the second night of the baseline visit, and the "Average" bar represents the mean of TST assessments on all nights of Dosing Periods 1-5 or the baseline visit.

Table 2 below summarizes the TST determination results in connection with the "Average" bars and provides a statistical analysis thereof. The quantity "N" represents the number of subjects administered each dose.

TABLE 2

Total Sleep Time ("TST") and Statistical Analysis (Full Analysis Population)

| Compound (1C) Dose (mg) | N | Least Squares Means (min) (STDE) | 95% Conf. Intervals of LSMs | Comparison Dose | Difference of Least Squares Means (min) | 95% Conf. Intervals of LSMs Difference | p-Value |
|---|---|---|---|---|---|---|---|
| 0.5 | 30 | 57.9 (4.88) | 48.2, 67.5 | 0.5 mg vs. Placebo | 19.8 | 8.0, 31.5 | 0.001 |
| 1.0 | 30 | 70.3 (4.88) | 60.7, 80.0 | 1.0 mg vs. Placebo | 32.3 | 20.5, 44.0 | <0.001 |
| 3.0 | 29 | 84.5 (4.96) | 74.7, 94.4 | 3.0 mg vs. Placebo | 46.4 | 34.6, 58.3 | <0.001 |
| 6.0 | 30 | 91.0 (4.88) | 81.3, 100.7 | 6.0 mg vs. Placebo | 52.9 | 41.2, 64.6 | <0.001 |
| Placebo | 30 | 38.1 (4.88) | 28.4, 47.8 | N/A | N/A | N/A | N/A |

As is evident from the data in FIG. 2 and Table 2, Total Sleep Time, another key indication of efficacy that is also clinically meaningful, was significantly increased in all treatment groups, exhibiting a desirable steady increase in the difference of LSMs of 19.8, 32.3, 46.4, and 52.9 minutes for doses of Compound (1C) of 0.5, 1.0, 3.0, and 6.0 mg, respectively. A further important characteristic that is evident from the results in this example is the approximate proportionality of the increase in TST with increasing dose of Compound (1C).

6.5 Example 5: Wake after Sleep Onset Results

Figure 3:
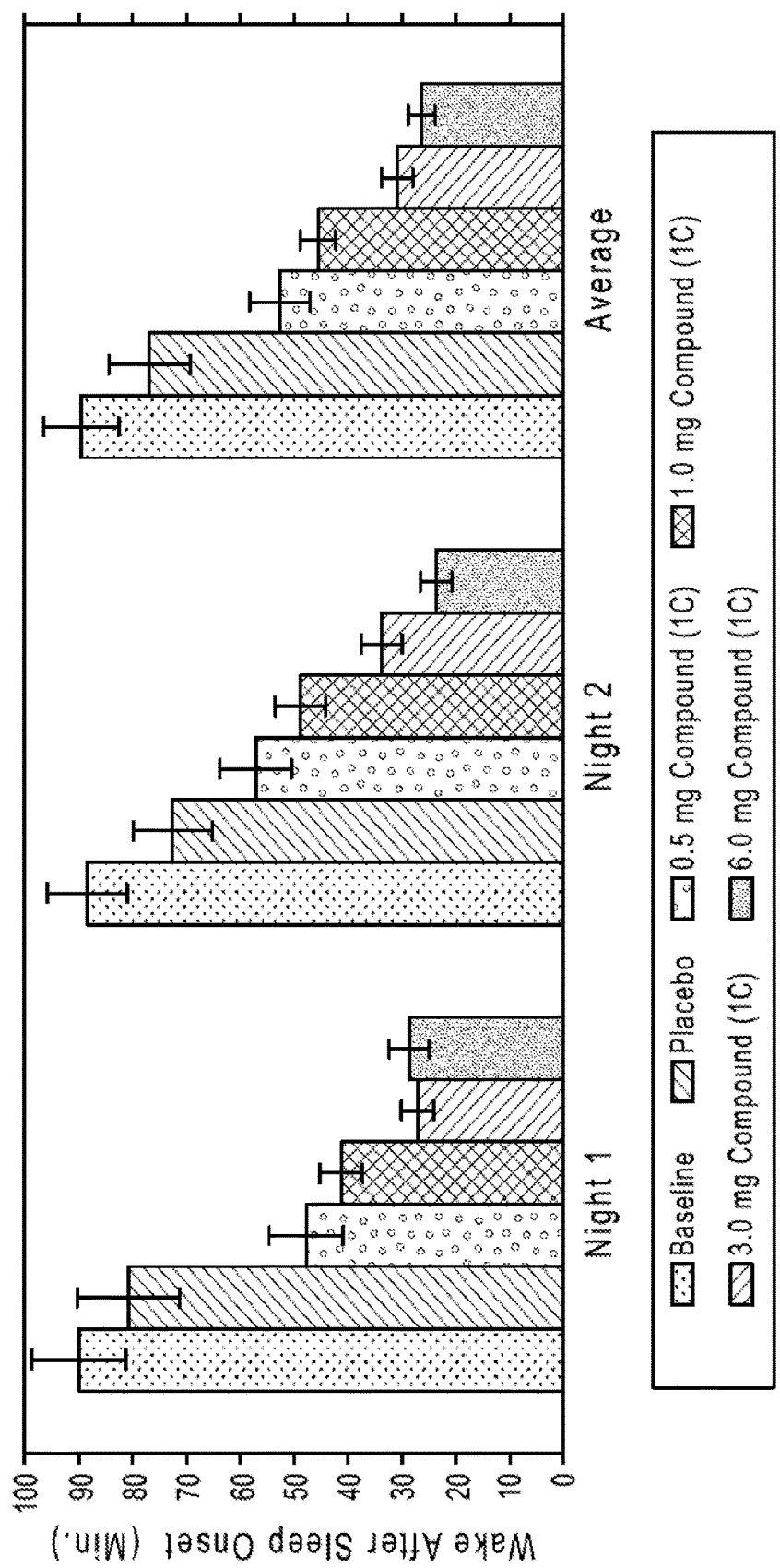
FIG. 3 shows bar charts summarizing the human Wake After Sleep Onset ("WASO") results in Example 5 for the full analysis population for Night 1, Night 2, and the average of Night 1 and Night 2 with the standard error bars as indicated.

The bar chart in FIG. 3 provides a graphical representation of WASO for the baseline visit, the period following administration of each of the 4 doses of Compound (1C), and the period following administration of the placebo. The "Night 1" bar represents the mean WASO results from the first night of Dosing Periods 1-5 or from the first night of the baseline visit, the "Night 2" bar represents the mean WASO results from the second night of Dosing Periods 1-5 or from the second night of the baseline visit, and the "Average" bar represents the mean of WASO assessments on all nights of Dosing Periods 1-5 or the baseline visit.

Table 3 below summarizes the WASO determination results in connection with the "Average" bars and provides a statistical analysis thereof. The quantity "N" represents the number of subjects administered each dose.

As is evident from the data in FIG. 3 and Table 3, Wake after Sleep Onset, another key indication of efficacy that is also clinically meaningful, was significantly decreased in all treatment groups, exhibiting a desirable steady decrease in the difference of LSMs of 24.3, 31.8, 46.4, and 50.8 minutes for doses of Compound (1C) of 0.5, 1.0, 3.0, and 6.0 mg, respectively. A further important characteristic that is evident from the results in this example is the approximate proportionality of the decrease in WASO with increasing dose of Compound (1C).

6.6 Example 6: Latency to Persistent Sleep Results

Figure 4:
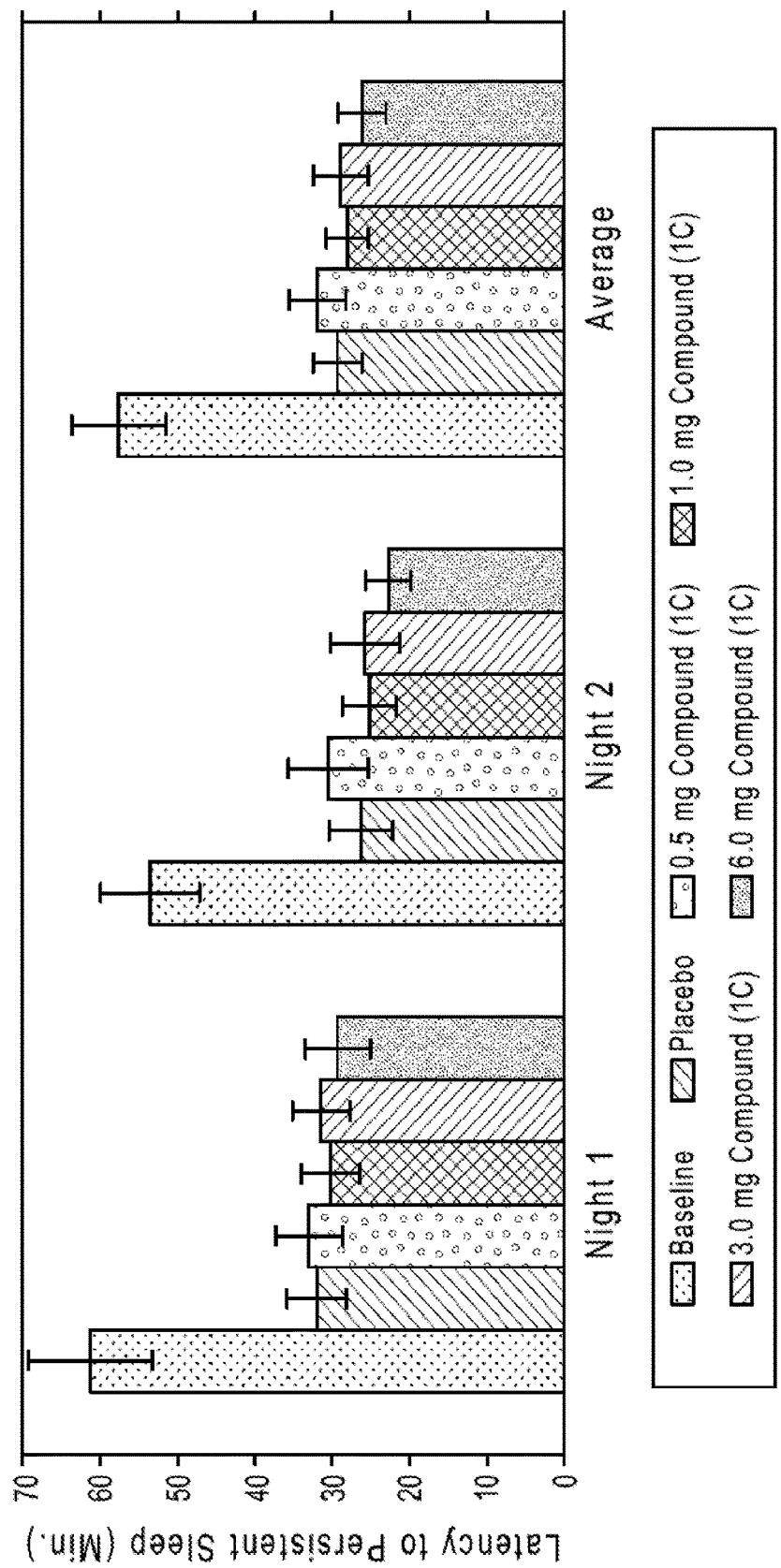
FIG. 4 shows bar charts summarizing the human Latency to Persistent Sleep ("LPS") results in Example 6 for the full analysis population for Night 1, Night 2, and the average of Night 1 and Night 2 with the standard error bars as indicated.

The bar chart in FIG. 4 provides a graphical representation of LPS for the baseline visit, the period following administration of each of the 4 doses of Compound (1C), and the period following administration of the placebo. The "Night 1" bar represents the mean LPS results from the first night of Dosing Periods 1-5 or from the first night of the baseline visit, the "Night 2" bar represents the mean LPS results from the second night of Dosing Periods 1-5 or from the second night of the baseline visit, and the "Average" bar represents the mean of LPS assessments on all nights of Dosing Periods 1-5 or the baseline visit.

Table 4 below summarizes the LPS determination results in connection with the "Average" bars and provides a statistical analysis thereof. The quantity "N" represents the number of subjects administered each dose.

TABLE 3

Wake after Sleep Onset ("WASO") and Statistical Analysis (Full Analysis Population)

| Compound (1C) Dose (mg) | N | Least Squares Means (min) (STDE) | 95% Conf. Intervals of LSMs | Comparison Dose | Difference of Least Squares Means (min) | 95% Conf. Intervals of LSMs Difference | p-Value |
|---|---|---|---|---|---|---|---|
| 0.5 | 30 | −37.1 (4.54) | −46.1, −28.0 | 0.5 mg vs. Placebo | −24.3 | −34.5, −14.2 | <0.001 |
| 1.0 | 30 | −44.5 (4.54) | −53.5, −35.4 | 1.0 mg vs. Placebo | −31.8 | −41.9, −21.6 | <0.001 |
| 3.0 | 29 | −59.1 (4.60) | −68.3, −50.0 | 3.0 mg vs. Placebo | −46.4 | −56.6, −36.2 | <0.001 |
| 6.0 | 30 | −63.5 (4.54) | −72.6, −54.5 | 6.0 mg vs. Placebo | −50.8 | −60.9, −40.7 | <0.001 |
| Placebo | 30 | −12.7 (4.54) | −21.8, −3.7 | N/A | N/A | N/A | N/A |

TABLE 4

Latency to Persistent Sleep ("LPS") and Statistical Analysis (Full Analysis Population)

| Compound (1C) Dose (mg) | N | Least Squares Means (min) (STDE) | 95% Conf. Intervals of LSMs | Dose | Comparison Difference of Least Squares Means (min) | 95% Conf. Intervals of LSMs Difference | p-Value |
|---|---|---|---|---|---|---|---|
| 0.5 | 30 | −25.9 (2.78) | −31.4, −20.4 | 0.5 mg vs. Placebo | 2.6 | −4.0, 9.2 | 0.436 |
| 1.0 | 30 | −29.9 (2.78) | −35.4, −24.4 | 1.0 mg vs. Placebo | −1.4 | −8.0, 5.2 | 0.674 |
| 3.0 | 29 | −29.0 (2.82) | −34.6, −23.4 | 3.0 mg vs. Placebo | −0.5 | −7.2, 6.1 | 0.872 |
| 6.0 | 30 | −31.7 (2.78) | −37.3, −26.2 | 6.0 mg vs. Placebo | −3.2 | −9.8, 3.3 | 0.333 |
| Placebo | 30 | −28.5 (2.78) | −34.0, −23.0 | N/A | N/A | N/A | N/A |

As is evident from the data in FIG. 4 and Table 4, e.g., the p-values, Latency to Persistent Sleep was not significantly different in any of the treatment groups.

6.7 Example 7: Sleep Stage N2 Results

Figure 5:
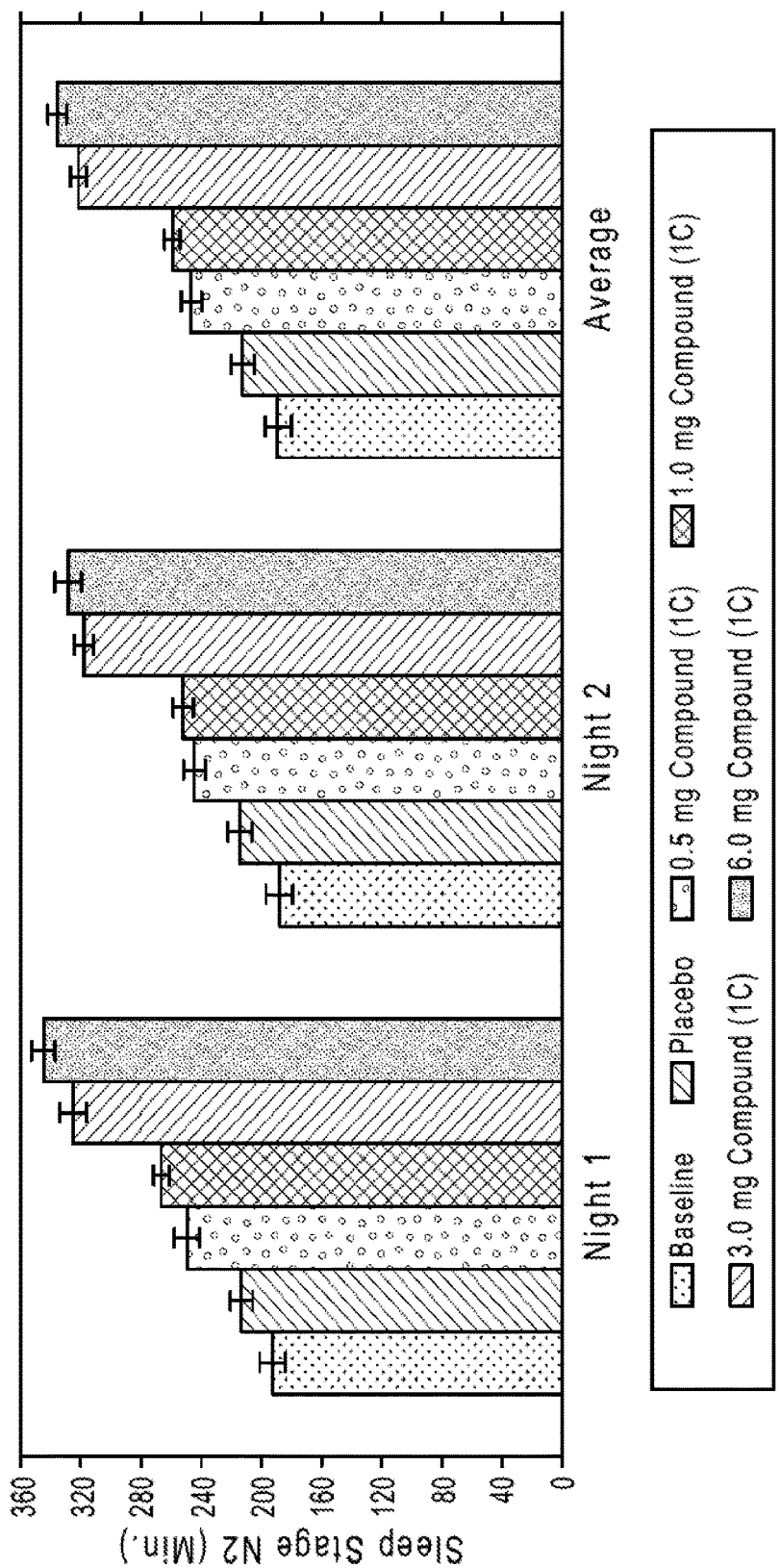
FIG. 5 shows bar charts summarizing the results for the total amount of time spent in sleep Stage N2 in Example 7 for the full analysis population for Night 1, Night 2, and the average of Night 1 and Night 2 with the standard error bars as indicated.

The bar chart in FIG. 5 provides a graphical representation of the amount of time spent in sleep Stage N2 for the baseline visit, the period following administration of each of the 4 doses of Compound (1C), and the period following administration of the placebo. The "Night 1" bar represents the mean the amount of time spent in sleep Stage N2 results from the first night of Dosing Periods 1-5 or from the first night of the baseline visit, the "Night 2" bar represents the mean the amount of time spent in sleep Stage N2 results from the second night of Dosing Periods 1-5 or from the second night of the baseline visit, and the "Average" bar represents the mean of the amount of time spent in sleep Stage N2 on all nights of Dosing Periods 1-5 or the baseline visit.

Table 5 below summarizes the amount of time spent in sleep Stage N2 determination results in connection with the "Average" bars and provides a statistical analysis thereof. The quantity "N" represents the number of subjects administered each dose.

6.8 Example 8: Digit Symbol Substitution Test ("DSST") Results

The well-known DSST is a paper-and-pencil neuropsychological test that explores attention and psychomotor speed and was therefore useful as an indication of next day residual effects, if any. When administered in multiple sessions over time, the DSST provided an objective indication of the change in performance.

Each subject was asked to match symbols with their corresponding digit as follows. Presented with a single page comprising a key table at the top of the page displaying the correspondence between pairs of digits (from 1 to 9) and symbols, each subject filled in up to 93 blank squares with the symbol that was paired with the digit displayed above each blank square. The subject filled in as many squares as possible during the allowed 90 second time limit. The score was determined from the number of correct symbols. An untimed 7 blank square practice opportunity was provided before the 90 second time period began. Six different versions of the test were used to avoid learning effects that could occur if only a single version was used.

The DSST was administered starting approximately ½ hour after lights-on (i.e., about 9 hours post-dosing) and at

TABLE 5

Time Spent in Sleep Stage N2 and Statistical Analysis (Full Analysis Population)

| Compound (1C) Dose (mg) | N | Least Squares Means (min) (STDE) | 95% Conf. Intervals of LSMs | Dose | Comparison Difference of Least Squares Means (min) | 95% Conf. Intervals of LSMs Difference | p-Value |
|---|---|---|---|---|---|---|---|
| 0.5 | 30 | 57.1 (5.53) | 46.1, 68.1 | 0.5 mg vs. Placebo | 33.6 | 20.2, 46.9 | <0.001 |
| 1.0 | 30 | 69.2 (5.53) | 58.2, 80.2 | 1.0 mg vs. Placebo | 45.7 | 32.3, 59.0 | <0.001 |
| 3.0 | 29 | 132.1 (5.6) | 120.9, 143.2 | 3.0 mg vs. Placebo | 108.5 | 95.1, 122.0 | <0.001 |
| 6.0 | 30 | 146.3 (5.5) | 135.4, 157.3 | 6.0 mg vs. Placebo | 122.8 | 109.5, 136.2 | <0.001 |
| Placebo | 30 | 23.5 (5.53) | 12.5, 34.5 | N/A | N/A | N/A | N/A |

As is evident from the data in FIG. 5 and Table 5, the amount of time spent in sleep Stage N2 was significantly increased in all treatment groups, exhibiting a desirable steady increase in the difference of LSMs of 33.6, 45.7, 108.5, and 122.8 minutes for doses of Compound (1C) of 0.5, 1.0, 3.0, and 6.0 mg, respectively. A further important characteristic that is evident from the results in this example is the approximate proportionality of the increase in the amount of time spent in sleep Stage N2 with increasing dose of Compound (1C).

about 1, 3, 4, 5, and 7 hours thereafter following completion of PSG recordings after each night of the baseline visit (Visit 2) and after each night of Dosing Periods 1-5.

Subjects took the DSST for practice during the screening/baseline visit on Day −7.

Figure 6:
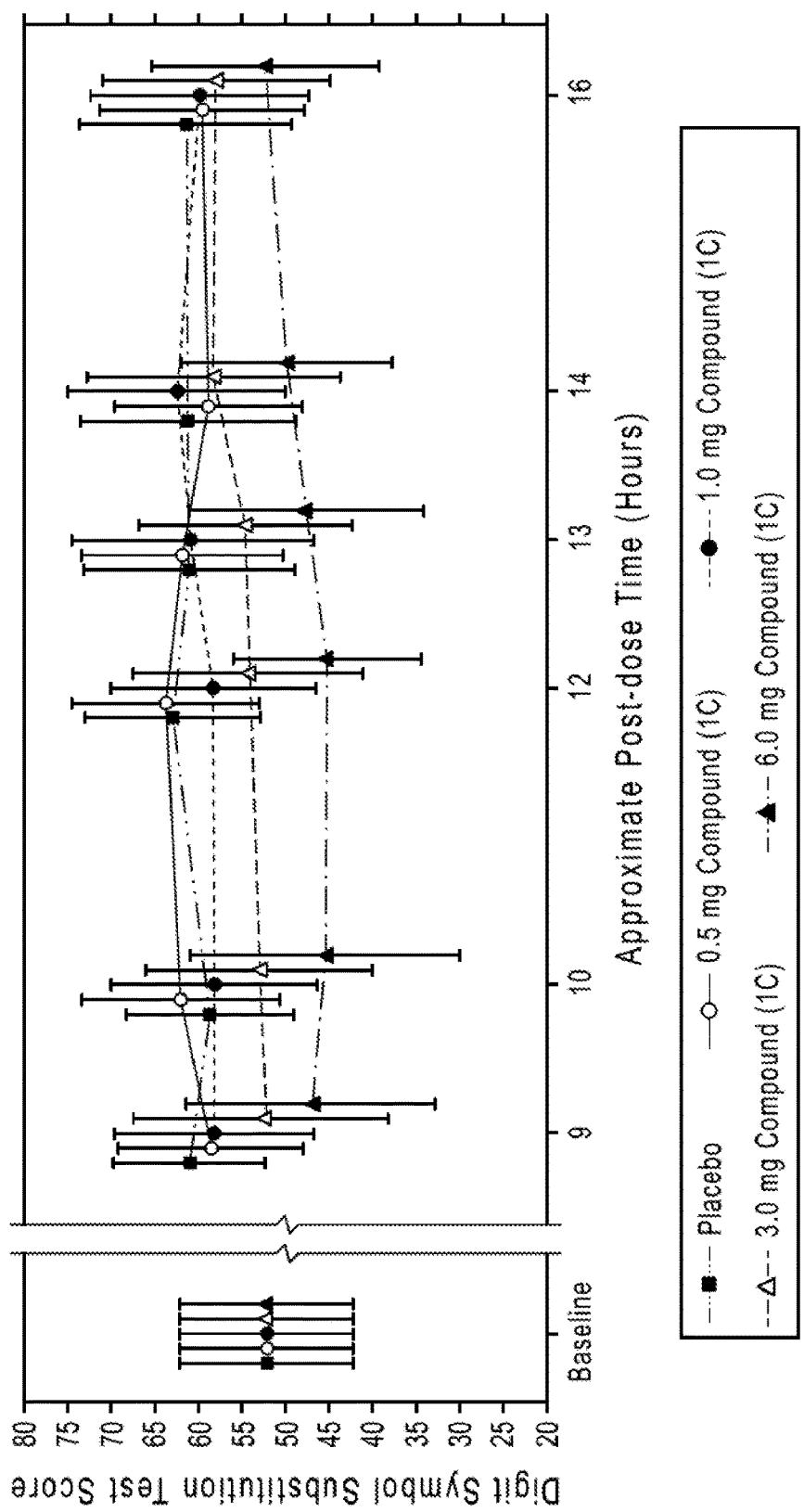
FIG. 6 shows a plot of the Digit Symbol Substitution Test ("DSST") score results in Example 8 for the full analysis population for the average of Night 1 and Night 2 with the standard deviation bars as indicated.

The plot in FIG. 6 provides a graphical representation of the DSST results for (1) the baseline visit, (2) the lights-on period following administration of each of the 4 doses of Compound (1C), and (3) the lights-on period following administration of the placebo. The DSST results shown, other than for the baseline, are the mean results obtained from the DSST scores following all nights of Dosing Periods 1-5 for the indicated dose. The DSST results for the baseline are the mean results obtained following the first and second nights of the baseline visit. Note that for clarity of display purposes, in FIG. 6 many of the test results at each time period, e.g., at approximately ½ hour after lights-on/9 hours post-dosing, were staggered arbitrarily away from the actual time when the test was conducted. Thus, the horizontal time scale is only approximate and does not provide a true indication of the time when each test was actually conducted.

As is evident from the data in FIG. 6, the mean DSST results for the 0.5 mg and 1.0 mg doses of Compound (1C) and the placebo closely tracked one another at all the testing times from about 9 hours to about 16 hours post-dosing, suggesting that there were no next day residual effects attributable to the administration of Compound (1C) at these doses. Marginal negative i.e., unfavorable, deviations from the placebo in the mean DSST results for the 3.0 mg dose of Compound (1C) were evident at only some of the testing times, e.g., at about 9, 10, 12, and 13 hours, from the data in FIG. 6, suggesting that there were minimal next day residual effects attributable to the administration of Compound (1C) at this dose. The trend of further negative deviations from the placebo in the mean DSST results for the 6.0 mg dose of Compound (1C) was evident at each of the testing times from the data in FIG. 6, suggesting that there were some next day residual effects attributable to the administration of Compound (1C) at this dose.

6.9 Example 9: Karolinska Sleepiness Scale ("KSS") Results

The well-known KSS measures, subjectively, the level of a subject's sleepiness at a specific time of the day and was therefore useful as another indication of next day residual effects, if any. The KSS comprised a 9-step scale (ranging from, e.g., "extremely alert" (assigned 1 point) to alert (assigned 3 points) to "neither sleepy nor alert" (assigned 5 points) to "sleepy" (assigned 7 points) to "extremely sleepy" (assigned 9 points)) that characterized sleepiness at a particular time during the day (within 5 minutes of the assessment).

In a paper-and-pencil evaluation, each subject checked a box corresponding to the point of the scale that best characterized their state of drowsiness experienced during the preceding 5 minutes. The KSS evaluation followed the DSST after each night of the baseline visit (Visit 2) and after each night of Dosing Periods 1-5 according to the schedule set out in the previous example.

During the screening/baseline visit, the KSS evaluation was practiced to familiarize the subjects with it.

Figure 7:
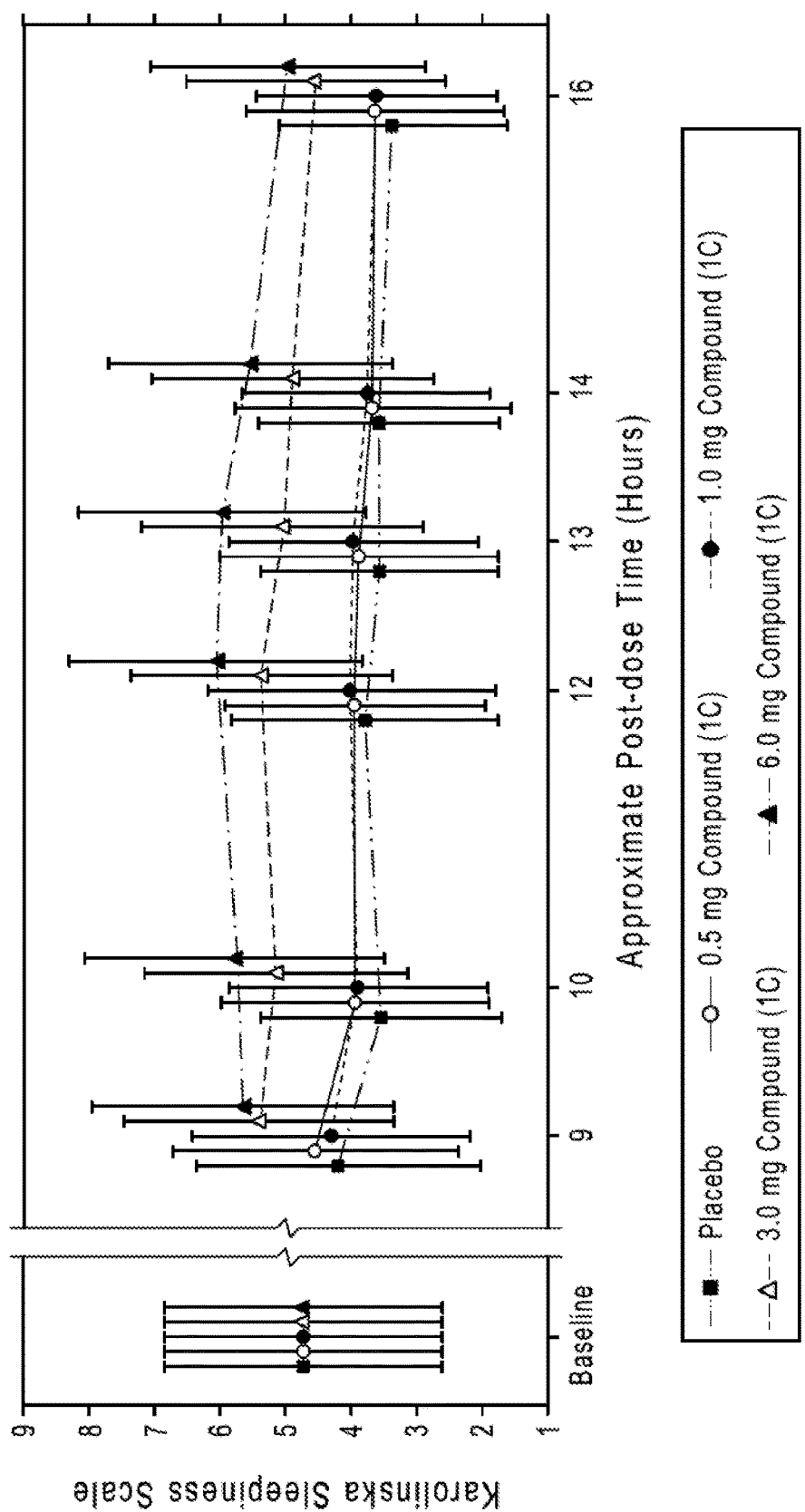
FIG. 7 shows a plot of the Karolinska Sleepiness Scale ("KSS") evaluation results in Example 9 for the full analysis population for the average of Night 1 and Night 2 with the standard deviation bars as indicated.

The plot in FIG. 7 provides a graphical representation of the KSS evaluation results for (1) the baseline visit, (2) the lights-on period following administration of each of the 4 doses of Compound (1C), and (3) the lights-on period following administration of the placebo. The KSS evaluation results shown, other than for the baseline, are the mean results obtained from the KSS evaluation scores following all nights of Dosing Periods 1-5 for the indicated dose. The KSS evaluation results for the baseline are the mean results obtained following the first and second nights of the baseline visit. Note that for clarity of display purposes, in FIG. 7 many of the test results at each time period, e.g., at approximately ½ hour after lights-on/9 hours post-dosing, were staggered arbitrarily away from the actual time when the test was conducted. Thus, the horizontal time scale is only approximate and does not provide a true indication of the time when each test was actually conducted.

As is evident from the data in FIG. 7, the mean KSS evaluation results for the 0.5 mg and 1.0 mg doses of Compound (1C) and the placebo closely tracked one another at all the testing times from about 9 hours to about 16 hours post-dosing, suggesting that there were no next day residual effects attributable to the administration of Compound (1C) at these doses. The trend of positive, i.e., unfavorable, deviations from the placebo in the mean KSS evaluation results for the 3.0 mg and 6.0 mg doses of Compound (1C) was evident at each of the testing times from the data in FIG. 7, suggesting that there were some next day residual effects attributable to the administration of Compound (1C) at these doses.

6.10 Example 10: Administration of Compound (1C) as Compared to Administration of Suvorexant and/or Zolpidem Certain important indications of sleep efficacy and a residual effect, if any, exhibited after administration of Compound (1C) were compared to those exhibited after administration of two FDA-approved drugs prescribed as sleep aids—suvorexant or zolpidem. Literature data for indications of sleep efficacy and attendant residual effects after suvorexant administration, orally administered as BELSOMRA tablets at a single dose of 10 mg, 20 mg, and 40 mg, was available. Literature data for indications of sleep efficacy after zolpidem administration, orally administered as AMBIEN CR tablets, i.e., an extended-release tablet comprising the tartrate salt, in a single dose of 12.5 mg was also available. Additionally, published or unpublished data for indications of sleep efficacy and an attendant residual effect after oral administration of 10 mg of Compound (1C) was also available. These data are summarized in the forest plots in FIG. 8 through FIG. 11. So that the comparisons could be made on an equal basis, only the full analysis population mean Night 1 data for Compound (1C) at 0.5, 1.0, 3.0, and 6.0 mg doses was used in these figures. Additionally, the data shown in FIG. 8 through FIG. 11 are for the treatment effect net of placebo.

Figure 8:
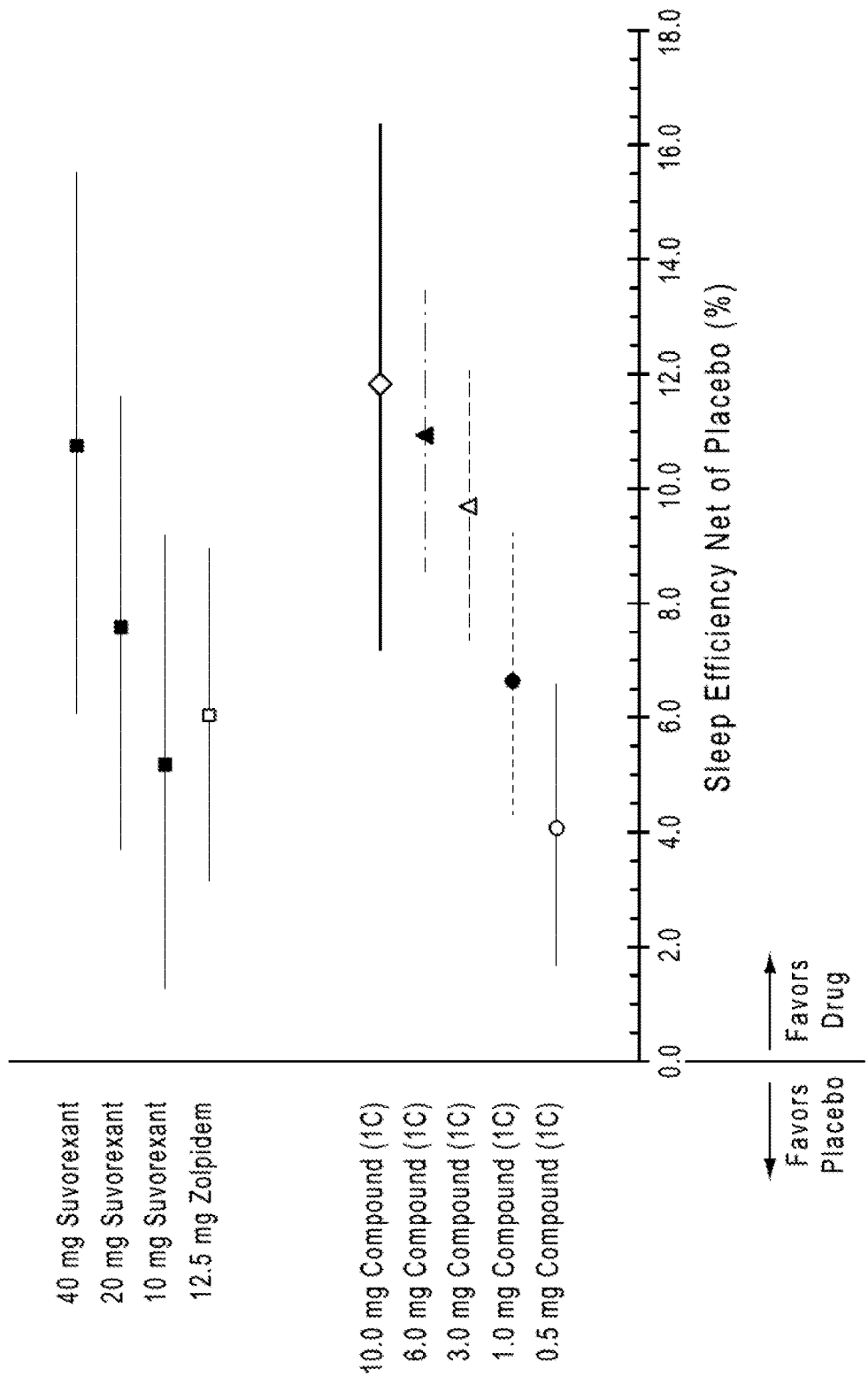
FIG. 8 shows a forest plot of human Sleep Efficiency ("SE") net of placebo for several different doses of Compound (1C) as compared to several doses of suvorexant or zolpidem pursuant to Example 10 with the 95% confidence intervals as indicated.

The effect of each drug on SE is shown in FIG. 8. Note that the mean improvement in SE after administration of only 1.0 mg of Compound (1C) was greater than the mean SE improvement after administration of 12.5 mg of zolpidem, a 12.5 times greater amount by weight, and was greater than the mean SE improvement after administration of 10 mg of suvorexant, a 10 times greater amount by weight when compared with the far lower Compound (1C) dose. Even administration of only 0.5 mg of Compound (1C) provided improved SE. Additionally, the mean improvement in SE after administration of only 6.0 mg of Compound (1C) was comparable to the mean SE improvement after administration of 40 mg of suvorexant, an about 7 times greater amount by weight (40/6=6.7) when compared with the far lower Compound (1C) dose.

Figure 9:
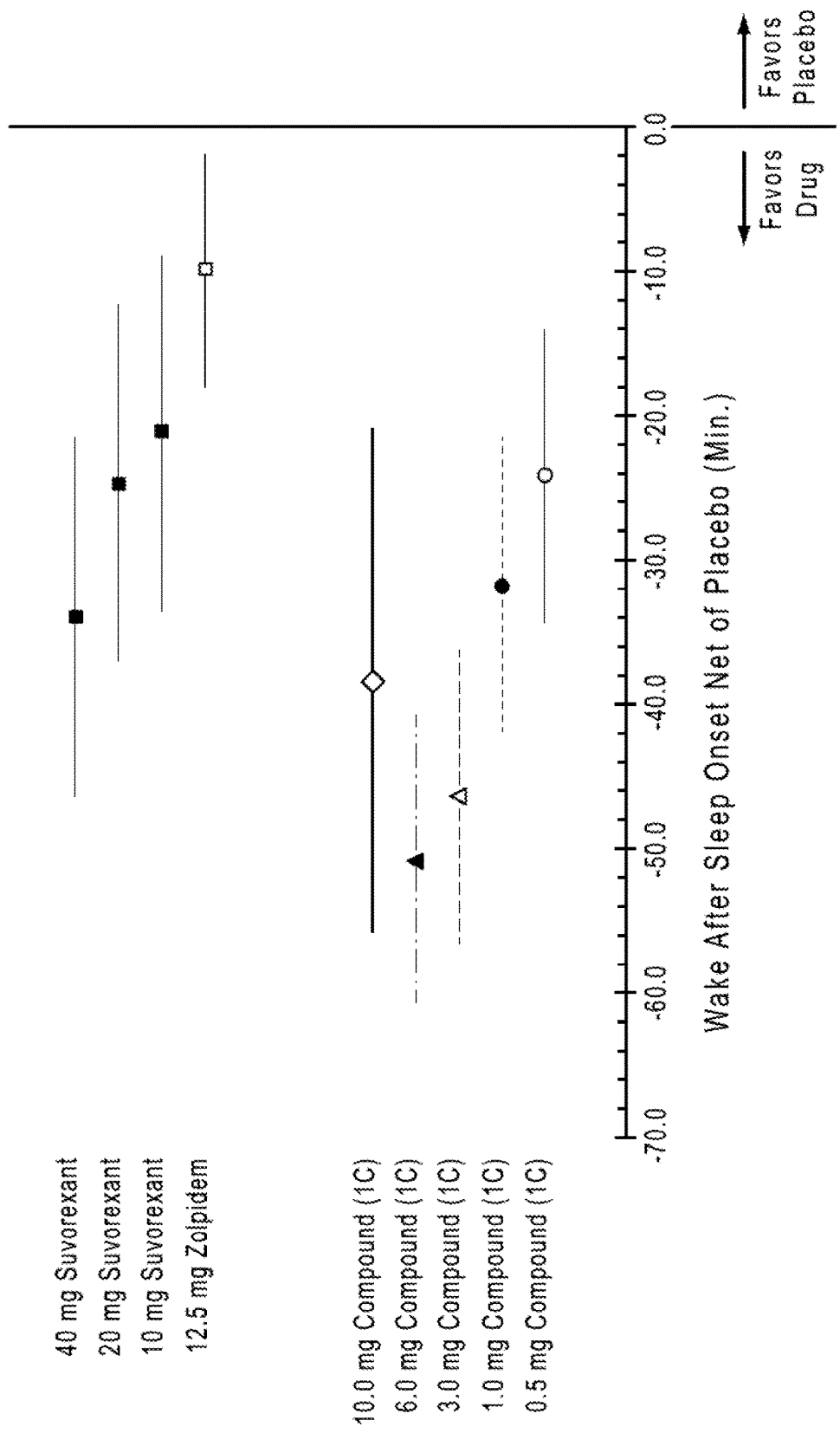
FIG. 9 shows a forest plot of human Wake After Sleep Onset ("WASO") net of placebo for several different doses of Compound (1C) as compared to several doses of suvorexant or zolpidem pursuant to Example 10 with the 95% confidence intervals as indicated.

The effect of each drug on WASO is shown in FIG. 9. Note that the mean improvement in WASO after administration of only 0.5 mg of Compound (1C) was nearly comparable to the mean WASO improvement after administration of 10 mg or 20 mg of suvorexant, an at least 20 or 40 times greater amount by weight, respectively, when compared with the far lower Compound (1C) dose. The mean improvement in WASO after administration of only 1.0 mg of Compound (1C) was nearly comparable to the mean WASO improvement after administration of 40 mg of suvorexant, a 40 times greater amount by weight. Additionally, the mean improvement in WASO after administration of only 0.5 mg of Compound (1C) was far greater than the mean WASO improvement after administration of 12.5 mg zolpidem, a 25 times greater amount by weight (12.5/0.5=25) when compared with the far lower Compound (1C) dose.

Figure 10:
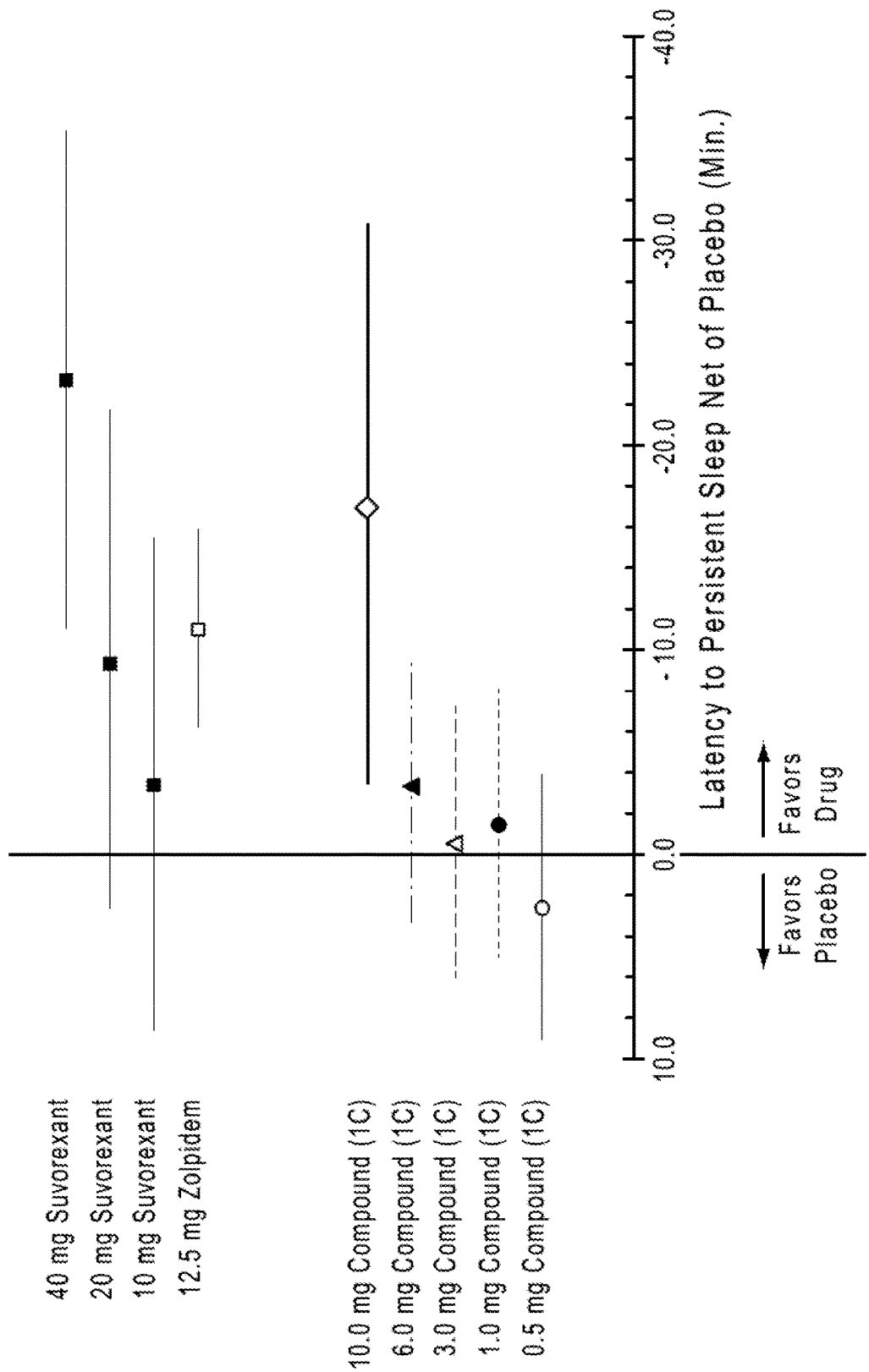
FIG. 10 shows a forest plot of human Latency to Persistent Sleep ("LPS") net of placebo for several different doses of Compound (1C) as compared to several doses of suvorexant or zolpidem pursuant to Example 10 with the 95% confidence intervals as indicated.

The effect of each drug on LPS is shown in FIG. 10. Note that while the mean improvement in LPS after administration of up to 6.0 mg of Compound (1C) was not as great as was provided by 20 mg of suvorexant or 12.5 mg zolpidem, the mean improvement in LPS after administration of 6.0 mg of Compound (1C) was comparable to the LPS improvement provided by the greater 10 mg dose of suvorexant.

Figure 11:
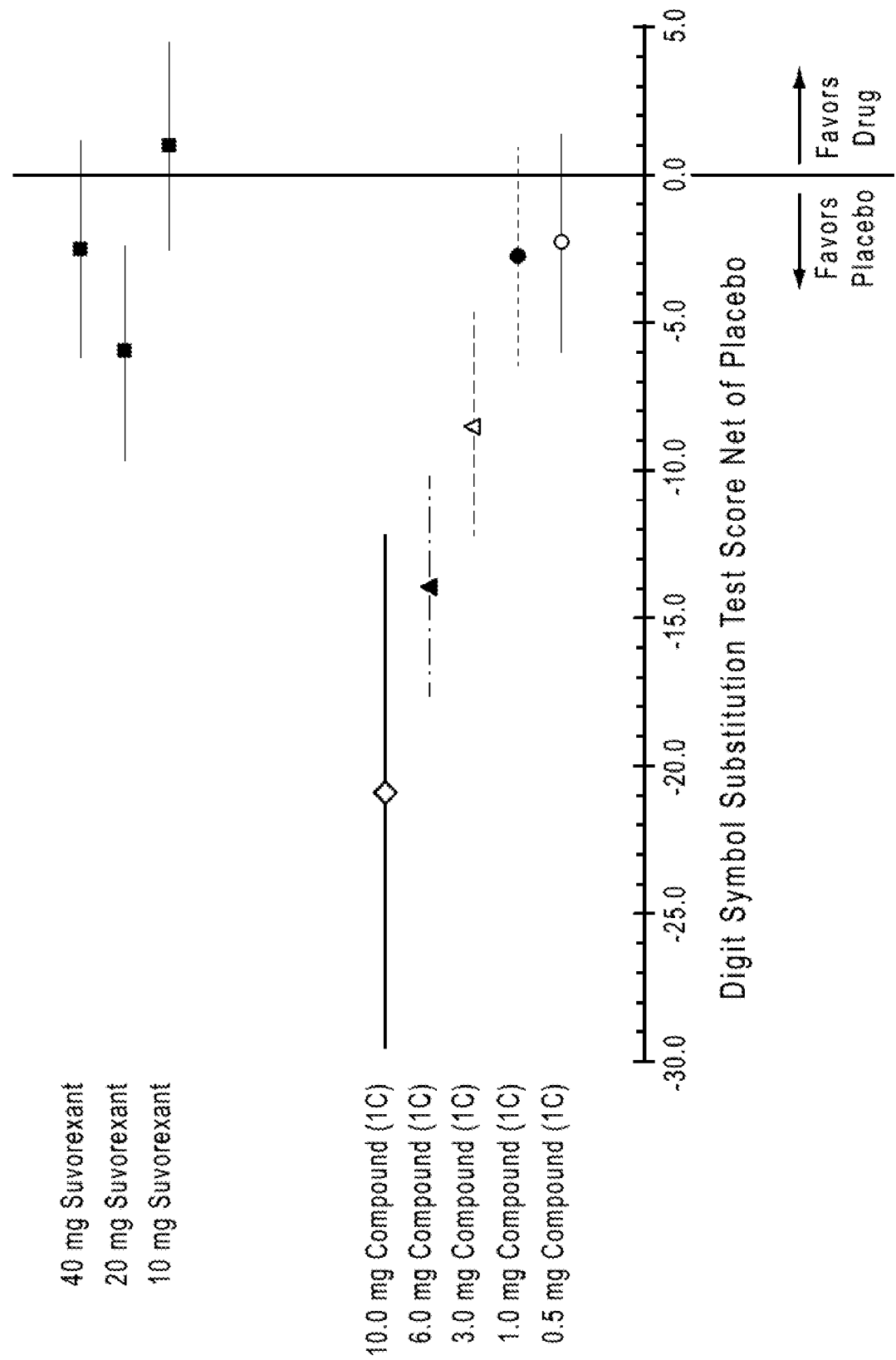
FIG. 11 shows a forest plot of the Digit Symbol Substitution Test ("DSST") score results net of placebo for several different doses of Compound (1C) as compared to several doses of suvorexant pursuant to Example 10 with the 95% confidence intervals as indicated.

The effect of Compound (1C) and suvorexant on the DSST score is shown in FIG. 11. The DSST scores in the figure for Compound (1C) were those obtained at about 9 hours after administration. The DSST scores in the figure for suvorexant were those obtained within 30 to 60 minutes after lights-on. Note that the mean change in DSST score following awakening after administration of 0.5 mg and 1.0 mg of Compound (1C) was small and comparable to the mean DSST score change for 10 mg, 20 mg, and 40 mg of suvorexant.

6.11 Example 11: Human Abuse Potential Study

The objective of this study was to evaluate the abuse potential of single oral doses of Compound (1C) compared to triazolam and placebo in healthy, non-dependent, recreational sedative users. This study was designed as a randomized, single-dose, double-blinded, double dummy, crossover study. The study population was healthy, nondependent recreational polydrug users with a history of Central Nervous System (CNS) depressant use.

Study Design Overview

Figure 12:
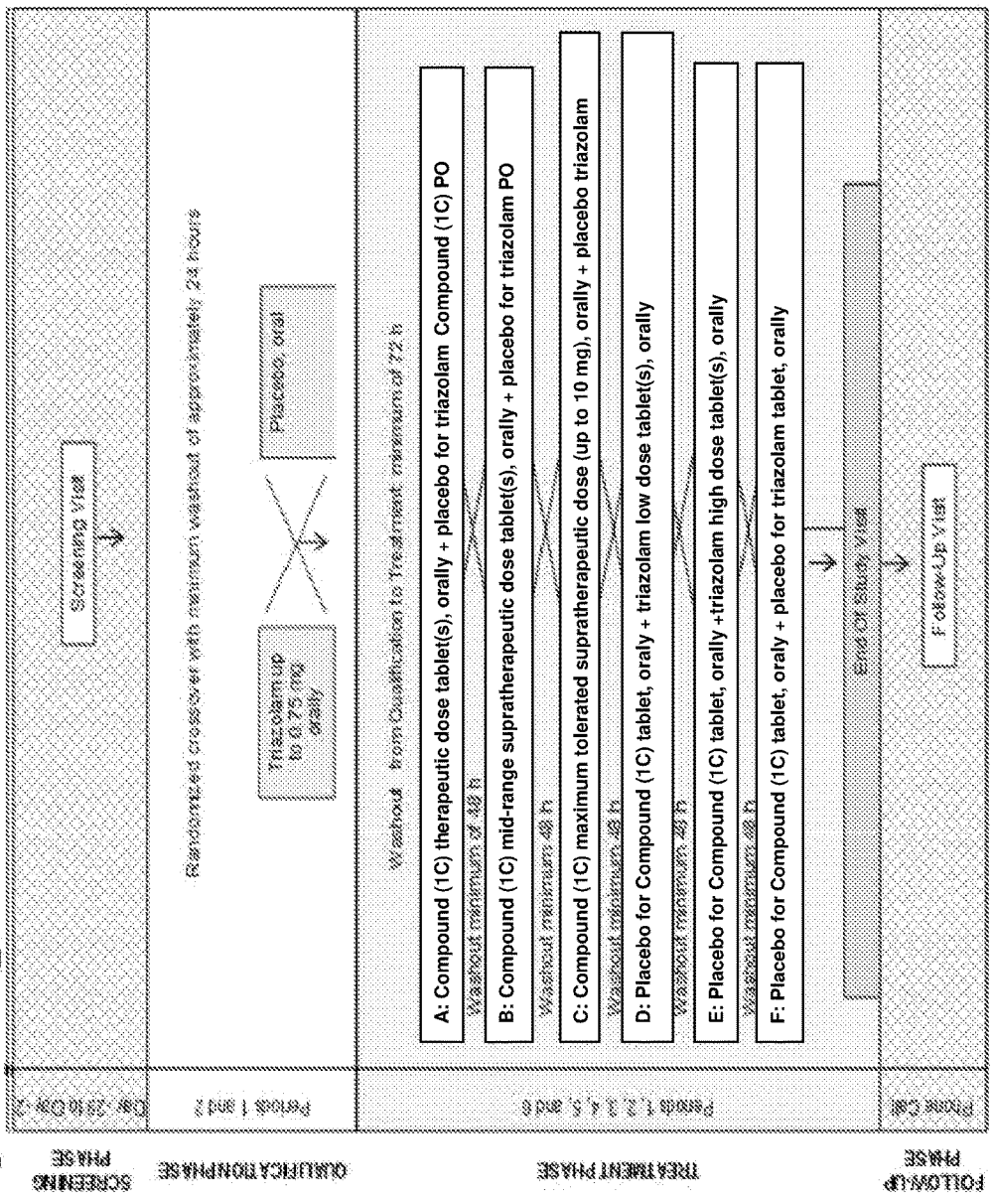
FIG. 12 shows the study design for the Human Abuse Potential Study in Example 11.

The study design is provided in FIG. 12. Subjects were screened no more than 28 days before check-in of period 1. Study drug was administered in each period according to the study randomization schedule. During Qualification, there was a minimum 24 hour washout period between each study drug administration. During the Treatment phase, there was a minimum 48-hour washout period between each study drug administration. Subjects were confined to the unit the day prior to, and for at least approximately 24 hours following, study drug administration during each period. If subjects were discharged between treatment periods, subjects returned to the unit the day prior to dosing.

Subjects had end of study procedures (EOS) performed 24 hours after last dose of study drug or upon discontinuing from the study. Follow-up phone call took place 7-10 days after last dose of study drug. Study duration varied depending on when subjects were dosed during the treatment period.

Part 1, Qualification Phase

The Qualification Phase was designed to ensure that polydrug abusing subjects with self-reported recreational CNS depressant/sedative drug experience were able to tolerate and discriminate between orally administered triazolam tablets and placebo as well as to report positive subjective effects of the drug in a controlled laboratory setting. This phase was also used to exclude "placebo responders", i.e., subjects who report subjective effects of placebo. This phase also helped familiarize subjects with, and trained them in the use of, various scales and questionnaires that measure subjective effects.

Part 2, Treatment Phase

The comparators in an abuse potential study are typically controlled substances from the same pharmacologic class as the investigational drug. However, Compound (1C) is a novel drug class for which no controlled substances/drugs of abuse are available for comparison. Subjective AEs observed in clinical trials of Compound (1C) include primarily somnolence and sedation, indicating a potential sedative effect of the drug. There was no evidence of other effects of interest to abusers, such as perceptual disturbances or stimulation. In addition, a published drug discrimination study of a N/OFQ receptor full agonist demonstrated dose-dependent partial generalization to a benzodiazepine, indicating some similarities between full agonists at the N/OFQ receptor and sedative drugs (Saccone Pa., Zelenock K A, Lindsey A M, Sulima A, Rice K C, Prinssen E P, Wichmann J, Woods J H. "Characterization of the Discriminative Stimulus Effects of a NOP Receptor Agonist Ro 64-6198 in Rhesus Monkeys." *J Pharmacol Exp Ther.* 2016 April; 357(1):17-23). Therefore, triazolam, a short-acting benzodiazepine with a similar PK profile as Compound (1C) and indicated for insomnia (in line with a potential use for Compound (1C)), was selected as the positive control. Time to maximum concentration for Compound (1C) tablets and triazolam tablets administered orally, respectively, is approximately 1.5 hours and 1.3 hours. Placebo control was used to establish the frequency and magnitude of changes in clinical endpoints that may occur in the absence of active treatment as well as to minimize subject and investigator bias.

In all of the study phases, treatments were blinded to the greatest extent possible to reduce potential bias during data collection and evaluation of clinical endpoints. Because study subjects were recreational drug users and familiar with the effects of the drug substances being studied, the double-dummy technique was be used in the Treatment Phase to maintain blinding. Subjects received tablets orally in each treatment period. Placebo was matched in size and shape to each of the tablet types, and a method to blind subjects will be employed.

For each phase, subjects received treatments according to the randomization schema. During the Treatment Phase, subjects were be randomized to 1 of sequences in a 6×6 Williams square crossover design.

Compound (1C) was administered at a dose of 1 mg (therapeutic dose), 6 mg (mid-range supratherapeutic dose), or 10 mg (maximum supratherapeutic dose). Compound (1C) was administered orally in an immediate release tablet comprising the pharmaceutically acceptable excipients croscarmellose sodium (FMC Health and Nutrition, Philadelphia, Pa.), hydroxypropylcellulose (Ashland Inc., Covington, Ky.), microcrystalline cellulose (Dupont, Chicago, Ill.), mannitol (SPI Pharma, Wilmington, Del.), magnesium stearate (PlusPharma Inc., Vista, Calif.), and sodium lauryl sulfate (BASF Corp, Upper St. Clair, Pa.). To reach the appropriate study dose, each subject was administered one or more tablets containing 0.5 mg, 1.0 mg, 3.0 mg, or 6.0 mg of Compound (1C), with each subject dosed about 30 minutes before their median habitual bedtime. Placebo tablets matching the Compound (1C) tablets were orally administered in the same way. The placebo tablets comprised the above-described pharmaceutically acceptable excipients but with no Compound (1C). Triazolam was administered at a dose of 0.5 or 1 mg. Trial endpoints are provided below.

Figure 13:
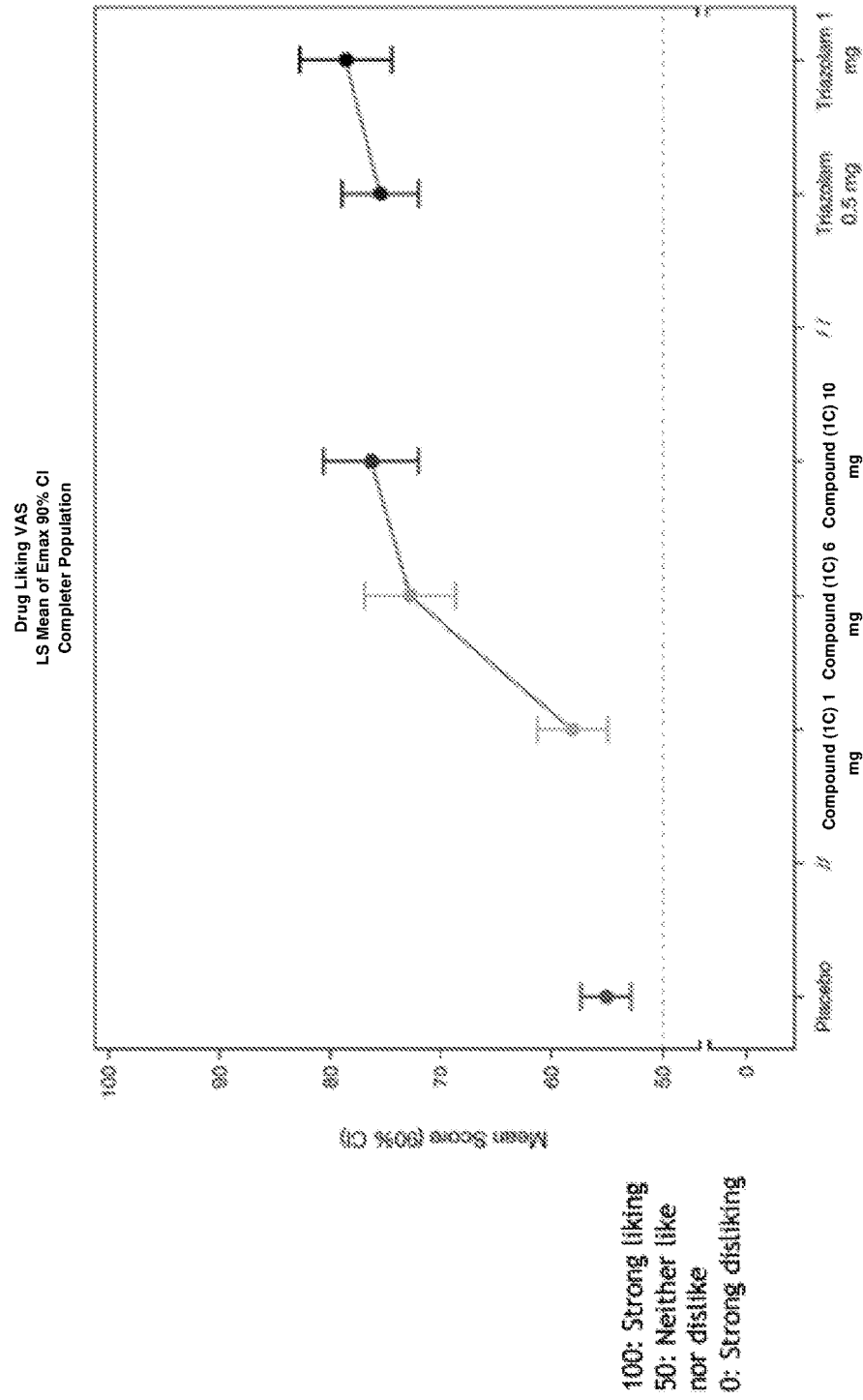
FIG. 13 shows a plot of drug liking response, peak effect ($E_{max}$), to Compound (1C) at doses of 1 mg, 6 mg, and 10 mg, triazolam at doses of 0.5 mg and 1.0 mg, and placebo in Example 11.

Peak Maximum Effect ($E_{max}$) for Drug Liking ("at this moment") visual analog scale ("VAS"), was measured by study participants providing a score on a 100 point bipolar scale with 100 as strong liking, 50 as the neutral point of neither liking nor disliking, and 0 as strong disliking. Results are provided in FIG. 13.

Figure 14:
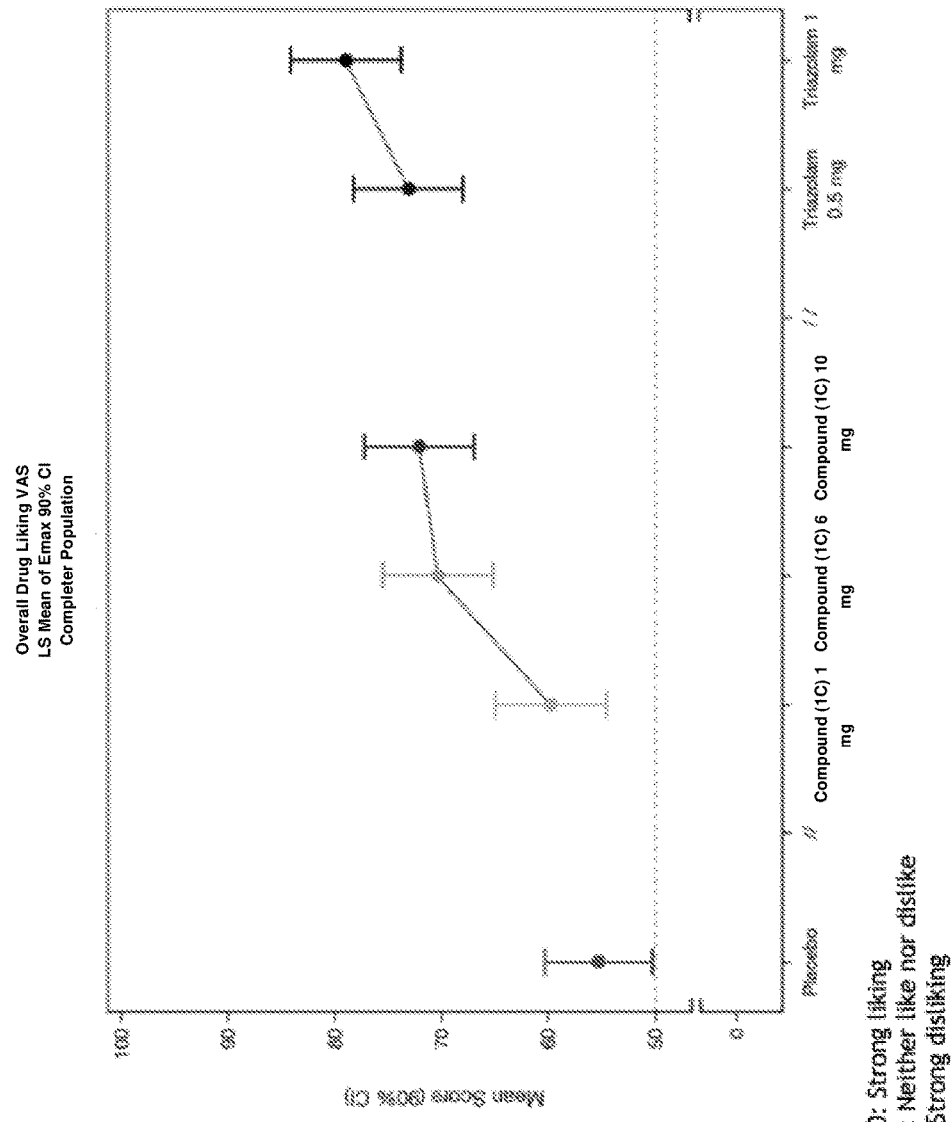
FIG. 14 shows a plot of drug liking response, overall drug liking, to Compound (1C) at doses of 1 mg, 6 mg, and 10 mg, triazolam at doses of 0.5 mg and 1.0 mg, and placebo in Example 11.

Overall Drug Liking VAS was measured by study participants providing a score on a 100 point bipolar scale with 100 as strong liking, 50 as the neutral point of neither liking nor disliking, and 0 as strong disliking. Results are provided in FIG. 14.

Figure 15:
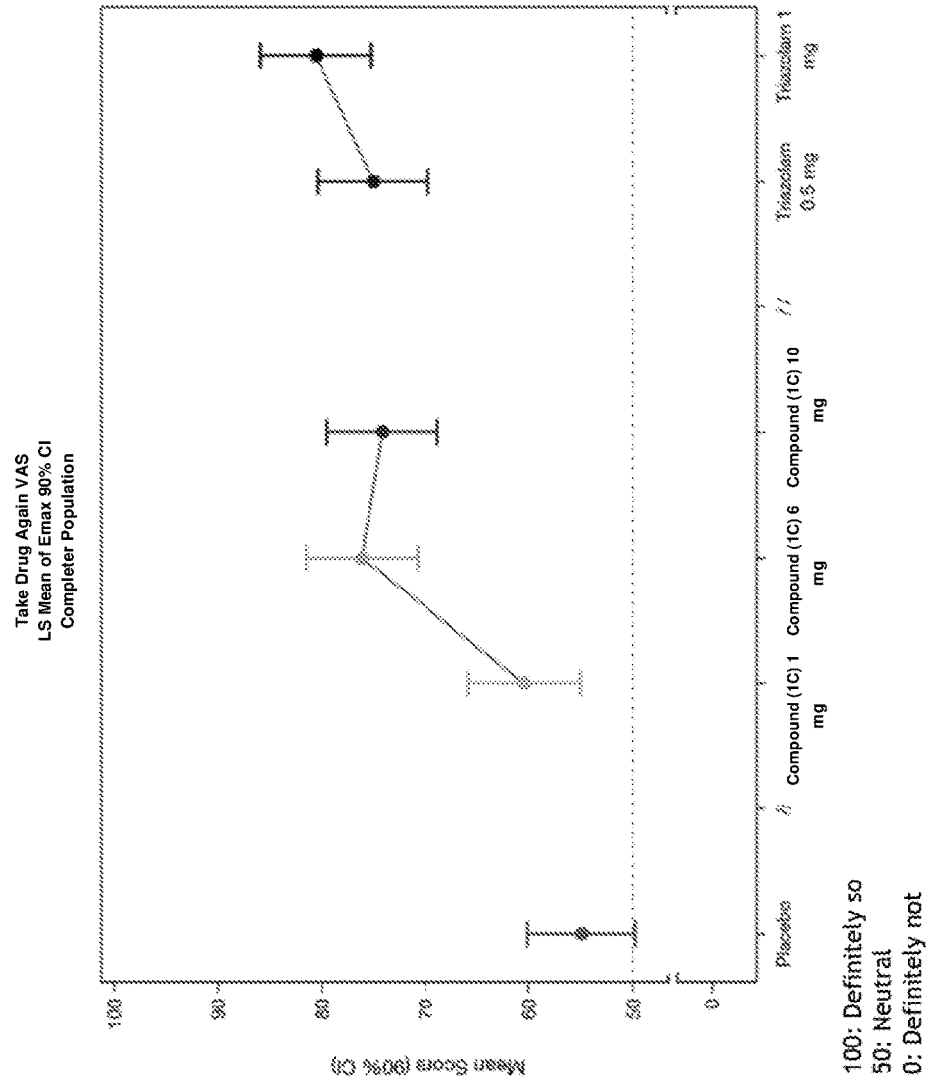
FIG. 15 shows a plot of drug liking response, take drug again effect, to Compound (1C) at doses of 1 mg, 6 mg, and 10 mg, triazolam at doses of 0.5 mg and 1.0 mg, and placebo in Example 11.

Take Drug Again Effect was measured by study participants providing a score on a 100 point bipolar scale with 100 definitely so, 50 as the neutral point, and 0 as definitely not. Results are provided in FIG. 15.

Figure 16:
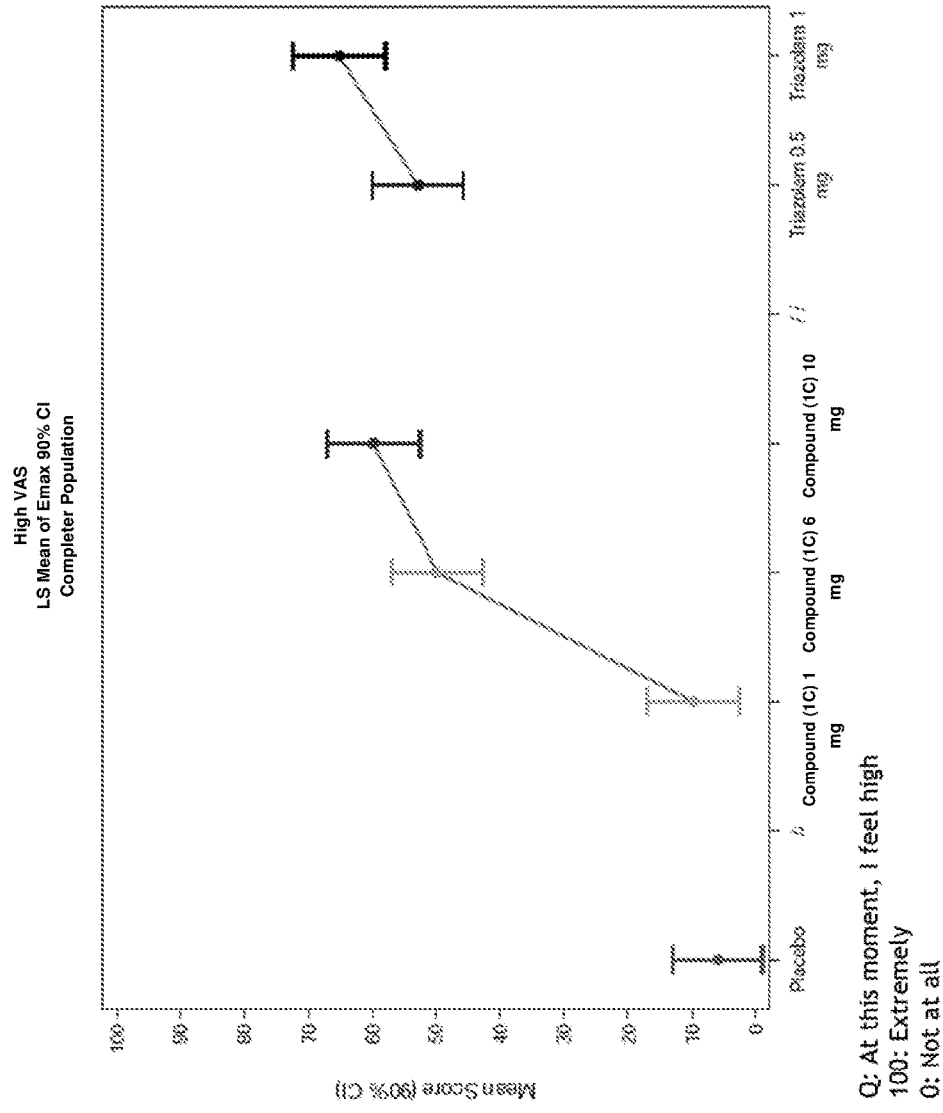
FIG. 16 shows a plot of drug liking response, high drug effect, to Compound (1C) at doses of 1 mg, 6 mg, and 10 mg, triazolam at doses of 0.5 mg and 1.0 mg, and placebo in Example 11.

High Drug Effect was measured by study participants providing a score on a 100 point bipolar scale regarding whether the participant felt a high at the moment with 100 as feeling extremely high and 0 as not at all. Results are provided in FIG. 16.

Figure 17:
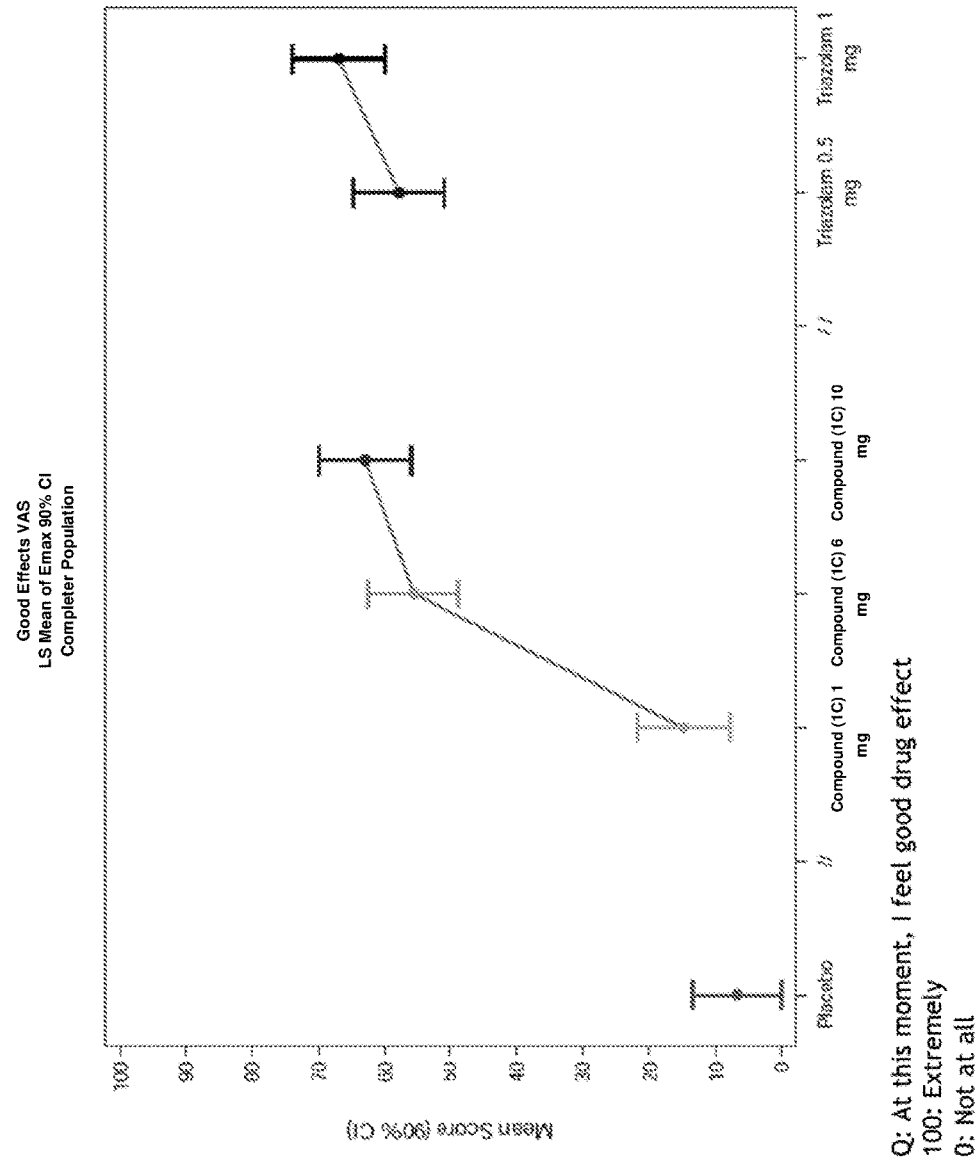
FIG. 17 shows a plot of drug liking response, good drug effect, to Compound (1C) at doses of 1 mg, 6 mg, and 10 mg, triazolam at doses of 0.5 mg and 1.0 mg, and placebo in Example 11.

Good Drug Effect was measured by study participants providing a score on a 100 point bipolar scale regarding whether the participant felt a good drug effect at the moment with 100 as feeling an extremely good drug effect and 0 as not at all. Results are provided in FIG. 17.

Figure 18:
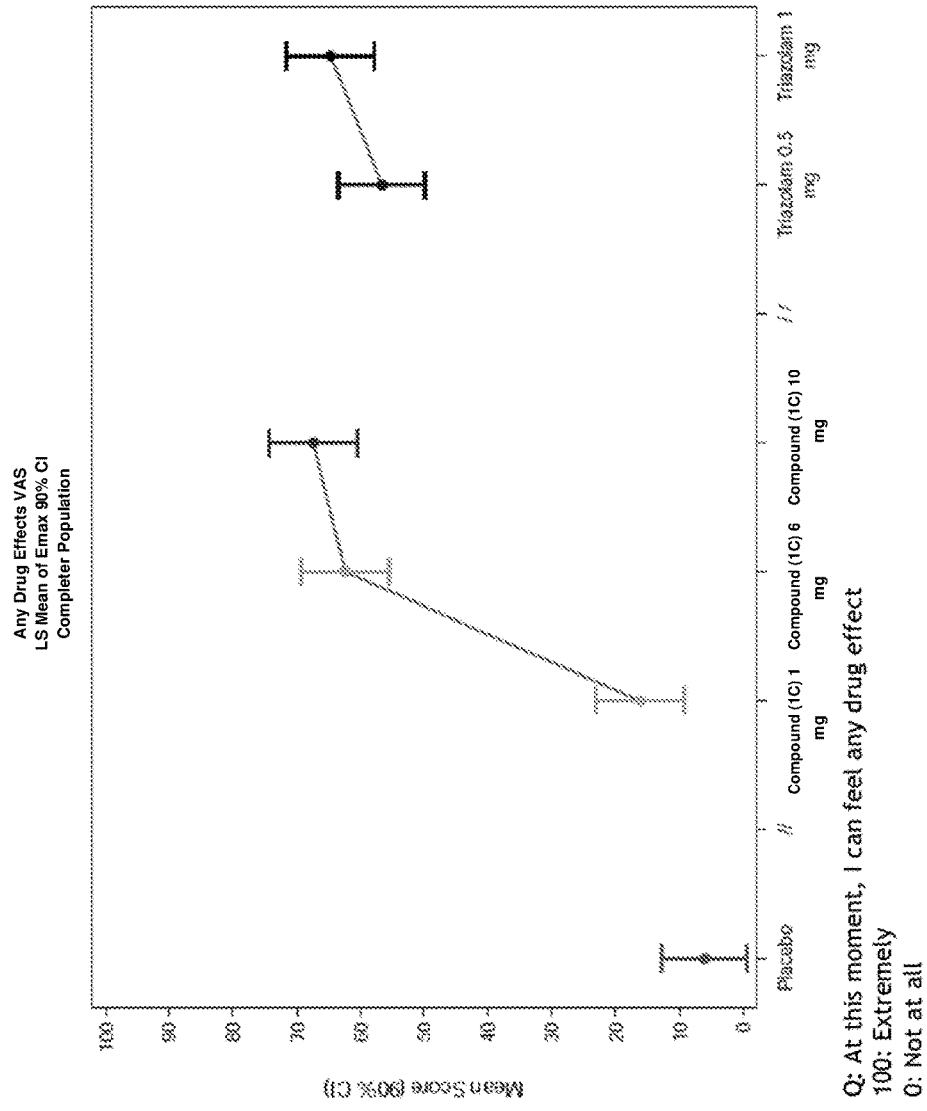
FIG. 18 shows a plot of drug liking response, any drug effect, to Compound (1C) at doses of 1 mg, 6 mg, and 10 mg, triazolam at doses of 0.5 mg and 1.0 mg, and placebo in Example 11.

Any Drug Effect was measured by study participants providing a score on a 100 point bipolar scale regarding whether the participant felt any drug effect at the moment with 100 as feeling an extreme drug effect and 0 as not at all. Results are provided in FIG. 18.

Figure 21:
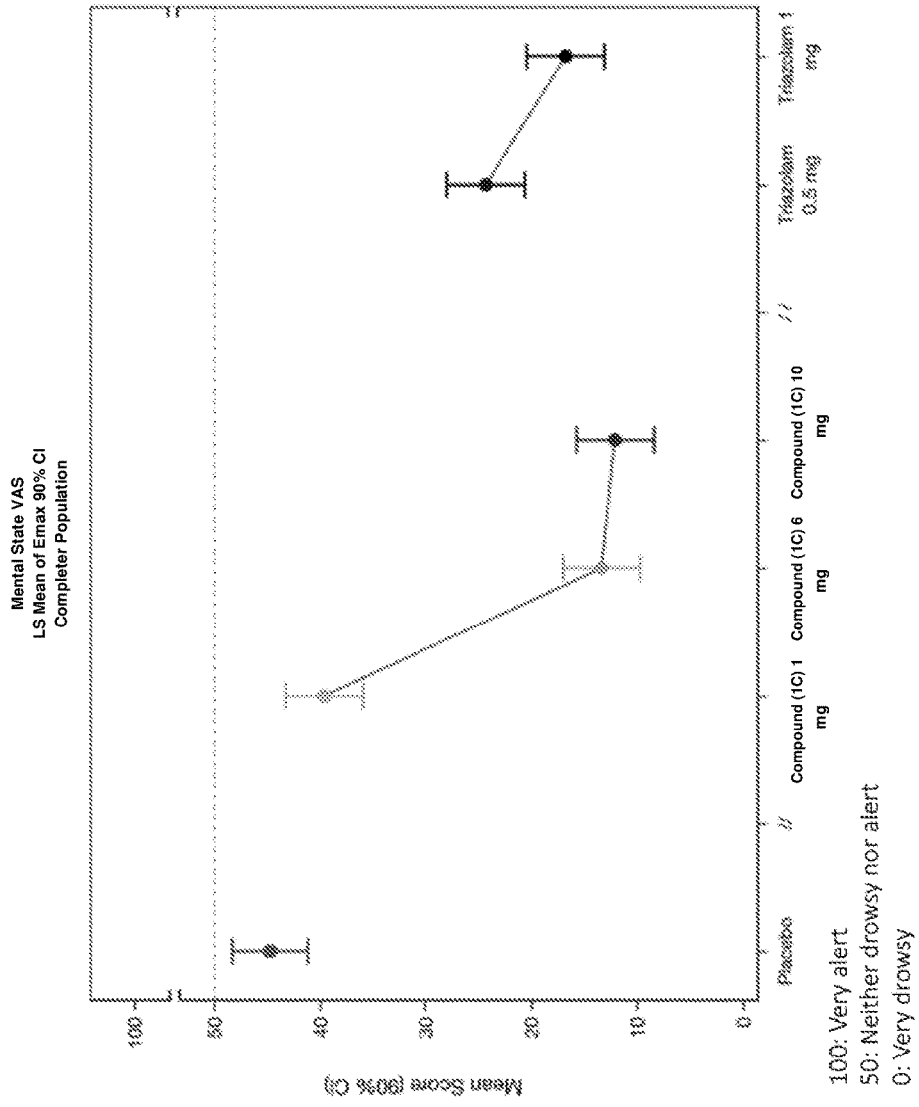
FIG. 21 shows a plot of subjective sedative effects, alertness/drowsiness, to Compound (1C) at doses of 1 mg, 6 mg, and 10 mg, triazolam at doses of 0.5 mg and 1.0 mg, and placebo in Example 11.

Alertness/Drowsiness results are shown in FIG. 21, and Agitation/Relaxation results are shown in FIG. 22.

The assessment of drug liking was chosen as one of the primary measures in the current study because the degree of subject liking is considered one of the most sensitive indices of abuse potential (Balster R L, Bigelow G E. "Guidelines and methodological reviews concerning drug abuse liability assessment." Drug Alcohol Depend. 2003; 70(3 Suppl):S13-40; Carter, Lawrence et al. "Relative Abuse Liability of Indiplon and Triazolam in Humans: A Comparison of Psychomotor, Subjective, and Cognitive Effects." *Journal of Biopharmaceutical Statistics*. 2007; 322. 749-759). The "at this moment" Drug Liking VAS and the Overall Drug Liking VAS assess slightly different aspects of drug liking.

The "at this moment" Drug Liking VAS assesses the subject's liking of the drug at the moment the question was asked, as it may be less subject to recall bias, and is expected to be useful for understanding the time-course of the drug effects. VAS items were displayed on 2 screen images. Using a mouse, the subject positioned the cursor over the small vertical box ("slider") and clicked on it to move it left or right on a scale of 0 to 100. To register the response, the subject then pressed the "OK" button that appeared below the horizontal line. A score of "0" represents a "Strong disliking" and a score of "100" represents a "Strong liking", while a score of 50 represents "Neither like nor dislike".

The Overall Drug Liking VAS and Take Drug Again VAS are thought to assess "global" drug effects and the subject's willingness to take the drug again (i.e., consider subjective effects over the whole course of the experience, including any carryover effects) and have the additional advantage that the subject is generally sober by the time of the assessment (i.e., end of day and/or next day). VAS items were displayed on 2 screen images. Using a mouse, the subject positioned the cursor over the small vertical box ("slider") and clicked on it to move it left or right on a scale of 0 to 100. To register the response, the subject then pressed the "OK" button that appeared below the horizontal line. For the majority of these VAS, 0=Not at all and 100=Extremely. For Take Drug Again VAS, a score of "0" represents "Definitely not" and a score of "100" represents "Definitely so", while 50=Neutral (don't care).

Other VAS items measured positive, negative, and other subjective effects to assess the pharmacologic response to the study drugs. Good and Bad Effects VAS was included as a bipolar assessment, in addition to the unipolar Good Effects VAS and Bad Effects VAS, as the relative salience of these 2 opposing effects at a given moment may not be as easily interpreted when taking only the unipolar Good Effects VAS and Bad Effects VAS into consideration. High, Alertness/Drowsiness, Agitation/Relaxation, Any Effects, are expected to provide additional meaningful information about drug effects.

For the Alertness/Drowsiness VAS score, using a mouse, the subject positioned the cursor over the small vertical box ("slider") and clicked on it to move it left or right on a scale of 0 to 100. To register the response, the subject then pressed the "OK" button that appeared below the horizontal line. A score of "0" represents "Very drowsy", a score of 50 represents "neutral, Neither drowsy nor alert" and a score of "100" represents "Very alert".

For the agitation/Relaxation VAS score, using a mouse, the subject positioned the cursor over the small vertical box ("slider") and clicked on it to move it left or right on a scale of 0 to 100. To register the response, the subject then pressed the "OK" button that appeared below the horizontal line. A score of "0" represents "Very relaxed", a score of 50 represents "neutral, Neither relaxed nor agitated" and a score of "100" represents "Very agitated".

Figure 19:
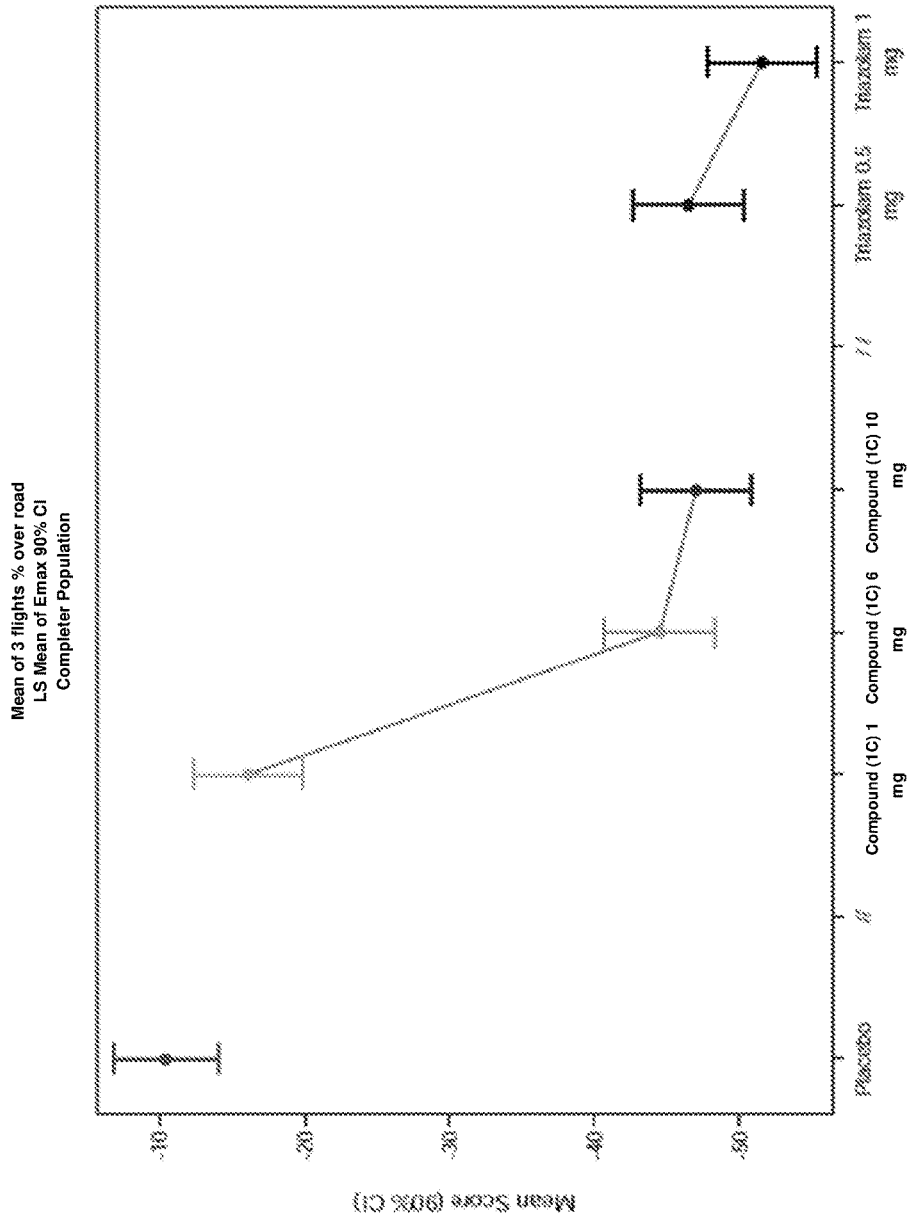
FIG. 19 shows a plot of psychomotor performance, divided attention test ("DAT"), to Compound (1C) at doses of 1 mg, 6 mg, and 10 mg, triazolam at doses of 0.5 mg and 1.0 mg, and placebo in Example 11.
Figure 20:
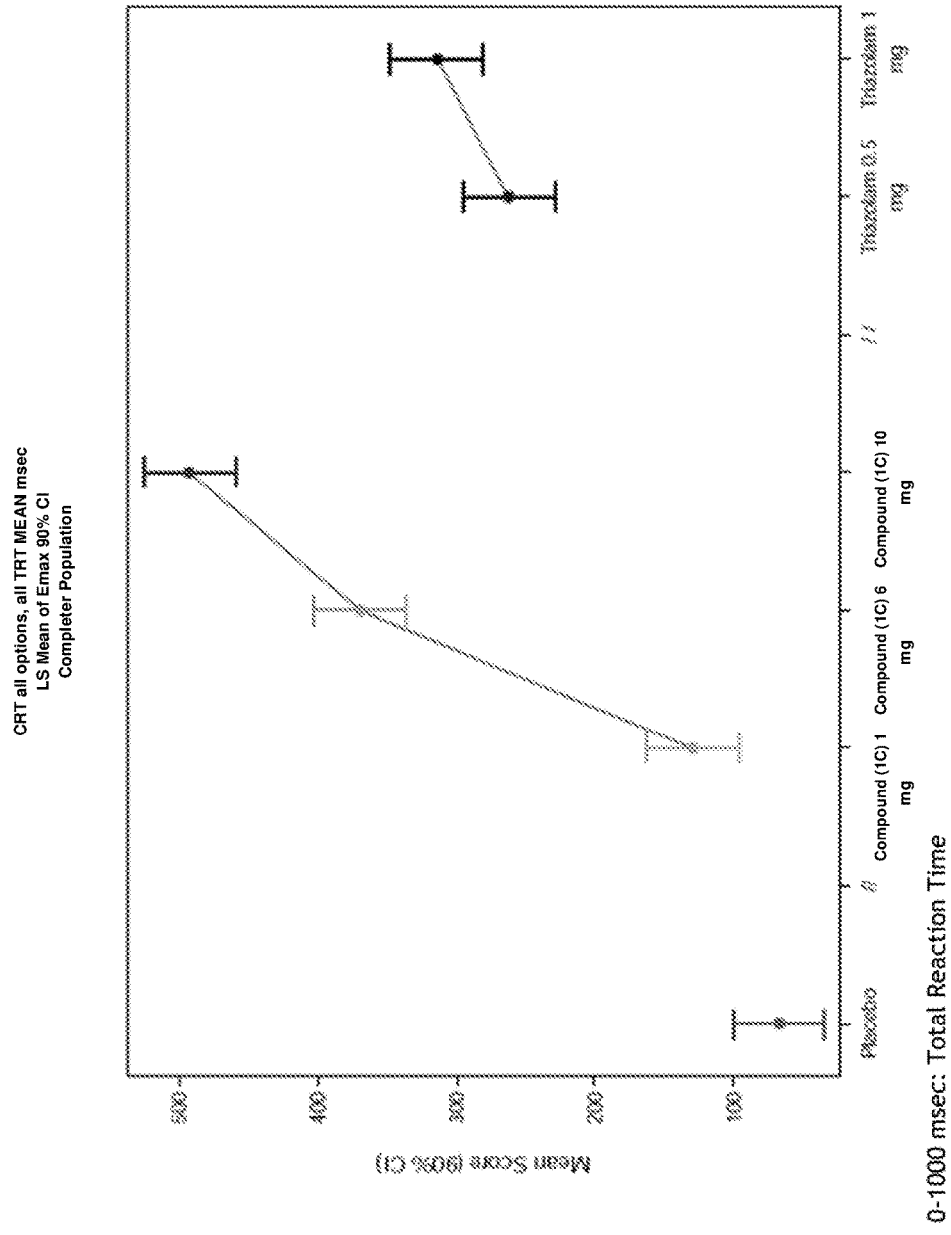
FIG. 20 shows a plot of psychomotor performance, choice reaction time ("CRT"), to Compound (1C) at doses of 1 mg, 6 mg, and 10 mg, triazolam at doses of 0.5 mg and 1.0 mg, and placebo in Example 11.

Cognitive and Psychomotor Effects, including the Divided Attention Test (DAT) results are shown in FIG. 19, and Choice Reaction Time (CRT) results are shown in FIG. 20. These tests were included to provide objective assessment of pharmacologic effects.

Choice Reaction Time is a computer-based test which involves decision-making. Two words appear on the computer screen: "Yes" and "No". The subject pressed the corresponding button as quickly as possible. The CRT task is a classic test of reaction time used to measure psychomotor performance. During this test, the participant was presented with an onscreen equivalent of the numeric keypad. The participant was required to quickly press the buttons on a separate keypad that corresponds with the keys illuminated on the screen. The CRT task comprised 3 outcome variables: RRT, MRT, and TRT. RRT is the time it takes for a participant to notice the light (i.e., the time between stimulus onset and the participant lifting his or her finger from the start button). MRT indexes the movement component of this task and is the time between the participant lifting his or her finger from the start button and touching the response button. TRT is the sum of RRT and MRT.

The Divided Attention test is a manual-tracking test with a simultaneous visual target detection component. The participant was provided with a joystick with a trigger to execute this measure. During testing, the participant was presented with the image of an airplane and a randomly curving road. As the road moves down the screen, the participant was to try and position the image of the airplane over the center of the road.

Fifty subjects were treated and completed the study, with the following endpoints, and the study results are summarized in Table 6, and patient demographics are summarized in Table 7:

TABLE 6

Overview of Key Endpoint (Drug Liking E.)

| | Results |
|---|---|
| Qualification Phase | To select subjects who can discriminate between positive controls and placebo to enter the study. |
| Hypothesis 1: Assay sensitivity | Assay sensitivity met |
| Triazolam 0.5 and 1 mg vs. placebo | Triazolam 1 mg had greater drug liking from placebo than Triazolam 0.5 mg. |
| Hypothesis 2: Positive Comparators Comparison | Drug liking for the compound of Compound (1C) 1 mg was significantly lower than |
| Comparison of Compound (1C) doses 1, 6 and 10 mg with Triazolam 0.5 and 1 mg | Triazolam 0.5 and 1 mg; Drug liking for Compound (1C) 6 mg and 10 mg was not significantly different from Triazolam 0.5 and 1 mg |
| Hypothesis 3: Compound (1C) vs Placebo Abuse Potential of Compound (1C), 6 and 10 mg and Placebo | Drug liking for Compound (1C) 1 mg from placebo was similar to placebo (upper bound was significantly <11 point margin) Drug liking for Compound (1C) 6 and 10 mg were significantly higher than drug liking for placebo |
| Safety and Tolerability | |

Compound (1C) doses were well tolerated. Compound (1C) at the 1 mg dose had a more preferable AE profile than triazolam, and Compound (1C) at 6 and 10 mg doses had similar profiles as triazolam

TABLE 7

Human Abuse Liability Demographics

| Age | N | 50 |
|---|---|---|
| | Mean (SD) | 38.0 (8.7) |
| | Min, Max | 23, 55 |
| Sex | Male | 40 (80%) |
| | Female | 10 (20%) |
| Race | White | 22 (44%) |
| | Black | 26 (52%) |
| | Other | 2 (4%) |
| BMI | Mean (SD) | 26.24 (3.28) |
| | Min, Max | 18.9, 31.7 |

Triazolam, at its therapeutically indicated daily doses of 0.5 mg or 1.0 mg was administered to study subjects, and the Drug Liking Visual Analog Scale ("VAS") results were evaluated for placebo and both dosage levels of triazolam. The results are shown in Table 8, below.

TABLE 8

Drug Liking VAS - EMAX Triazolam 0.5 mg, 1 mg vs Placebo

| Summary Stats | Placebo | Triazolam 0.5 mg | Triazolam 1 mg |
|---|---|---|---|
| LSMean | 55.1 | 75.5 | 78.6 |
| 90% CI | 52.9, 57.4 | 72.1, 79.0 | 74.5, 82.8 |
| Diff from Placebo LSMean | | 20.4 | 23.5 |
| 90% CI | | 16.6, 24.2 | 19.1, 27.9 |
| P-value for 10 point difference | | <0.0001 | <0.0001 |

Both Triazolam 0.5 mg and 1 mg showed mean differences from placebo that were significant (i.e., >10 or 15 point margin) showing the study validity. Triazolam 1 mg exhibited a larger difference from placebo (23.5 points) than Triazolam 0.5 mg (20.4 points) Compound (1C) at daily doses of 1.0 mg, 6.0 mg, and 10.0 mg was administered to study subjects, and the Drug Liking VAS results were evaluated for Compound (1C) at all four dosage levels and compared to triazolam (0.5 mg and 1.0 mg) and placebo, as shown in Tables 9 and 10, below.

TABLE 9

Drug Liking VAS - $E_{MAX}$ Comparison to Triazolam 0.5 mg, 1 mg

| Summary Stats | Placebo (N = 50) | Triazolam 0.5 mg (N = 50) | Triazolam 1 mg (N = 50) | Cmpd. (1C) 1 mg (N = 50) | Cmpd. (1C) 6 mg (N = 50) | Cmpd. (1C) 10 mg (N = 50) |
|---|---|---|---|---|---|---|
| LSMean | 55.1 | 75.5 | 78.6 | 58.1 | 72.82 | 76.4 |
| 90% CI | 52.9, 57.4 | 72.1, 79.0 | 74.5, 82.8 | 55.0, 61.3 | 68.7, 77.0 | 72.0, 80.7 |
| *Triazolam 0.5 mg - Cmpd. (1C)* | | | | | | |
| LSMean | | | | 17.4 | 2.7 | −0.8 |
| Lower 90% CI | | | | 13.2 | −2.3 | −6.0 |
| P-Value | | | | <0.0001 | 0.188 | 0.603 |
| *Triazolam 1 mg - Cmpd. (1C)* | | | | | | |
| LSMean | | | | 20.5 | 5.8 | 2.3 |
| Lower 90% CI | | | | 15.7 | 0.3 | −3.3 |
| P-Value | | | | <0.0001 | 0.88 | 0.98 |

Drug liking for Compound (1C) 1 mg was statistically smaller than triazolam 0.5 mg and 1 mg. Drug liking for Compound (1C) at both 6 mg and 10 mg were not statistically different from triazolam 0.5 mg and 1 mg.

TABLE 10

Drug Liking VAS - $E_{MAX}$ comparison to placebo (11 point margin)

| Summary Stats | Placebo (N = 50) | Triazolam 0.5 mg (N = 50) | Triazolam 1 mg (N = 50) | Cmpd. 1 mg (N = 50) | Cmpd. 6 mg (N = 50) | Cmpd. 10 mg (N = 50) |
|---|---|---|---|---|---|---|
| LSMean | 55.1 | 75.5 | 78.6 | 58.1 | 72.82 | 76.4 |
| 90% CI | 52.9, 57.4 | 72.06, 79.01 | 74.5, 82.8 | 55.0, 61.3 | 68.7, 77.0 | 72.0, 80.7 |
| Diff from Placebo LSMean | | 20.4 | 23.5 | 3.0 | 17.7 | 21.2 |
| 90% CI | | | | −0.5, 6.5 | 13.3, 22.1 | 16.7, 25.8 |
| Probability difference from PBO > 11 | | | | 0.0001 | 0.993 | 0.999 |

Drug liking for Compound (1C) 1 mg was not significantly greater than placebo, while Compound (1C) at 6.0 mg and 10.0 mg did show greater drug liking than placebo.

For safety and tolerability, the adverse event ("AE") profile arising during administration of Compound (1C) was monitored and compared with triazolam and placebo, and the results are shown in Table 11, below.

TABLE 11

Most Frequen Adverse Events

| Preferred Term | Placebo N = 50 n (%) | Triazolam 0.5 mg N = 50 n (%) | Triazolam 1 mg N = 50 n (%) | Compd. (1C) 1 mg N = 50 n (%) | Compd. (1C) 6 mg N = 50 n (%) | Compd. (1C) 10 mg N = 50 n (%) |
|---|---|---|---|---|---|---|
| Somnolence | 11 (22) | 45 (90) | 49 (98) | 20 (40) | 45 (90) | 47 (94) |
| Ataxia | 1 (2) | 21 (42) | 28 (56) | 1 (2) | 7 (14) | 13 (26) |
| Dizziness | 2 (4) | 7 (14) | 6 (12) | 2 (4) | 3 (6) | 5 (10) |
| Hiccups | 1 (2) | 10 (20) | 14 (28) | 0 | 0 | 0 |
| Amnesia | 0 | 3 (6) | 12 (24) | 0 | 0 | 0 |
| Headache | 1 (2) | 2 (4) | 0 | 5 (10) | 2 (4) | 2 (4) |
| Diplopia | 0 | 4 (8) | 5 (10) | 0 | 0 | 2 (4) |
| Vision blurred | 1 (2) | 3 (6) | 2 (4) | 0 | 2 (4) | 3 (6) |
| Nausea | 0 | 0 | 1 (2) | 1 (2) | 2 (4) | 2 (4) |
| Euphoric mood | 0 | 1 (2) | 2 (4) | 0 | 1 (2) | 1 (2) |

Adverse events were coded to MedDRA terms. Data for AEs were analyzed using the treatment-emergent signs and symptoms (TESS) philosophy. Treatment-emergent signs and symptoms are defined as AEs that:
  Emerge during treatment, having been absent at pretreatment; or
  Reemerge during treatment, having been present at pretreatment but stopped prior to treatment; or
  Worsen in intensity during treatment relative to the pretreatment state, when the AE is continuous.

Subjects were counted only once in the incidence count for a specific MedDRA Preferred Term, although a MedDRA Preferred Term might be reported more than once for a particular subject. Separate summaries will be provided for Treatment-emergent AEs ("TEAEs") by maximum intensity (mild, moderate, severe) and relationship (yes, no) to study drug. A TEAE was considered related to study drug if the investigator reported the event to be "definitely, probably, possibly, or unlikely" related to treatment on the CRF.

Oxygen saturation was also measured for each arm of the study, and the results are shown in FIG. 25.

Assay sensitivity was met, thus confirming study validity. Drug liking for both triazolam 0.5 mg and 1 mg were significantly greater than placebo and triazolam 1 mg had greater drug liking from placebo than triazolam 0.5 mg.

Drug liking for Compound (1C) 1 mg was statistically less than triazolam 0.5 mg and 1 mg.

Drug liking for Compound (1C) 6 mg and 10 mg were not statistically different from triazolam 0.5 mg and 1 mg.

Drug liking for Compound (1C) 1 mg was similar to placebo. Drug liking for Compound (1C) 6 and 10 mg were significantly greater than drug liking for placebo Compound (1C) was well tolerated. This study demonstrated Compound (1C) at 1 mg had a more preferable AE profile than triazolam, and for Compound (1C) at 6 mg and 10 mg (i.e., supratherapeutic doses) certain AE results, including, ataxia, hiccups, amnesia, and diplopia, were superior to triazolam administered at therapeutic doses.

6.12 Example 12: Pharmacokinetic Profile of Compound (1C) in the Presence and Absence of Alcohol Consumption This study was designed to evaluate the safety and pharmacokinetic ("PK") interactions between Compound (1C) and alcohol in healthy subjects. Alcohol at 0.7 g/kg and/or Compound (1C) tablets at 2 and 6 mg were administered alone or co-administered using the same formulations described in Example 11. The study was designed as a single-site, randomized, single-dose, double-blinded, placebo-controlled crossover study, and 46 subjects completed treatment as part of the study.

The dose of alcohol at 0.7 g/kg was consistent with the NIAAA definition of binge drinking, which can lead to blood alcohol concentration of approximately 0.08 g/dL. In the United States this is generally considered the level at which a person is legally impaired. In addition, such dose level has been studied in previously completed relevant alcohol interaction study in which the safety and tolerability were established in a similar population (Hong Sun et al. "Psychomotor effects, pharmacokinetics and safety of the orexin receptor antagonist suvorexant administered in combination with alcohol in healthy subjects." *Journal of Psychopharmacology* 2015, Vol. 29(11) 1159-1169).

Briefly, blinded alcoholic beverage or placebo beverage was consumed over a 20- to 30-minute period. The beverage was divided into 3 parts, with approximately ⅓ administered (consumed to completion by subject at their own pace) every 10 minutes, over the period of 10 minutes, in order to control for drinking rate.

Ten minutes prior to dosing with Compound (1C) ("minute −10"), subjects started to drink the first of the 3 portions. Time 0 (Compound (1C) administration) began when the second of the 3 portions are served. Subjects swallowed Compound (1C) with the alcoholic beverage, with small sips of water as needed if the subject could not drink the alcohol quickly enough to consume the alcohol. The final portion of alcohol was given to the subject to consume 10 minutes after Compound (1C) dosing. A mouthwash with water was provided before and at the end of dosing. A mouth check was performed to verify that the Compound (1C) doses administered are swallowed. Vital signs and oxygen saturation, $SpO_2$, (FIG. 26) were collected for evaluation by the investigator.

Blood samples for determining plasma concentrations of Compound (1C) and whole blood concentrations of alcohol were obtained from each subject during each of the treatment periods. For each subject, the following PK metrics were calculated, whenever possible, based on the plasma concentrations of Compound (1C) and blood alcohol.

$AUC_t$ Area under the plasma concentration-time curve from hour 0 to the last measurable plasma concentration, calculated by the linear trapezoidal method.

$AUC_{inf}$ Area under the plasma concentration-time curve extrapolated to infinity:

$$AUCt + \frac{Ct}{\lambda z}$$

Where Ct is the last measurable plasma concentration and az is the apparent terminal phase rate constant;

$C_{max}$ Maximum observed plasma concentration
$T_{max}$ Time to maximum plasma concentration
$T_{1/2}$ Apparent terminal phase half-life:

$$T_{1/2} = (\ln 2)/\lambda_z$$

Fe % Fraction of unchanged Compound (1C) excreted in urine at 0 and 48 h

The PK profile of alcohol at 0.7 g/kg and/or Compound (1C) at 2 and 6 mg administered alone or co-administered is shown in FIG. 23 and Table 12, below.

TABLE 12

PK Profile of Compound (1C) with and without and Alcohol

| Mean (CV %) | Cmax (ng/mL) | Tmax (hr) | AUC (ng/mL * hr) | T1/2 (hr) | Fe (%) |
|---|---|---|---|---|---|
| 2 mg + EtOH | 31.0 (20) | 1.8 (40) | 136 (16) | 3.9 (31) | 84 (33) |
| 2 mg alone | 28.2 (17) | 1.7 (25) | 130 (15) | 4.0 (33) | 81 (12) |
| 6 mg + EtOH | 84.9 (23) | 1.8 (56) | 415 (19) | 4.5 (8) | 80 (20) |
| 6 mg alone | 78.3 (14) | 1.9 (34) | 402 (13) | 4.5 (8) | 81 (10) |

This data shows that administering Compound (1C) in the presence of alcohol does not alter the PK profile of Compound (1C). Likewise, the PK profile of ethanol was not affected by the co-administration of Compound (1C) at 2 mg or 6 mg with ethanol, which had the same PK profile as ethanol administered with placebo, as shown in FIG. 24. The lack of PK interaction between Compound (1C) and ethanol is an important advantage for a drug that may be administered to subjects who may relapse with alcohol consumption, thereby mixing Compound (1C) and alcohol.

6.13 Example 13: Human Liver Metabolism Studies

Compound (1C) has been evaluated in approximately 180 healthy subjects and 50 subjects with general insomnia. The highest doses tested in healthy subjects were for a 30-mg single dose and a 10-mg multiple dose (once daily nighttime dose for 14 days). The highest dose tested in subjects with insomnia was 10 mg.

The PK of Compound (1C) has been well characterized in a suspension formulation of up to 30 mg in 0.5% w/w methylcellulose solution and in a tablet formulation up to 10 mg, where the doses may be achieved by co-administering more than one tablet. Compound (1C) exhibits fast absorption followed by rapid elimination, with a mean time to reach the maximum observed plasma concentration ($T_{max}$) of about 1.5 hours and a mean apparent terminal half-life ($t_{1/2}$) determined to be between 2 to 3 hours. Renal elimination has been shown as the major elimination pathway for Compound (1C), with 80-100% of unchanged drug recovered within 48 hours in urine. The renal clearance of Compound (1C) (adjusted by plasma protein binding) determined from completed studies seems to be higher than the human glomerular filtration rate, indicating the involvement of active secretion possibly mediated by renal transporters in renal clearance. No major metabolite has been identified in human plasma. After a single oral administration, Compound (1C) showed approximately dose-proportional exposure up to 10 mg. Upon once a day dosing for 2 weeks, Compound (1C) showed approximately dose-proportional exposure up to 10 mg. No apparent accumulation was observed with an accumulation ratio determined at 1.2:1.

Compound (1C) was safe and well tolerated across all tested dose levels with no serious adverse events (SAEs) reported. The most frequent treatment-emergent adverse event (TEAEs) experienced by subjects was somnolence.

No concerning laboratory findings (including no incidences of crystalluria or hematuria) and no clinically significant findings on vital signs and electrocardiograms (ECGs) have been attributed to Compound (1C). Data from completed studies indicated that 6 mg was well tolerated in both healthy subjects and those with insomnia after nighttime dosing, with the exception of expected next day residual effects on alertness, cognitive, and motor functions. The next day residual effects was dose-dependent and generally decreased (back to placebo levels) after 8 hours post dosing when dose was equal or lower that 2 mg.

TABLE 13

Summary of Compound (1C) Renal PK parameters

| Cohort (n = each) | Dose (mg) | Mean Renal Clearance (mL/min) | Mean Total Amount Excreted Unchanged (mg) | Mean % Dose Excreted Unchanged |
|---|---|---|---|---|
| 1 | 3 | 275 | 2.66 | 89% |
| 2 | 10 | 266 | 6.95 | 70% |
| 3 | 30 | 270 | 8.37 | 28% |

TABLE 14

Summary of Urine Compound (1C) Pharmacokinetic Metrics

| Metric (Unit) | Study Treatment | | | |
|---|---|---|---|---|
| | Cmpd. (1C) 0.2 mg aqueous suspension (N =24) | Cmpd. (1C) 0.6 mg aqueous suspension (N =24) | Cmpd. (1C) 2.0 mg aqueous suspension (N =23) | Cmpd. (1C) 6.0 mg aqueous suspension (N =25) |
| Ae (mg) | | | | |
| Mean | 0.2232 | 0.6891 | 2.165 | 6.653 |
| SD | 0.039746 | 0.16486 | 0.43592 | 0.95551 |
| CV (%) | 17.81 | 23.93 | 20.13 | 14.36 |
| Minimum, maximum | 0.138, 0.311 | 0.0550, 0.889 | 1.01, 2.84 | 4.08, 8.08 |
| Fe (%) | | | | |
| Mean | 111.60 | 114.84 | 108.26 | 110.88 |
| SD | 19.873 | 27.477 | 21.796 | 15.925 |
| CV (%) | 17.81 | 23.93 | 20.13 | 14.36 |
| Minimum, maximum | 68.9, 155.3 | 9.2, 148.2 | 50.4, 142.0 | 68.0, 134.6 |

Abbreviations:
CV = coefficient of variation;
Fe = fraction of dose excreted unchanged Compound (1C) in urine over 24 hours;
N = number of subjects in the population;
SD = standard deviation;
Xu = cumulative amount of unchanged Compound (1C) excreted in urine over each collection interval.

Urine PK Results

Most of the unchanged Compound (1C) across the dose range was excreted in urine during the first 8 hours following dosing administration for both days 1 (single-dose) and 16 (steady-state). The mean fraction of dose excreted unchanged in urine over 48 hours (Fe48) was 96%, 100%, and 84% for Compound (1C) 0.6, 2, and 10 mg, respectively for day 1. The mean fraction of dose excreted unchanged in urine over 24 hours (Fe24) was 90%, 102%, and 81%, for Compound (1C) 0.6, 2, and 10 mg, respectively for day 16. The mean $CL_r$ of Compound (1C) was similar across all dose levels, ranging from 16.43 to 21.23 L/h, following dosing on both days 1 and 16.

TABLE 15

Summary of Urine Compound (1C) Pharmacokinetic Metrics

| Metric (units) | Study Treatment | | | |
|---|---|---|---|---|
| | Cmpd. (1C) 2 mg with Alcohol (N = 46) | Cmpd. (1C) 6 mg with Alcohol (N = 48) | Cmpd. (1C) 2 mg Alone (N = 48) | Cmpd. (1C) 6 mg Alone (N = 47) |
| Fe (%) | | | | |
| Mean | 83.6 | 79.6 | 80.7 | 80.8 |
| SD | 27.4 | 16.24 | 9.584 | 7.724 |
| CV (%) | 32.74 | 20.4 | 11.9 | 9.55 |
| Minimum, maximum | 48.3, 255 | 33.1, 164 | 66.1, 130 | 49.5, 101 |
| $CL_r$ (L/h) | | | | |
| Mean | 12.6 | 11.9 | 12.7 | 12.3 |
| SD | 5.00 | 2.86 | 2.68 | 2.27 |
| CV (%) | 39.6 | 24.1 | 21.1 | 18.4 |
| Minimum, maximum | 8.37, 42.5 | 7.54, 23.4 | 9.27, 23.2 | 7.01, 19.6 |

6.14 Example 14: In Vivo Clearance of Radiolabeled Compound (1C) in Animals

The clearance of Compound (1C) from rats, dogs, and monkeys was determined by analyzing excreta samples from the animals (and controls as required) for a radiolabeled form of the compound.

Specifically, liquid scintillation counting ("LSC") was used for the determination of total radiolabeled Compound (1C) material, i.e., the original or parent compound and its metabolites. The radiolabeled Compound (1C) that was synthesized comprised $^{14}C$ as a phenyl group carbon atom of the quinoxaline skeleton of the molecule and is denoted herein as [$^{14}$C]-Compound (1C). Using $^{14}$C as a radiolabel for pharmacokinetic studies is a recognized technique and embedding the radiolabel into the ring structure was done to limit migration or exchange of the radiolabel to non-Compound (1C)-related molecules. The specific radioactivity for the lot of [$^{14}$C]-Compound (1C) synthesized was 2.50 MBq/mg (67.6 µCi/mg) [3.49 MBq/mg (94.4 µCi/mg) if the material were to be present as the free base form] with a radiochemical purity of greater than 98.5% as determined by HPLC. The synthesized radiolabeled [$^{14}$C]-Compound (1C) was stored away from light at a temperature of −80° C. before use.

Following oral administration of [$^{14}$C]-Compound (1C) (in an appropriate vehicle, e.g., a methyl cellulose suspension) to the experimental animals, excreta samples were collected over specified time intervals. Urine samples were collected at fixed intervals post dosing. Fecal samples were homogenized and diluted prior to being solubilized. Aliquots of these samples were counted following the addition of liquid scintillation fluid thereto. Detection limits for radioactivity in the excreta samples were set at twice the background count (from blank samples) as determined by LSC. The [$^{14}$C]-Compound (1C) was stable for about 4-5 hours in urine at a temperature of about 25° C. and, when kept refrigerated at 4° C., for up to 15 days (rat urine) and 36 days (dog urine). Recovery of [$^{14}$C]-Compound (1C) from rat urine was typically from about 91.6 to about 99.1%. Recovery of [$^{14}$C]-Compound (1C) from dog urine was typically from about 100.9 to about 105.0%.

Oral doses of [$^{14}$C]-Compound (1C) given to rats were rapidly absorbed, widely distributed, and rapidly eliminated. The organs with the highest [$^{14}$C]-Compound (1C) burden following oral dosing of rats were the liver and kidney. Only trace levels (below the limit of quantification) of [$^{14}$C]-Compound (1C)-derived radioactivity were found in any rat tissues 72 hours post dose.

There were no major metabolites of [$^{14}$C]-Compound (1C) detected in all species tested. Only a few minor metabolites were identified by high performance liquid chromatography with tandem mass spectrometry detection ("HPLC-MS-MS") in animal bile, urine, and feces. These metabolites were the 6-hydroxide, the 1-hydroxide, the decarboxylate, and the +2 form of [$^{14}$C]-Compound (1C).

In a one week study, the elimination of [$^{14}$C]-Compound (1C) was largely through feces in male rats and monkeys but through both the urine and feces in dogs; Table 16 below provides a summary of the results where the average % elimination is determined from the average of the ratio of the recovered $^{14}$C amount to amount of $^{14}$C administered as [$^{14}$C]-Compound (1C).

TABLE 16

% Elimination of [$^{14}$C]-Compound (1C)-Derived Radioactivity Within 168 Hours of Oral Dosing

| | Average % Elimination | | |
|---|---|---|---|
| Elimination Route | Rat (male) [a] | Monkey (female) | Dog (male) |
| Fecal [b] | 84.1 | 81.3 | 46.3 |
| Urinary | 14.9 | 20.7 | 50.3 |
| Fecal + Urinary | 99.0 | 102.0 | 96.6 |

[a] Renal drug clearance in female rats is about twice that of males.
[b] Includes unabsorbed and biliary excreted drug.

In a shorter duration study, female rats eliminated more of Compound (1C) via the urine than male rats; Table 17 below summarizes these results.

TABLE 17

% Elimination of Compound (1C)-Derived Radioactivity Within 48 Hours of Oral Dosing

| | Average % Elimination | |
|---|---|---|
| Elimination Route | Rat (male) | Rat (female) |
| Fecal | 41.6 | 27.9 |
| Urinary | 54.4 | 66.8 |
| Fecal + Urinary | 96.0 | 94.7 |

However, it should be noted from the data in Table 17 that the total amount eliminated was substantially identical for male and female rats.

As can be noted from this example, the total average % elimination was extremely high for all species tested, ranging from a low value of about 95% to essentially 100%. In summary, as is evident from the results in this example, [$^{14}$C]-Compound (1C) was poorly metabolized in vivo in all animal species tested.

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. A number of references have been cited, the entire disclosures of which are incorporated herein by reference for all purposes.

What is claimed:

1. A method for treating Insomnia Associated with Alcohol Cessation, comprising administering to a human subject who has been diagnosed with alcohol use disorder a daily dose of from about 0.5 mg to about 2.0 mg of a compound of Formula (IC):

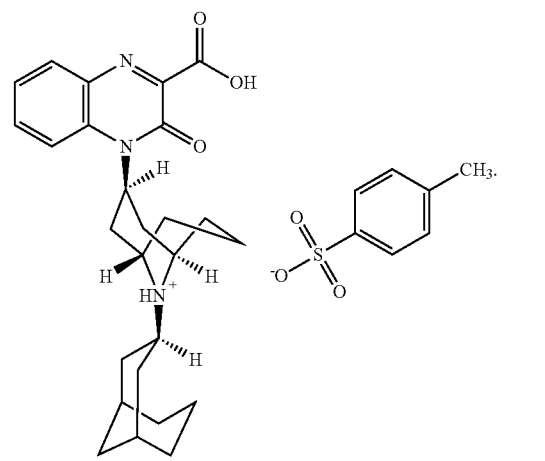

(IC)

wherein the subject has relapsed with alcohol consumption;
wherein the subject has consumed from about 0.05 g/kg to about 5.0 g/kg ethanol; and
wherein (a) the $T_{max}$, AUC, and $T_{1/2}$ resulting from the administration of the compound of Formula (IC) to the subject who has consumed ethanol is not statistically different from the $T_{max}$, AUC, and $T_{1/2}$ resulting from the administration of the compound of Formula (IC) in the absence of ethanol, (b) the $T_{max}$, AUC, and $T_{1/2}$ resulting from the consumption of ethanol with the compound of Formula (IC) is not statistically different from the $T_{max}$, AUC, and $T_{1/2}$ resulting from the consumption the same amount of ethanol in the absence of the compound of Formula (IC), or both (a) and (b).

2. The method of claim wherein 1, wherein the daily dose of the compound of Formula (IC) is administered such that at a time point following administration the compound of Formula (IC) and ethanol are both present in the subject's bloodstream.

3. The method of claim 1, wherein the compound of Formula (IC) is administered in combination with one or more agents directed to treating alcohol use disorder.

4. The method of claim 1, wherein the compound of Formula (IC) is administered concomitantly with one or more agents selected from disulfiram, naltrexone, acamprosate, gabapentin, topiramate, nalmefenem, naloxone, fluoxetine, and quetiapine.

5. The method of claim 1, wherein the daily dose is from about 1.0 mg to about 2.0 mg of the compound of Formula (IC).

6. The method of claim 1, wherein the daily dose is about 1.0 mg of the compound of Formula (IC).

7. The method of claim 1, wherein the daily dose is about 2.0 mg of the compound of Formula (IC).

8. A method for treating Insomnia Associated with Alcohol Cessation, comprising administering to a human subject in need thereof a daily dose of from about 1.0 mg to about 2.0 mg of a compound of Formula (IC):

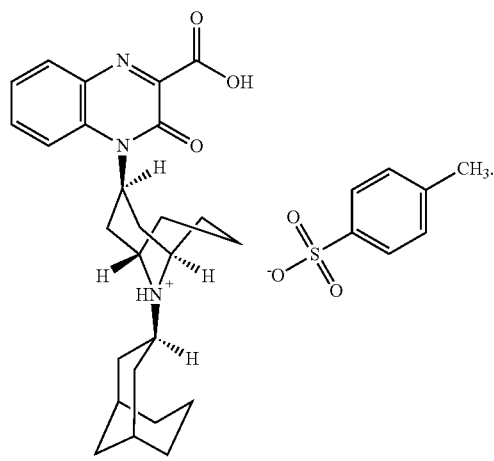

(IC)

wherein the subject has relapsed with alcohol consumption;

wherein the subject has consumed from about 0.05 g/kg to about 5.0 g/kg ethanol; and wherein (a) the $T_{max}$, AUC, and $T_{1/2}$ resulting from the administration of the compound of Formula (IC) to the subject who has consumed ethanol is not statistically different from the $T_{max}$, AUC, and $T_{1/2}$ resulting from the administration of the compound of Formula (IC) in the absence of ethanol, (b) the $T_{max}$, AUC, and $T_{1/2}$ resulting from the consumption of ethanol with the compound of Formula (IC) is not statistically different from the $T_{max}$, AUC, and $T_{1/2}$ resulting from the consumption the same amount of ethanol in the absence of the compound of Formula (IC), or both (a) and (b).

9. The method of claim wherein 8, wherein the daily dose of the compound of Formula (IC) is administered such that at some time point following administration the compound of Formula (IC) and ethanol are present in the subject's bloodstream concurrently.

10. The method of claim 8, wherein the compound of Formula (IC) is administered to a subject who is concomitantly being treated with one or more agents directed to treating alcohol use disorder.

11. The method of claim 8, wherein the compound of Formula (IC) is administered to a subject who is concomitantly being treated with one or more agents selected from disulfiram, naltrexone, acamprosate, gabapentin, topiramate, nalmefenem, naloxone, fluoxetine, and quetiapine.

12. A method for treating Insomnia associated with alcohol use disorder, comprising administering to a human subject in need thereof a daily dose of from about 0.5 mg to about 2.0 mg of a compound of Formula (IC):

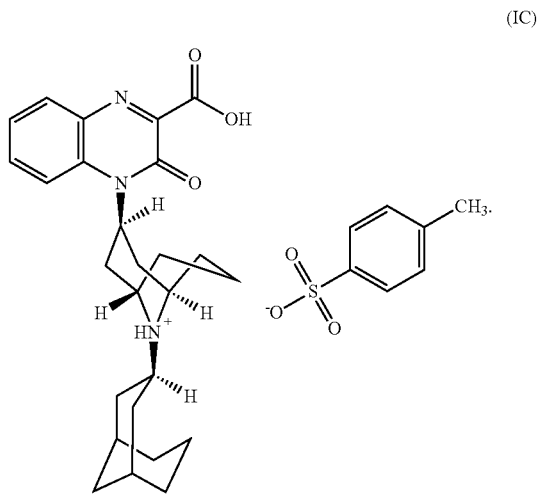

(IC)

wherein the subject has been diagnosed with alcohol use disorder and has a history of polydrug abuse;

wherein the subject has consumed from about 0.05 g/kg to about 5.0 g/kg ethanol; and wherein (a) the $T_{max}$, AUC, and $T_{1/2}$ resulting from the administration of the compound of Formula (IC) to the subject who has consumed ethanol is not statistically different from the $T_{max}$, AUC, and $T_{1/2}$ resulting from the administration of the compound of Formula (IC) in the absence of ethanol, (b) wherein the $T_{max}$, AUC, and $T_{1/2}$ resulting from the consumption of ethanol with the compound of Formula (IC) is not statistically different from the $T_{max}$, AUC, and $T_{1/2}$ resulting from the consumption the same amount of ethanol in the absence of the compound of Formula (IC), or both (a) and (b).

13. The method of claim 12, wherein the daily dose is about 1.0 mg of the compound of Formula (IC).

14. The method of claim 12, wherein the daily dose is about 2.0 mg of the compound of Formula (IC).

15. The method of claim 12, wherein the compound of Formula (IC) is administered to a subject who is concomitantly being treated with one or more agents directed to treating alcohol use disorder.

16. The method of claim 12, wherein the compound of Formula (IC) is administered to a subject who is concomitantly being treated with one or more agents selected from disulfiram, naltrexone, acamprosate, gabapentin, topiramate, nalmefenem, naloxone, fluoxetine, and quetiapine.

* * * * *